(12) United States Patent
Vohra et al.

(10) Patent No.: US 7,718,641 B2
(45) Date of Patent: May 18, 2010

(54) PYRROLO [3,4-H] ISOQUINOLINE COMPOUNDS AND METHODS FOR MODULATING GATED ION CHANNELS

(75) Inventors: Rahul Vohra, Kanata (CA); Joachim Demnitz, Koebenhavn (DK); Philip K. Ahring, Bagsvaed (DK); Zhonghong Gan, Ottawa (CA); Nachhattarpal Gill, Ottawa (CA)

(73) Assignee: Aros Pharma ApS, Bagsvaerd (DE)

( * ) Notice: Subject to any disclaimer, the term of this patent is extended or adjusted under 35 U.S.C. 154(b) by 0 days.

(21) Appl. No.: 11/603,946

(22) Filed: Nov. 22, 2006

(65) Prior Publication Data

US 2007/0191418 A1    Aug. 16, 2007

Related U.S. Application Data

(60) Provisional application No. 60/739,600, filed on Nov. 23, 2005.

(51) Int. Cl.
*C07D 471/04* (2006.01)
*A61K 31/4412* (2006.01)

(52) U.S. Cl. ........................................ 514/183; 514/292

(58) Field of Classification Search ........................ None
See application file for complete search history.

(56) References Cited

U.S. PATENT DOCUMENTS 5,780,493 A    7/1998    Watjen et al.
5,843,945 A    12/1998   Watjen et al.
6,124,285 A    9/2000    Watjen et al.
6,239,128 B1   5/2001    Watjen et al.
6,727,260 B2   4/2004    Varming et al.
7,288,653 B2   10/2007   Varming et al.

FOREIGN PATENT DOCUMENTS

| | | |
|---|---|---|
| CA | 2369746 A1 | 11/2000 |
| CA | 02311483 | 12/2001 |
| CA | 2161783 | 8/2006 |
| EP | 0633262 B1 | 1/1995 |
| WO | WO-93/05043 A1 | 3/1993 |
| WO | WO-94/09000 A1 | 4/1994 |
| WO | WO-96/08494 A1 | 3/1996 |
| WO | WO-96/08495 A1 | 3/1996 |
| WO | WO-98/14447 A1 | 4/1998 |
| WO | WO-99/64420 A1 | 12/1999 |
| WO | WO 00/71102 A2 * | 11/2000 |
| WO | WO-01/55110 A1 | 8/2001 |
| WO | WO-2004/018466 A2 | 3/2004 |
| WO | WO-2004/078733 A1 | 9/2004 |
| WO | WO-2005/014558 A1 | 2/2005 |
| WO | WO-2005/066171 A1 | 7/2005 |

* cited by examiner

*Primary Examiner*—Brandon J Fetterolf
*Assistant Examiner*—Timothy P Thomas
(74) *Attorney, Agent, or Firm*—Lahive & Cockfield, LLP; Cynthia L. Kanik; Brian C. Trinque

(57) ABSTRACT

The present invention relates to compositions and methods to modulate the activity of gated ion channels.

2 Claims, 14 Drawing Sheets

PYRROLO [3,4-H] ISOQUINOLINE COMPOUNDS AND METHODS FOR MODULATING GATED ION CHANNELS

RELATED APPLICATION

This application claims priority to U.S. Provisional Application No. 60/739,600, filed Nov. 23, 2005, entitled "COMPOSITIONS AND METHODS FOR MODULATING GATED ION CHANNELS." The contents of any patents, patent applications, and references cited throughout this specification are hereby incorporated by reference in their entireties.

TECHNICAL FIELD

The present invention relates to compositions which modulate the activity of gated ion channels and methods and uses thereof.

BACKGROUND

Mammalian cell membranes are important to the structural integrity and activity of many cells and tissues. Of particular interest is the study of trans-membrane gated ion channels which act to directly and indirectly control a variety of pharmacological, physiological, and cellular processes. Numerous gated ion channels have been identified and investigated to determine their roles in cell function.

Gated ion channels are involved in receiving, integrating, transducing, conducting, and transmitting signals in a cell, e.g., a neuronal or muscle cell. Gated ion channels can determine membrane excitability. Gated ion channels can also influence the resting potential of membranes, wave forms, and frequencies of action potentials, and thresholds of excitation. Gated ion channels are typically expressed in electrically excitable cells, e.g., neuronal cells, and are multimeric. Gated ion channels can also be found in nonexcitable cells (e.g., adipose cells or liver cells), where they can play a role in, for example, signal transduction.

Among the numerous gated ion channels identified to date are channels that are responsive to, for example, modulation of voltage, temperature, chemical environment, pH, ligand concentration and/or mechanical stimulation. Examples of specific modulators include: ATP, capsaicin, neurotransmitters (e.g., acetylcholine), ions, e.g., $Na^+$, $Ca^+$, $K^+$, $Cl^-$, $H^+$, $Zn^+$, $Cd^+$, and/or peptides, e.g., FMRF. Examples of gated ion channels responsive to these stimuli are members of the DEG/ENaC, TRPV and P2X gene superfamilies.

Members of the DEG/ENaC gene superfamily show a high degree of functional heterogeneity with a wide tissue distribution that includes transporting epithelia as well as neuronal excitable tissues. DEG/ENaC proteins are membrane proteins which are characterized by two transmembrane spanning domains, intracellular N- and C-termini and a cysteine-rich extracellular loop. Depending on their function in the cell, DEG/ENaC channels are either constitutively active like epithelial sodium channels (ENaC) which are involved in sodium homeostasis, or activated by mechanical stimuli as postulated for *C. elegans* degnerins, or by ligands such as peptides as is the case for FaNaC from *Helix aspersa* which is a FMRF amide peptide-activated channel and is involved in neurotransmission, or by protons as in the case for the acid sensing ion channels (ASICs). The mammalian members of this gene family known to date are αENaC (also known as SCNN1A or scnn1A), βENaC (also known as SCNN1B or scnn1B), γENaC (also known as SCNN1G or scnn1G), δENaC (also known as ENaCd, SCNN1D, scnn1D and dNaCh), ASIC1a (also known as ASIC, ASIC1, BNaC2, hBNaC2, ASICalpha, ACCN2 and Accn2), ASIC1b (also known as ASICbeta), ASIC2a (also known as BNC1, MDEG1, BNaC1 and ACCN1), ASIC2b (also known as MDEG2, ASIC2b), ASIC3 (also known as hASIC3, DRASIC, TNaC1, SLNAC1, ACCN3 and Accn3), ASIC4 (also known as BNaC4, SPASIC, ACCN4 and Accn4), BLINaC (also known as hINaC, ACCN5 and Accn5), and hINaC. For a recent review on this gene superfamily see Kellenberger, S. and Schild, L. (2002) *Physiol. Rev.* 82:735, incorporated herein by reference.

There are seven presently known members of the P2X gene superfamily; $P2X_1$ (also known as P2RX1), $P2X_2$ (also known as P2RX2), $P2X_3$ (also known as P2RX3), $P2X_4$ (also known as P2RX4), $P2X_5$ (also known as P2RX5), $P2X_6$ (also known as P2RX6), and $P2X_7$ (also known as P2RX7). P2X protein structure is similar to ASIC protein structure in that they contain two transmembrane spanning domains, intracellular N- and C-termini and a cysteine-rich extracellular loop. All P2X receptors open in response to the release of extracellular ATP and are permeable to small ions and some have significant calcium permeability. P2X receptors are abundantly distributed on neurons, glia, epithelial, endothelia, bone, muscle and hematopoietic tissues. For a recent review on this gene superfamily, see North, R. A. (2002) *Physiol. Rev.* 82:1013, incorporated herein by reference.

The receptor expressed in sensory neurons that reacts to the pungent ingredient in chili peppers to produce a burning pain is the capsaicin (TRPV or vanilloid) receptor, denoted TRPV1 (also known as VR1, TRPV1 alpha, TRPV1beta). The TRPV1 receptor forms a nonselective cation channel that is activated by capsaicin and resiniferatoxin (RTX) as well as noxious heat (>43° C.), with the evoked responses potentiated by protons, e.g., $H^+$ ions. Acid pH is also capable of inducing a slowly inactivating current that resembles the native proton-sensitive current in dorsal root ganglia. Expression of TRPV1, although predominantly in primary sensory neurons, is also found in various brain nuclei and the spinal cord (*Physiol. Genomics* 4:165-174, 2001).

Two structurally related receptors, TRPV2 (also known as VRL1 and VRL) and TRPV4 (also known as VRL-2, Trp12, VROAC, OTRPC4), do not respond to capsaicin, acid or moderate heat but rather are activated by high temperatures (Caterina, M. J., et al. (1999) *Nature.* 398(6726):436-41). In addition, this family of receptors, e.g., the TRPV or vanilloid family, contains the ECAC-1 (also known as TRPV5 and CAT2, CaT2) and ECAC-2 (also known as TRPV6, CaT, ECaC, CAT1, is CATL, and OTRPC3) receptors which are calcium selective channels (Peng, J. B., et al. (2001) *Genomics* 76(1-3):99-109). For a recent review of TRPV (vanilloid) receptors, see Szallasi, A. and Blumberg, P. M. (1999) *Pharmacol. Rev.* 51:159, incorporated herein by reference.

The ability of the members of the gated ion channels to respond to various stimuli, for example, chemical (e.g., ions), thermal and mechanical stimuli, and their location throughout the body, e.g., small diameter primary sensory neurons in the dorsal root ganglia and trigeminal ganglia, as well data derived from in vitro and in vivo models has implicated these channels in numerous neurological diseases, disorders and conditions. For example, it has been shown that the rat ASIC2a channel is activated by the same mutations as those causing neuronal degeneration in *C. elegans*. In addition, these receptors are activated by increases in extracellular proton, e.g., $H^+$, concentration. By infusing low pH solutions into skin or muscle as well as prolonged intradermal infusion of low pH solutions creates a change in extracellular pH that mimics the hyperalgesia of chronic pain. Furthermore, transgenic mice, e.g., ASIC2a, ASIC3, P2X$_3$ transgenic mice, all have modified responses to noxious and non-noxious stimuli. Thus, the biophysical, anatomical and pharmacological properties of the gated ion channels are consistent with their involvement in nociception.

Research has shown that ASICs play a role in pain, neurological diseases and disorders, gastrointestinal diseases and disorders, genitourinary diseases and disorders, and inflammation. For example, it has been shown that ASICs play a role in pain sensation (Price, M. P. et al., Neuron. 2001; 32(6): 1071-83; Chen, C. C. et al., Neurobiology 2002; 99(13) 8992-8997), including visceral and somatic pain (Aziz, Q., Eur. J. Gastroenterol. Hepatol. 2001; 13(8):891-6); chest pain that accompanies cardiac ischemia (Sutherland, S. P. et al. (2001) Proc Natl Acad Sci USA 98:711-716), and chronic hyperalgesia (Sluka, K. A. et al., Pain. 2003; 106(3):229-39). ASICs in central neurons have been shown to possibly contribute to the neuronal cell death associated with brain ischemia and epilepsy (Chesler, M., Physiol. Rev. 2003; 83: 1183-1221; Lipton, P., Physiol. Rev. 1999; 79:1431-1568). ASICs have also been shown to contribute to the neural mechanisms of fear conditioning, synaptic plasticity, learning, and memory (Wemmie, J. et al., J. Neurosci. 2003; 23(13):5496-5502; Wemmie, J. et al., Neuron. 2002; 34(3):463-77). ASICs have been shown to be involved in inflammation-related persistent pain and inflamed intestine (Wu, L. J. et al., J. Biol. Chem. 2004; 279(42):43716-24; Yiangou, Y., et al., Eur. J. Gastroenterol. Hepatol. 2001; 13(8): 891-6), and gastrointestinal stasis (Holzer, Curr. Opin. Pharm. 2003; 3: 618-325). Recent studies done in humans indicate that ASICs are the primary sensors of acid-induced pain (Ugawa et al., J. Clin. Invest. 2002; 110: 1185-90; Jones et al., J. Neurosci. 2004; 24: 10974-9). Furthermore, ASICs are also thought to play a role in gametogenesis and early embryonic development in *Drosophila* (Darboux, I. et al., J. Biol. Chem. 1998; 273(16): 9424-9), underlie mechanosensory function in the gut (Page, A. J. et al. Gastroenterology. 2004; 127(6):1739-47), and have been shown to be involved in endocrine glands (Grunder, S. et al., Neuroreport. 2000; 11(8): 1607-11). Therefore, compounds that modulate these gated ion channels would be useful in the treatment of such diseases and disorders.

SUMMARY OF THE INVENTION

In one aspect, the invention provides a compound of the Formula 1, Formula 2, Formula 3, Formula 4 or Formula 5, as well as a compound selected from the group consisting of 5-(5-fluoro-2-methoxyphenyl)-6,7,8,9-tetrahydro-3-(hydroxyimino)-8-methyl-1H-pyrrolo[3,2-h]isoquinoline-2 (3H)-one; 5-(5-fluoro-2-methoxyphenyl)-6,7,8,9-tetrahydro-3-(hydroxyimino)-8-ethyl-1H-pyrrolo[3,2-h]isoquinoline-2(3H)-one; 5-(5-chloro-2-methoxyphenyl)-6,7,8,9-tetrahydro-3-(hydroxyimino)-8-methyl-1H-pyrrolo[3,2-h]isoquinoline-2(3H)-one; 5-(3,5-dimethylphenyl)-6,7,8,9-tetrahydro-3-(hydroxyimino)-8-methyl-1H-pyrrolo[3,2-h]isoquinoline-2(3H)-one; 5-(3,5-dimethylphenyl)-6,7,8,9-tetrahydro-3-(hydroxyimino)-8-ethyl-1H-pyrrolo[3,2-h]isoquinoline-2(3H)-one; 5-(2,5-dimethylphenyl)-6,7,8,9-tetrahydro-3-(hydroxyimino)-8-ethyl-1H-pyrrolo[3,2-h]isoquinoline-2(3H)-one; 5-(5-chloro-2-methoxyphenyl)-6,7,8,9-tetrahydro-3-(hydroxyimino)-8-ethyl-1H-pyrrolo[3,2-h]isoquinoline-2(3H)-one; 5-phenyl-6,7,8,9-tetrahydro-3-(hydroxyimino)-8-ethyl-1H-pyrrolo[3,2-h]isoquinoline-2(3H)-one; 5-(2,3-dimethyl-phenyl)-8-ethyl-6,7,8,9-tetrahydro-1H-pyrrolo[3,2-h]isoquinoline-2,3-dione 3-oxime; 8-ethyl-5-(2-methoxy-phenyl)-6,7,8,9-tetrahydro-1H-pyrrolo[3,2-h]isoquinoline-2,3-dione 3-oxime; and 5-(2-ethoxy-phenyl)-8-ethyl-6,7,8,9-tetrahydro-1H-pyrrolo[3,2-h]isoquinoline-2,3-dione 3-oxime.

In one aspect, the invention provides a method of modulating the activity of a gated ion channel, comprising contacting a cell expressing a gated ion channel with an effective amount of a compound of the invention In another embodiment of the invention, contacting the cells with an effective amount of a compound of the invention inhibits the activity of the gated ion channel. In yet another embodiment, the gated ion channel is comprised of at least one subunit selected from the group consisting of a member of the DEG/ENaC, P2X, and TRPV gene superfamilies. In still another embodiment, the gated ion channel is comprised of at least one subunit selected from the group consisting of αENaC, βENaC, γENaC, δENaC, ASIC1a, ASIC1b, ASIC2a, ASIC2b, ASIC3, ASIC4, BLINaC, hINaC, P2X$_1$, P2X$_2$, P2X$_3$, P2X$_4$, P2X$_5$, P2X$_6$, P2X$_7$, TRPV1, TRPV2, TRPV3, TRPV4, TRPV5, and TRPV6. In another embodiment, the gated ion channel is homomultimeric. In still another embodiment, the gated ion channel is heteromultimeric. In yet another embodiment, the DEG/ENaC gated ion channel is comprised of at least one subunit selected from the group consisting of αENaC, βENaC, γENaC, δENaC, BLINaC, hINaC, ASIC1a, ASIC1b, ASIC2a, ASIC2b, ASIC3, and ASIC4. In another embodiment, the DEG/ENaC gated ion channel is comprised of at least one subunit selected from the group consisting of ASIC1a, ASIC1b, ASIC2a, ASIC2b, ASIC3, and ASIC4. In still another embodiment, the gated ion channel comprises ASIC1a and/or ASIC3. In yet another embodiment, the P2X gated ion channel comprises at least one subunit selected from the group consisting of P2X$_1$, P2X$_2$, P2X$_3$, P2X$_4$, P2X$_5$, P2X$_6$, and P2X$_7$. In another embodiment, the TRPV gated ion channel comprises at least one subunit selected from the group TRPV1, TRPV2, TRPV3, TRPV4, TRPV5, and TRPV6. In still another embodiment, the heteromultimeric gated ion channels include the following combinations of gated ion channels: αENaC, βENaC and γENaC; αENaC, βENaC and δENaC; ASIC1a and ASIC3; ASIC1b and ASIC3; ASIC2a and ASIC3; ASIC2b and ASIC3; ASIC1a, ASIC2a and ASIC3; P2X$_1$ and P2X$_2$; P2X$_1$ and P2X$_5$; P2X$_2$ and P2X$_3$; P2X$_2$ and P2X$_6$; P2X$_4$ and P2X$_6$; TRPV1 and TRPV2; TRPV5 and TRPV6; and TRPV1 and TRPV4. In yet another embodiment, the heteromultimeric gated ion channels include the following combinations of gated ion channels: ASIC1a and ASIC2a; ASIC2a and ASIC2b; ASIC1b and ASIC3; and ASIC3 and ASIC2b.

In another embodiment of the invention, the activity of the gated ion channel is associated with pain. In yet another embodiment, the activity of the gated ion channel is associated with an inflammatory disorder. In still another embodiment, the activity of the gated ion channel is associated with a neurological disorder.

In another embodiment, the pain is selected from the group consisting of cutaneous pain, somatic pain, visceral pain and neuropathic pain. In still another embodiment, the pain is acute pain or chronic pain. In yet another embodiment, the cutaneous pain is associated with injury, trauma, a cut, a laceration, a puncture, a burn, a surgical incision, an infection or acute inflammation. In another embodiment, the somatic pain is associated with an injury, disease or disorder of the musculoskeletal and connective system. In still another embodiment, the injury, disease or disorder is selected from the group consisting of sprains, broken bones, arthritis, psoriasis, eczema, and ischemic heart disease. In yet another embodiment, the visceral pain is associated with an injury, disease or disorder of the circulatory system, the respiratory system, the gastrointestinal system, or the genitourinary system. In another embodiment, the disease or disorder of the circulatory system is selected from the group consisting of ischaemic heart disease, angina, acute myocardial infarction, cardiac arrhythmia, phlebitis, intermittent claudication, varicose veins and hemorrhoids. In still another embodiment, the disease or disorder of the respiratory system is selected from the group consisting of asthma, respiratory infection, chronic bronchitis and emphysema. In yet another embodiment, the disease or disorder of the gastrointestinal system is selected from the group consisting of gastritis, duodenitis, irritable bowel syndrome, colitis, Crohn's disease, gastrointestinal reflux disease, ulcers and diverticulitis.

In another embodiment, the disease or disorder of the genitourinary system is selected from the group consisting of cystitis, urinary tract infections, glomuerulonephritis, polycystic kidney disease, kidney stones and cancers of the genitourinary system. In still another embodiment, the somatic pain is selected from the group consisting of arthralgia, myalgia, chronic lower back pain, phantom limb pain, cancer-associated pain, dental pain, fibromyalgia, idiopathic pain disorder, chronic non-specific pain, chronic pelvic pain, postoperative pain, and referred pain. In yet another embodiment, the neuropathic pain is associated with an injury, disease or disorder of the nervous system. In another embodiment, the injury, disease or disorder of the nervous system is selected from the group consisting of neuralgia, neuropathy, headache, migraine, psychogenic pain, chronic cephalic pain and spinal cord injury.

In another embodiment of the invention, the activity of the gated ion channel is selected from an inflammatory disorder of the musculoskeletal and connective tissue system, the respiratory system, the circulatory system, the genitourinary system, the gastrointestinal system or the nervous system. In another embodiment, the inflammatory disorder of the musculoskeletal and connective tissue system is selected from the group consisting of arthritis, psoriasis, myocitis, dermatitis and eczema. In still another embodiment, the inflammatory disorder of the respiratory system is selected from the group consisting of asthma, bronchitis, sinusitis, pharyngitis, laryngitis, tracheitis, rhinitis, cystic fibrosis, respiratory infection and acute respiratory distress syndrome. In yet another embodiment, the inflammatory disorder of the circulatory system is selected from the group consisting of vasculitis, haematuria syndrome, artherosclerosis, arteritis, phlebitis, carditis and coronary heart disease. In another embodiment, the inflammatory disorder of the gastrointestinal system is selected from the group consisting of inflammatory bowel disorder, ulcerative colitis, Crohn's disease, diverticulitis, viral infection, bacterial infection, peptic ulcer, chronic hepatitis, gingivitis, periodentitis, stomatitis, gastritis and gastrointestinal reflux disease. In still another embodiment, the inflammatory disorder of the genitourinary system is selected from the group consisting of cystitis, polycystic kidney disease, nephritic syndrome, urinary tract infection, cystinosis, prostatitis, salpingitis, endometriosis and genitourinary cancer.

In another embodiment, the neurological disorder is selected from the group consisting of schizophrenia, bipolar disorder, depression, Alzheimer's disease, epilepsy, multiple sclerosis, amyotrophic lateral sclerosis, stroke, addiction, cerebral ischemia, neuropathy, retinal pigment degeneration, glaucoma, cardiac arrhythmia, shingles, Huntington's chorea, Parkinson disease, anxiety disorders, panic disorders, phobias, anxiety hyteria, generalized anxiety disorder, and neurosis.

In another aspect, the invention provides a method of treating pain in a subject in need thereof, comprising administering to the subject an effective amount of a compound of the invention. In one embodiment, the subject is a mammal. In still another embodiment, the mammal is a human.

In yet another embodiment, the pain is selected from the group consisting of cutaneous pain, somatic pain, visceral pain and neuropathic pain. In another embodiment, the pain is acute pain or chronic pain.

In another aspect, the invention provides a method of treating an inflammatory disorder in a subject in need thereof, comprising administering to the subject an effective amount of a compound of the invention. In one embodiment, the subject is a mammal. In still another embodiment, the mammal is a human.

In yet another embodiment, the inflammatory disorder is an inflammatory disorder of the musculoskeletal and connective tissue system, the respiratory system, the circulatory system, the genitourinary system, the gastrointestinal system or the nervous system.

In another aspect, the invention provides a method of treating a neurological disorder in a subject in need thereof, comprising administering an effective amount of a compound of the invention. In one embodiment, the subject is a mammal. In still another embodiment, the mammal is a human.

In yet another embodiment, the neurological disorder is selected from the group consisting of schizophrenia, bipolar disorder, depression, Alzheimer's disease, epilepsy, multiple sclerosis, amyotrophic lateral sclerosis, stroke, addiction, cerebral ischemia, neuropathy, retinal pigment degeneration, glaucoma, cardiac arrhythmia, shingles, Huntington's chorea, Parkinson disease, anxiety disorders, panic disorders, phobias, anxiety hyteria, generalized anxiety disorder, and neurosis.

In another aspect, the invention provides a method of treating a disease or disorder associated with the genitourinary and/or gastrointestinal systems of a subject in need thereof, comprising administering to the subject an effective amount of a compound of the invention. In another embodiment, the subject is a mammal. In still another embodiment, the mammal is a human.

In yet another embodiment the disease or disorder of the gastrointestinal system is selected from the group consisting of gastritis, duodenitis, irritable bowel syndrome, colitis, Crohn's disease, ulcers and diverticulitis. In another embodiment, the disease or disorder of the genitourinary system is selected from the group consisting of cystitis, urinary tract infections, glomuerulonephritis, polycystic kidney disease, kidney stones and cancers of the genitourinary system.

In another embodiment of the invention, the methods further comprise administering an adjuvant composition. In yet another embodiment, the adjuvant composition is selected from the group consisting of opioid analgesics, non-opioid analgesics, local anesthetics, corticosteroids, non-steroidal anti-inflammatory drugs, non-selective COX inhibitors, non-selective COX2 inhibitors, selective COX2 inhibitors, antiepileptics, barbiturates, antidepressants, marijuana, and topical analgesics.

BRIEF DESCRIPTION OF THE DRAWINGS

FIG. 3 illustrates the inhibitory effect of Compound A on acid-evoked activation of human ASIC1a stably transfected in CHO cells.

FIGS. 7A and 7B show that Compound A and H decrease the rate of the action potential firing induced by pH 6.5 and 6.8, respectively.

FIG. 9 depicts the dose-dependent effect of Compound A on Formalin-induced pain.

FIGS. 10A and 10B illustrate the effects of Compounds B and H, respectively, on spontaneous chemically-induced pain in the formalin test in rats, as described in Example 5. These results indicate that both compounds cause a dose-dependent reduction of the pain intensity as evaluated by the flinching behavior.

DETAILED DESCRIPTION OF THE INVENTION

Figure 1A:
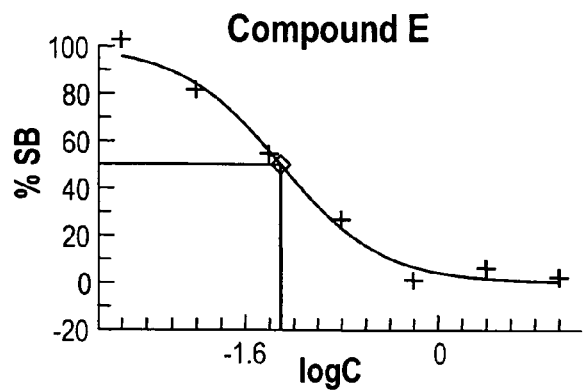
FIGS. 1A, 1B and 1C illustrate dose-response curves of the inhibitory effect of compounds E, F and G on hASIC1a activity as described in Example 1. HEK293 cells were transfected with hASIC1a and cells were exposed to acidic buffer in the absence and presence of increasing concentrations of Compounds E, F or G. Gated-channel activity was determined by measuring intracellular calcium variation using a calcium-selective fluorescent dye. Compounds E, F and G dose-dependently inhibit acid-induced hASIC1a activity.
Figure 1B:
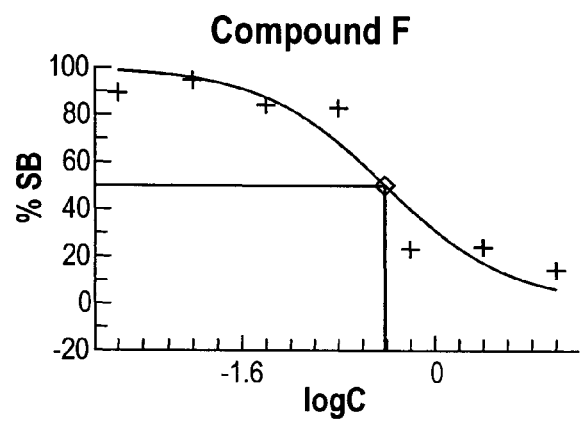
Figure 1C:
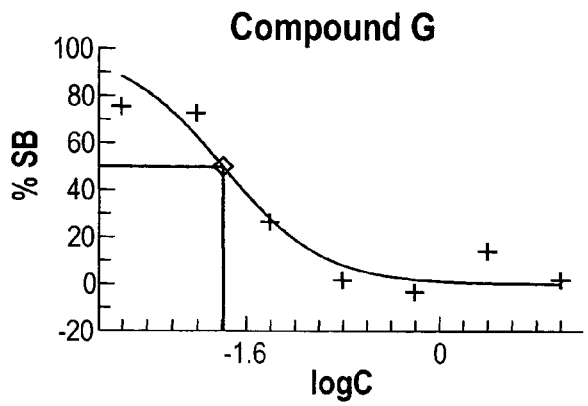

The present invention is based, at least in part, on the identification of compounds useful in modulation of the activity of gated ion channels. Gated ion channels are involved in receiving, conducting, and transmitting signals in a cell (e.g., an electrically excitable cell, for example, a neuronal or muscle cell). Gated ion channels can determine membrane excitability (the ability of, for example, a cell to respond to a stimulus and to convert it into a sensory impulse). Gated ion channels can also influence the resting potential of membranes, wave forms and frequencies of action potentials, and thresholds of excitation. Gated ion channels are typically expressed in electrically excitable cells, e.g., neuronal cells, and are multimeric; they can form homomultimeric (e.g., composed of one type of subunit), or heteromultimeric structures (e.g., composed of more than one type of subunit). Gated ion channels can also be found in nonexcitable cells (e.g., adipose cells or liver cells), where they can play a role in, for example, signal transduction.

Gated ion channels that are the focus of this invention are generally homomeric or heteromeric complexes composed of subunits, comprising at least one subunit belonging to the DEG/ENaC, TRPV and/or P2X gene superfamilies. Non-limiting examples of the DEG/ENaC receptor gene superfamily include epithelial $Na^+$ channels, e.g., $\alpha$ENaC, $\beta$ENaC, $\gamma$ENaC, and/or $\delta$ENaC, and the acid sensing ion channels (ASICs), e.g., ASIC1, ASIC1a, ASIC1b, ASIC2, ASIC2a, ASIC2b, ASIC3, and/or ASIC4. Non-limiting examples of the P2X receptor gene superfamily include $P2X_1$, $P2X_2$, $P2X_3$, $P2X_4$, $P2X_5$, $P2X_6$, and $P2X_7$. Non-limiting examples of the TRPV receptor gene superfamily include TRPV1 (also referred to as VR1), TRPV2 (also referred to as VRL-1), TRPV3 (also referred to as VRL-3), TRPV4 (also referred to as VRL-2), TRPV5 (also referred to as ECAC-1), and/or TRPV6 (also referred to as ECAC-2).

Non limiting examples of heteromultimeric gated ion channels include $\alpha$ENaC, $\beta$ENaC and $\gamma$ENaC; $\alpha$ENaC, $\beta$ENaC and $\delta$ENaC; ASIC1a and ASIC2a; ASIC1a and ASIC2b; ASIC1a and ASIC3; ASIC1b and ASIC3; ASIC2a and ASIC2b; ASIC2a and ASIC3; ASIC2b and ASIC3; ASIC1a, ASIC2a and ASIC3; ASIC3 and P2X, e.g. $P2X_1$, $P2X_2$, $P2X_3$, $P2X_4$, $P2X_5$, $P2X_6$ and $P2X_7$, preferably ASIC3 and $P2X_2$; ASIC3 and $P2X_3$; and ASIC3, $P2X_2$ and $P2X_3$ ASIC4 and at least one of ASIC1a, ASIC1b, ASIC2a, ASIC2b, and ASIC3; BLINaC (or hINaC) and at least one of ASIC1a, ASIC1b, ASIC2a, ASIC2b, ASIC3, and ASIC4; $\delta$ENaC and ASIC, e.g. ASIC1a, ASIC1b, ASIC2a, ASIC2b, ASIC3 and ASIC4; $P2X_1$ and $P2X_2$, $P2X_1$, and $P2X_5$, $P2X_2$ and $P2X_3$, $P2X_2$ and $P2X_6$, $P2X_4$ and $P2\times6$, TRPV1 and TRPV2, TRPV5 and TRPV6, TRPV1 and TRPV4.

Based on the above, there is a need for compositions which modulate the activity of ion channels and methods of use thereof for the treatment of conditions, diseases and disorders related to pain, inflammation, the neurological system, the gastrointestinal system and genitourinary system.

DEFINITIONS

As used herein, the term "acid" refers to carboxylic acid, sulfonic acid, sulfinic acid, sulfamic acid, phosphonic acid and boronic acid functional groups.

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. Furthermore, the expression "$C_x$-$C_y$-alkyl", wherein x is 1-5 and y is 2-10 indicates a particular alkyl group (straight- or branched-chain) of a particular range of carbons. For example, the expression $C_1$-$C_4$-alkyl includes, but is not limited to, methyl, ethyl, propyl, butyl, isopropyl, tert-butyl and isobutyl.

The term alkyl further includes alkyl groups which can further include oxygen, nitrogen, sulfur or phosphorous atoms replacing one or more carbons of the hydrocarbon backbone. In an embodiment, a straight chain or branched chain alkyl has 10 or fewer carbon atoms in its backbone (e.g., $C_1$-$C_{10}$ for straight chain, $C_3$-$C_{10}$ for branched chain), and more preferably 6 or fewer carbons. Likewise, preferred cycloalkyls have from 4-7 carbon atoms in their ring structure, and more preferably have 5 or 6 carbons in the ring structure.

Moreover, alkyl (e.g., methyl, ethyl, propyl, butyl, pentyl, hexyl, etc.) includes both "unsubstituted alkyl" and "substituted alkyl", the latter of which refers to alkyl moieties having substitutents replacing a hydrogen on one or more carbons of the hydrocarbon backbone, which allow the molecule to perform its intended function. The term "substituted" is intended to describe moieties having substitutents replacing a hydrogen on one or more atoms, e.g. C, O or N, of a molecule. Such substitutents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclic, alkylaryl, morpholino, phenol, benzyl, phenyl, piperizine, cyclopentane, cyclohexane, pyridine, 5H-tetrazole, triazole, piperidine, or an aromatic or heteroaromatic moiety.

Further examples of substituents of the invention, which are not intended to be limiting, include moieties selected from straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., $-NH_2$), $(CR'R'')_{0-3}CN$ (e.g., $-CN$), $-NO_2$, halogen (e.g., $-F$, $-Cl$, $-Br$, or $-I$), $(CR'R'')_{0-3}C(halogen)_3$ (e.g., $-CF_3$), $(CR'R'')_{0-3}CH(halogen)_2$, $(CR'R'')_{0-3}$ $CH_2(halogen)$, $(CR'R'')_{0-3}CONR'R''$, $(CR'R'')_{0-3}(CNH)$ $NR'R''$, $(CR'R'')_{0-3}S(O)_{1-2}NR'R''$, $(CR'R'')_{0-3}CHO$, $(CR'R'')_{0-3}(CR'R'')_{0-3}H$, $(CR'R'')_{0-3}S(O)_{0-3}R'$ (e.g., $-SO_3H$, $-OSO_3H$), $(CR'R'')_{0-3}O(CR'R'')_{0-3}H$ (e.g., $-CH_2OCH_3$ and $-OCH_3$), $(CR'R'')_{0-3}S(CR'R'')_{0-3}H$ (e.g., $-SH$ and $-SCH_3$), $(CR'R'')_{0-3}H$ (e.g., $-OH$), $(CR'R'')_{0-3}COR'$, $(CR'R'')_{0-3}$(substituted or unsubstituted phenyl), $(CR'R'')_{0-3}$ $(C_3$-$C_8$ cycloalkyl), $(CR'R'')_{0-3}CO_2R'$ (e.g., $-CO_2H$), or $(CR'R'')_{0-3}OR'$ group, or the side chain of any naturally occurring amino acid; wherein R' and R'' are each independently hydrogen, a $C_1$-$C_5$ alkyl, $C_2$-$C_5$ alkenyl, $C_2$-$C_5$ alkynyl, or aryl group. Such substitutents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, oxime, thiol, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. In certain embodiments, a carbonyl moiety ($C=O$) can be further derivatized with an oxime moiety, e.g., an aldehyde moiety can be derivatized as its oxime ($-C=N-OH$) analog. It will be understood by those skilled in the art that the moieties substituted on the hydrocarbon chain can themselves be substituted, if appropriate. Cycloalkyls can be further substituted, e.g., with the substitutents described above. An "aralkyl" moiety is an alkyl substituted with an aryl (e.g., phenylmethyl (i.e., benzyl)).

The term "amine" or "amino" should be understood as being broadly applied to both a molecule, or a moiety or functional group, as generally understood in the art, and can be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

In a particular embodiment of the invention, the term "amine" or "amino" refers to substituents of the formulas N(R$^8$)R$^9$ or C$_{1-6}$—N(R$^8$)R$^9$, wherein R$^8$ and R$^9$ are each, independently, selected from the group consisting of —H and —(C$_{1-4}$alkyl)$_{0-1}$G, wherein G is selected from the group consisting of —COOH, —H, —PO$_3$H, —SO$_3$H, —Br, —Cl, —F, —O—C$_{1-4}$alkyl, —S—C$_{1-4}$alkyl, aryl, —C(O)OC$_1$-C$_6$-alkyl, —C(O)C$_{1-4}$alkyl-COOH, —C(O)C$_1$-C$_4$-alkyl and —C(O)-aryl; or N(R$^8$)R$^9$ is pyrrolyl, tetrazolyl, pyrrolidinyl, pyrrolidinyl-2-one, dimethylpyrrolyl, imidazolyl and morpholino.

The term "aryl" includes groups, including 5- and 6-membered single-ring aromatic groups that can include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, napthridine, indole, benzofuran, purine, benzofuran, deazapurine, or indolizine. Those aryl groups having heteroatoms in the ring structure can also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

It will be noted that the structures of some of the compounds of this invention include asymmetric carbon atoms. It is to be understood accordingly that the isomers arising from such asymmetry (e.g., all enantiomers and diastereomers) are included within the scope of this invention. Such isomers can be obtained in substantially pure form by classical separation techniques and by stereochemically controlled synthesis. Furthermore, the structures and other compounds and moieties discussed in this application also include all tautomers thereof. Compounds described herein can be obtained through art recognized synthesis strategies.

Additionally, the phrase "any combination thereof" implies that any number of the listed functional groups and molecules can be combined to create a larger molecular architecture. For example, the terms "phenyl," "carbonyl" (or "═O"), "—O—," "—OH," and C$_{1-6}$ (i.e., —CH$_3$ and —CH$_2$CH$_2$CH$_2$—) can be combined to form a 3-methoxy-4-propoxybenzoic acid substitutent. It is to be understood that when combining functional groups and molecules to create a larger molecular architecture, hydrogens can be removed or added, as required to satisfy the valence of each atom.

As used herein, the terms "gated ion channel" or "gated channel" are used interchangeably and are intended to refer to a mammalian (e.g., rat, mouse, human) multimeric complex responsive to, for example, variations of voltage (e.g., membrane depolarization or hyperpolarization), temperature (e.g., higher or lower than 37° C.), pH (e.g., pH values higher or lower than 7.4), ligand concentration and/or mechanical stimulation. Examples of specific modulators include, but are not limited to, endogenous extracellular ligands such as anandamide, ATP, glutamate, cysteine, glycine, gamma-aminobutyric acid (GABA), histidine, serotonin (5HT), acetylcholine, epinephrine, norepinephrine, protons, ions, e.g., Na$^+$, Ca$^{++}$, K$^+$, Cl$^-$, H$^+$, Zn$^+$, and/or peptides, e.g., Met-enkephaline, Leu-enkephaline, dynorphin, neurotrophins, and/or the RFamide related peptides, e.g., FMRFamide and/or FLRFamide; to endogenous intracellular ligands such as cyclic nucleotides (e.g. cyclicAMP, cyclicGMP), ATP, Ca$^{++}$ and/or G-proteins; to exogenous extracellular ligands or modulators such as α-amino-3-hydroxy-5-methyl-4-isolaxone propionate (AMPA), amiloride, capsaicin, capsazepine, epibatidine, cadmium, barium, gadolinium, guanidium, kainate, N-methyl-D-aspartate (NMDA). Gated ion channels also include complexes responsive to toxins, examples of which include, but are not limited to, Agatoxin (e.g. α-agatoxin IVA, IVB, ω-agatoxin IVA, TK), Agitoxins (Agitoxin 2), Apamin, Argiotoxins, Batrachotoxins, Brevetoxins (e.g. Brevetoxin PbTx-2, PbTx-3, PbTx-9), Charybdotoxins, Chlorotoxins, Ciguatoxins, Conotoxins (e.g. α-conotoxin GI, GIA, GII, IMI, MI, MII, SI, SIA, SII, and/or EI; δ-conotoxins, μ-conotoxin GIIIA, GIIIB, GIIIC and/or GS, ω-conotoxin GVIA, MVIIA MVIIC, MVIID, SVIA and/or SVIB), Dendrotoxins, Grammotoxins (GsMTx-4, ω-grammotoxin SIA), Grayanotoxins, Hanatoxins, Iberiotoxins, Imperatoxins, Jorotoxins, Kaliotoxins, Kurtoxins, Leiurotoxin 1, Pricotoxins, Psalmotoxins, (e.g., Psalmotoxin 1 (PcTx1)), Margatoxins, Noxiustoxins, Phrixotoxins, PLTX II, Saxitoxins, Stichodactyla Toxins, sea anemone toxins (e.g. APETx2 from Anthopleura elegantissima), Tetrodotoxins, Tityus toxin K-α, Scyllatoxins and/or tubocurarine.

In a preferred embodiment, the compounds of the invention modulate the activity of ASIC1a and/or ASIC3.

"Gated ion channel-mediated activity" is a biological activity that is normally modulated (e.g., inhibited or promoted), either directly or indirectly, in the presence of a gated ion channel. Gated ion channel-mediated activities include, for example, receiving, integrating, transducing, conducting, and transmitting signals in a cell, e.g., a neuronal or muscle cell. A biological activity that is mediated by a particular gated ion channel, e.g. ASIC1a or ASIC3, is referred to herein by reference to that gated ion channel, e.g. ASIC1a- or ASIC3-mediated activity. To determine the ability of a compound to inhibit a gated ion channel-mediated activity, conventional in vitro and in vivo assays can be used which are described herein.

"Neurotransmission," as used herein, is a process by which small signaling molecules, termed neurotransmitters, are rapidly passed in a regulated fashion from a neuron to another cell. Typically, following depolarization associated with an incoming action potential, a neurotransmitter is secreted from the presynaptic neuronal terminal. The neurotransmitter then diffuses across the synaptic cleft to act on specific receptors on the postsynaptic cell, which is most often a neuron but can also be another cell type (such as muscle fibers at the neuromuscular junction). The action of neurotransmitters can either be excitatory, depolarizing the postsynaptic cell, or inhibitory, resulting in hyperpolarization. Neurotransmission can be rapidly increased or decreased by neuromodulators, which typically act either pre-synaptically or post-synaptically. The gated ion channel ASIC1a has been shown to possibly contribute to neurotransmission [Babini et al., J Biol. Chem. 277(44):41597-603 (2002)].

Examples of gated ion channel-mediated activities include, but are not limited to, pain (e.g., inflammatory pain, acute pain, chronic malignant pain, chronic nonmalignant pain and neuropathic pain), inflammatory disorders, diseases and disorders of the genitourinary and gastrointestinal systems, and neurological disorders (e.g., neurodegenerative or neuropsychiatric disorders).

"Pain" is defined as an unpleasant sensory and emotional experience associated with actual or potential tissue damage, or described in terms of such damage (International Association for the Study of Pain—IASP). Pain is classified most often based on duration (i.e., acute vs. chronic pain) and the underlying pathophysiology (i.e., nociceptive vs. neuropathic pain).

Acute pain can be described as an unpleasant experience with emotional and cognitive, as well as sensory, features that occur in response to tissue trauma and disease and serves as a defensive mechanism. Acute pain is usually accompanied by a pathology (e.g., trauma, surgery, labor, medical procedures, acute disease states) and the pain resolves with healing of the underlying injury. Acute pain is mainly nociceptive, but can also be neuropathic.

Chronic pain is pain that extends beyond the period of healing, with levels of identified pathology that often are low and insufficient to explain the presence, intensity and/or extent of the pain (American Pain Society—APS). Unlike acute pain, chronic pain serves no adaptive purpose. Chronic pain can be nociceptive, neuropathic, or both and caused by injury (e.g., trauma or surgery), malignant conditions, or a variety of chronic conditions (e.g., arthritis, fibromyalgia and neuropathy). In some cases, chronic pain exists de novo with no apparent cause.

"Nociceptive pain" is pain that results from damage to tissues and organs. Nociceptive pain is caused by the ongoing activation of pain receptors in either the superficial or deep tissues of the body. Nociceptive pain is further characterized as "somatic pain", including "cutaneous pain" and "deep somatic pain", and "visceral pain".

"Somatic pain" includes "cutaneous pain" and "deep somatic pain." Cutaneous pain is caused by injury, diseases and disorders of the skin and related organs. Examples of conditions associated with cutaneous pain include, but are not limited to, cuts, burns, infections, lacerations, as well as traumatic injury and post-operative or surgical pain (e.g., at the site of incision).

"Deep somatic pain" results from injuries, diseases or disorders of the musculoskeletal tissues, including ligaments, tendons, bones, blood vessels and connective tissues. Examples of deep somatic pain or conditions associated with deep somatic pain include, but are not limited to, sprains, broken bones, arthralgia, vasculitis, myalgia and myofascial pain. Arthralgia refers to pain caused by a joint that has been injured (such as a contusion, break or dislocation) and/or inflamed (e.g., arthritis). Vaculitis refers to inflammation of blood vessels with pain. Myalgia refers to pain originating from the muscles. Myofascial pain refers to pain stemming from injury or inflammation of the fascia and/or muscles.

"Visceral" pain is associated with injury, inflammation or disease of the body organs and internal cavities, including but not limited to, the circulatory system, respiratory system, gastrointestinal system, genitourinary system, immune system, as well as ear, nose and throat. Visceral pain can also be associated with infectious and parasitic diseases that affect the body organs and tissues. Visceral pain is extremely difficult to localize, and several injuries to visceral tissue exhibit "referred" pain, where the sensation is localized to an area completely unrelated to the site of injury. For example, myocardial ischaemia (the loss of blood flow to a part of the heart muscle tissue) is possibly the best known example of referred pain; the sensation can occur in the upper chest as a restricted feeling, or as an ache in the left shoulder, arm or even hand. Phantom limb pain is the sensation of pain from a limb that one no longer has or no longer gets physical signals from—an experience almost universally reported by amputees and quadriplegics.

"Neuropathic pain" or "neurogenic pain" is pain initiated or caused by a primary lesion, dysfunction or perturbation in the nervous system. "Neuropathic pain" can occur as a result of trauma, inflammation or disease of the peripheral nervous system ("peripheral neuropathic pain") and the central nervous system ("central pain"). For example, neuropathic pain can be caused by a nerve or nerves that are irritated, trapped, pinched, severed or inflamed (neuritis). There are many neuropathic pain syndromes, such as diabetic neuropathy, trigeminal neuralgia, postherpetic neuralgia ("shingles"), post-stroke pain, and complex regional pain syndromes (also called reflex sympathetic dystrophy or "RSD" and causalgia).

As used herein, the term "inflammatory disease or disorder" includes diseases or disorders which are caused, at least in part, or exacerbated by, inflammation, which is generally characterized by increased blood flow, edema, activation of immune cells (e.g., proliferation, cytokine production, or enhanced phagocytosis), heat, redness, swelling, pain and loss of function in the affected tissue and organ. The cause of inflammation can be due to physical damage, chemical substances, micro-organisms, tissue necrosis, cancer or other agents. Inflammatory disorders include acute inflammatory disorders, chronic inflammatory disorders, and recurrent inflammatory disorders. Acute inflammatory disorders are generally of relatively short duration, and last for from about a few minutes to about one to two days, although they can last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or longer, and are associated histologically with the presence of lymphocytes and macrophages and with proliferation of blood vessels and connective tissue. Recurrent inflammatory disorders include disorders which recur after a period of time or which have periodic episodes. Some disorders can fall within one or more categories.

The terms "neurological disorder" and "neurodegenerative disorder" refer to injuries, diseases and dysfunctions of the nervous system, including the peripheral nervous system and central nervous system. Neurological disorders and neurodegenerative disorders include, but are not limited to, diseases and disorders that are associated with gated ion channel-mediated biological activity. Examples of neurological disorders include, but are not limited to, Alzheimer's disease, epilepsy, cancer, neuromuscular diseases, multiple sclerosis, amyotrophic lateral sclerosis, stroke, cerebral ischemia, neuropathy (e.g., chemotherapy-induced neuropathy, diabetic neuropathy), retinal pigment degeneration, Huntington's chorea, and Parkinson's disease, anxiety disorders (e.g., phobic disorders (e.g., agoraphobia, claustrophobia), panic disorders, phobias, anxiety hyteria, generalized anxiety disorder, and neurosis), and ataxia-telangiectasia.

As used herein, "neuropathy" is defined as a failure of the nerves that carry information to and from the brain and spinal cord resulting in one or more of pain, loss of sensation, and inability to control muscles. In some cases, the failure of nerves that control blood vessels, intestines, and other organs results in abnormal blood pressure, digestion problems, and loss of other basic body processes. Peripheral neuropathy can involve damage to a single nerve or nerve group (mononeuropathy) or can affect multiple nerves (polyneuropathy).

The term "treated," "treating" or "treatment" includes the diminishment or alleviation of at least one symptom associated with the pain, inflammatory disorder, neurological disorder, genitourinary disorder or gastrointestinal disorder (e.g., a symptom associated with or caused by gated ion channel mediated activity) being treated. In certain embodiments, the treatment comprises the modulation of the interaction of a gated ion channel (e.g., ASIC1a and/or ASIC3) by a gated ion channel modulating compound, which would in turn diminish or alleviate at least one symptom associated with or caused by the gated ion channel-mediated activity being treated. For example, treatment can be diminishment of one or several symptoms of a disorder or complete eradication of a disorder.

As used herein, the phrase "therapeutically effective amount" of the compound is the amount necessary or sufficient to treat or prevent pain, an inflammatory disorder, a neurological disorder, a gastrointestinal disorder or a genitourinary disorder, (e.g., to prevent the various symptoms of a gated ion channel-mediated activity). In an example, an effective amount of the compound is the amount sufficient to alleviate at least one symptom of the disorder, e.g., pain, inflammation, a neurological disorder, a gastrointestinal disorder or a genitourinary disorder, in a subject.

The term "subject" is intended to include animals, which are capable of suffering from or afflicted with a gated ion channel-associated state or gated ion channel-associated disorder, or any disorder involving, directly or indirectly, gated ion channel activity. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from pain, inflammation, a neurological disorder, a gastrointestinal disorder or a genitourinary disorder (e.g. associated with gated channel-associated activity).

The language "gated ion channel modulator" refers to compounds that modulate, i.e., inhibit, promote or otherwise alter the activity of a gated ion channel. For example, the gated ion channel modulator can inhibit, promote or otherwise alter the response of a gated ion channel to, for example, variations of voltage (e.g., membrane depolarization or hyperpolarization), temperature (e.g., higher or lower than 37° C.), pH (e.g., pH values higher or lower than 7.4), ligand concentration and/or mechanical stimulation. Examples of gated ion channel modulators include compounds of the invention (i.e., Formulas 1, 2, 3, 4 and 5, as well as compounds A, B, C, D, E, F, G, H, I, J and K) including salts thereof, e.g., a pharmaceutically acceptable salt. In a particular embodiment, the gated ion channel modulators of the invention can be used to treat a disease or disorder associated with pain, inflammation, neurological disorders, gastrointestinal disorders or genitourinary disorders in a subject in need thereof. In another embodiment, the compounds of the invention can be used to treat an inflammatory disorder in a subject in need thereof.

Modulators of Ion Channel Activity

The present invention provides compounds which modulate the activity of a gated ion channel. In some embodiments, the compounds of the invention modulate the activity of a gated ion channel comprised of at least one subunit belonging to the DEG/ENaC, TRPV and/or P2X gene superfamilies. In some embodiments, the compounds of the invention modulate the activity of the gated ion channel comprised of at least one subunit selected from the group consisting of αENaC, βENaC, γENaC, δENaC, ASIC1a, ASIC1b, ASIC2a, ASIC2b, ASIC3, ASIC4, BLINaC, hINaC, $P2X_1$, $P2X_2$, $P2X_3$, $P2X_4$, $P2X_5$, $P2X_6$, $P2X_7$, TRPV1, TRPV2, TRPV3, TRPV4, TRPV5, and TRPV6. In still other embodiments, the compounds of the invention modulate the activity of the DEG/ENaC gated ion channel comprised of at least one subunit selected from the group consisting of αENaC, βENaC, γENaC, δENaC, BLINaC, hINaC, ASIC1a, ASIC1b, ASIC2a, ASIC2b, ASIC3, and ASIC4. In certain embodiments, the compounds of the invention modulate the activity of the DEG/ENaC gated ion channel comprised of at least one subunit selected from the group consisting of ASIC1a, ASIC1b, ASIC2a, ASIC2b, ASIC3, and ASIC4. In certain embodiments, the compounds of the invention modulate the activity of the DEG/ENaC gated ion channel comprised of at least two subunits selected from the group consisting of ASIC1a, ASIC1b, ASIC2a, ASIC2b, ASIC3, and ASIC4. In yet other embodiments, the compounds of the invention modulate the activity of the DEG/ENaC gated ion channel comprised of at least three subunits selected from the group consisting of ASIC1a, ASIC1b, ASIC2a, ASIC2b, ASIC3, and ASIC4. In certain embodiments, the compounds of the invention modulate the activity of a gated ion channel comprised of ASIC, i.e., ASIC1a or ASIC1b. In certain embodiments, the compounds of the invention modulate the activity of a gated ion channel comprised of ASIC3. In certain embodiments, the compounds of the invention modulate the activity of a gated ion channel comprised of ASIC1a and ASIC2a; ASIC1a and ASIC3; ASIC1b and ASIC3; ASIC2a and ASIC2b; ASIC2a and ASIC3; ASIC2b and ASIC3; and ASIC1a, ASIC2a and ASIC3. In other embodiments, the compounds of the invention modulate the activity of the P2X gated ion channel comprised of at least one subunit selected from the group consisting of $P2X_1$, $P2X_2$, $P2X_3$, $P2X_4$, $P2X_5$, $P2X_6$, and $P2X_7$. In certain embodiments, the compounds of the invention modulate the activity of a gated ion channel comprised of $P2X_2$, $P2X_3$ or $P2X_4$. In certain embodiments, the compounds of the invention modulate the activity of a gated ion channel comprised of $P2X_1$ and $P2X_2$, $P2X_1$ and $P2X_5$, $P2X_2$ and $P2X_3$, $P2X_2$ and $P2X_6$, and $P2X_4$ and $P2X_6$. In yet another aspect of the invention, the compounds of the invention modulate the activity of the TRPV gated ion channel comprised of at least one subunit selected from the group TRPV1, TRPV2, TRPV3, TRPV4, TRPV5, and TRPV6. In certain embodiments, the compounds of the invention modulate the activity of a gated ion channel comprised of TRPV1 or TRPV2. In certain embodiments, the compounds of the invention modulate the activity of a gated ion channel comprised of TRPV1 and TRPV2, TRPV1 and TRPV4, and TRPV5 and TRPV6.

In a particular embodiment, the compounds of the invention modulate the activity of ASIC1a and/or ASIC3.

The nomenclature of the compounds of the present invention follows standard conventions. The "southern" phenyl ring is numbered as indicated below:

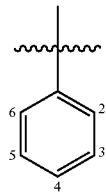

In one aspect, the compound that modulates the activity of a gated ion channel is of the Formula 1,

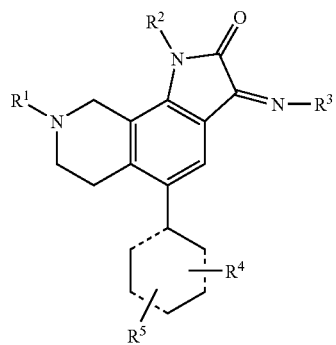

(1)

and pharmaceutically acceptable salts, enantiomers, stereoisomers, rotamers, tautomers, diastereomers, or racemates thereof;

wherein the dashed lines indicate a single or double bond; $R^1$ is selected from the group consisting of hydrogen, alkyl, alkoxy-alkyl, hydroxy-alkyl, alkoxy-carbonyl-alkyl, alkyl-carbonyl-oxy-alkyl, cycloalkyl, cycloalkyl-alkyl, alkenyl, alkynyl, alkoxy, sulfonamide, amino, sulfonyl, sulfonic acid, urea, phenyl or benzyl, in which the phenyl or benzyl group is optionally substituted with halogen, $CF_3$, nitro, amino, cyano, hydroxy-alkyl, alkoxy, sulfonamide, alkenyl, alkynyl, amino, sulfonyl, sulfonic acid and urea; $R^2$ is selected from the group consisting of hydrogen, hydroxyl, alkyl, alkenyl, alkynyl, —$(CH_2)_{1-4}S(O)_3H$, —$C(O)C_{1-4}$alkyl and —$S(O)_2C_{1-4}$alkyl; $R^3$ is selected from the group consisting of hydrogen, hydroxyl, alkyl, acyl, phenyl, benzyl, —COOH, —C(O)N(CH_3)_2$, —O-phenyl, —$OCF_3$, alkoxy, —$O(CH_2)_{0-4}CH_3$, —C(O)H, —$C(O)CH_3$,

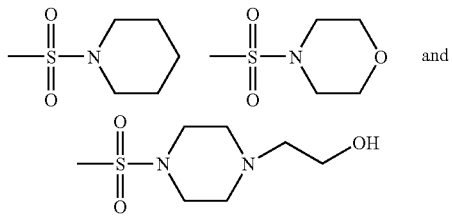

and $R^4$ and $R^5$ are each, independently, selected from the group consisting of halogen, $CF_3$, nitro, amino, cyano, hydroxyl, alkyl, alkoxy, phenoxy and phenyl, or a group of the formula —$SO_2NR'R''$, wherein R' and R" independently of each another represents hydrogen or alkyl.

In one embodiment of Formula 1, $R^1$ is selected from the group consisting of hydrogen, alkyl, alkenyl, and alkynyl; $R^2$ is selected from the group consisting of hydrogen, hydroxyl, alkyl, alkenyl and alkynyl; $R^3$ is selected from the group consisting of hydrogen, hydroxyl, alkyl, acyl, phenyl, benzyl, and —COOH; and $R^4$ and $R^5$ are each, independently, selected from the group consisting of halogen, $CF_3$, nitro, amino, cyano, hydroxyl, alkyl, alkoxy, phenoxy and phenyl.

In another embodiment of Formula 1, $R^1$ is selected from the group consisting of hydrogen and alkyl; $R^2$ is selected from the group consisting of hydrogen, hydroxyl, alkyl, alkenyl and alkynyl; $R^3$ is selected from the group consisting of hydrogen, hydroxyl, alkoxy and alkyl; and $R^4$ and $R^5$ are each, independently, selected from the group consisting of halogen, $CF_3$, alkyl, phenoxy and alkoxy.

In yet another embodiment of Formula 1, the dashed lines indicate a double bond; $R^1$ is selected from the group consisting of alkyl; $R^2$ is selected from the group consisting of hydrogen and alkyl; $R^3$ is hydroxyl; and $R^4$ and $R^5$ are each, independently, selected from the group consisting of halogen, $CF_3$, alkyl, phenoxy and alkoxy.

A preferred embodiment of Formula 1 is represented as Formula 2,

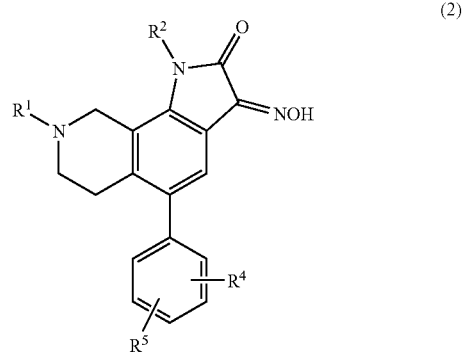

(2)

and pharmaceutically acceptable salts, enantiomers, stereoisomers, rotamers, tautomers, diastereomers, or racemates thereof;

wherein $R^1$ is selected from the group consisting of hydrogen, alkyl, alkoxy-alkyl, alkoxy-carbonyl-alkyl, alkyl-carbonyl-oxy-alkyl, cycloalkyl, cycloalkyl-alkyl, alkenyl, alkynyl, alkoxy, sulfonamide, amino, sulfonyl, sulfonic acid, urea, phenyl or benzyl, in which the phenyl or benzyl group is optionally substituted with halogen, $CF_3$, nitro, amino, cyano, hydroxy-alkyl, alkoxy, sulfonamide, alkenyl, alkynyl, amino, sulfonyl, sulfonic acid and urea; $R^2$ is selected from the group consisting of hydrogen, hydroxyl, alkyl, alkenyl, alkynyl, —$(CH_2)_{1-4}S(O)_3H$, —$C(O)C_4$alkyl and —$S(O)_2C_{1-4}$ alkyl; and $R^4$ and $R^5$ are each, independently, selected from the group consisting of halogen, $CF_3$, nitro, amino, cyano, hydroxyl, alkyl, alkoxy, phenoxy and phenyl, or a group of the formula —$SO_2NR'R''$, wherein R' and R'' independently of each another represents hydrogen or alkyl.

In one embodiment of Formula 2, $R^1$ is selected from the group consisting of hydrogen, alkyl, alkenyl, and alkynyl; $R^2$ is selected from the group consisting of hydrogen, hydroxyl, alkyl, alkenyl and alkynyl; and $R^4$ and $R^5$ are each, independently, selected from the group consisting of halogen, $CF_3$, nitro, amino, cyano, hydroxyl, alkyl, alkoxy, phenoxy and phenyl.

In yet another embodiment of Formula 2, $R^1$ is selected from the group consisting of hydrogen and alkyl; $R^2$ is selected from the group consisting of hydrogen, hydroxyl, alkyl, alkenyl and alkynyl; and $R^4$ and $R^5$ are each, independently, selected from the group consisting of halogen, $CF_3$, alkyl, phenoxy and alkoxy.

In still another embodiment of Formula 2, $R^1$ is selected from the group consisting of alkyl; $R^2$ is selected from the group consisting of hydrogen and alkyl; and $R^4$ and $R^5$ are each, independently, selected from the group consisting of halogen, $CF_3$, alkyl, phenoxy and alkoxy.

In one embodiment of Formula 2, $R^1$ is selected from the group consisting of hydrogen, $C_{1-4}$-alkyl, $C_{1-4}$-alkenyl, and $C_{1-4}$-alkynyl; $R^2$ is selected from the group consisting of hydrogen, hydroxyl, $C_{1-4}$-alkyl, $C_{1-4}$-alkenyl and $C_{1-4}$-alkynyl; and $R^4$ and $R^5$ are each, independently, selected from the group consisting of halogen, $CF_3$, nitro, amino, cyano, hydroxyl, $C_{1-4}$-alkyl, $C_{1-4}$-alkoxy, phenoxy and phenyl.

In yet another embodiment of Formula 2, $R^1$ is selected from the group consisting of hydrogen and $C_{1-4}$-alkyl; $R^2$ is selected from the group consisting of hydrogen, hydroxyl, $C_{1-4}$-alkyl, $C_{1-4}$-alkenyl and $C_{1-4}$-alkynyl; and $R^4$ and $R^5$ are each, independently, selected from the group consisting of halogen, $CF_3$, $C_{1-4}$-alkyl, phenoxy and $C_{1-4}$-alkoxy.

In still another embodiment of Formula 2, $R^1$ is selected from the group consisting of $C_{1-4}$-alkyl; $R^2$ is selected from the group consisting of hydrogen and $C_{1-4}$-alkyl; and $R^4$ and $R^5$ are each, independently, selected from the group consisting of halogen, $CF_3$, $C_{1-4}$-alkyl, phenoxy and $C_{1-4}$-alkoxy.

In another embodiment of Formula 2, $R^1$ is selected from the group consisting of —$CH_3$ and —$CH_2CH_3$; $R^2$ is selected from the group consisting of hydrogen; and $R^4$ and $R^5$ are each, independently, selected from the group consisting of halogen, alkyl and alkoxy.

In another embodiment of Formula 2, $R^1$ is selected from the group consisting of —$CH_3$ and —$CH_2CH_3$; $R^2$ is selected from the group consisting of hydrogen; and $R^4$ and $R^5$ are each, independently, selected from the group consisting of halogen, $C_{1-4}$-alkyl and $C_{1-4}$-alkoxy.

In another embodiment of Formula 2, $R^1$ is $CH_3$ or $CH_2CH_3$.

In yet another embodiment of Formula 2, $R^2$ is H.

In still another embodiment of Formula 2, $R^4$ is halogen.

In another embodiment of Formula 2, $R^5$ is alkoxy.

In yet another embodiment of Formula 2, $R^4$ is fluoro or chloro.

In another embodiment of Formula 2, $R^5$ is —$OCH_3$.

In still another embodiment of Formula 2, $R^4$ and $R^5$ are both alkyl.

In another embodiment of Formula 2, $R^4$ and $R^5$ are both $CH_3$.

Another preferred embodiment of Formula 1 is represented as Formula 3,

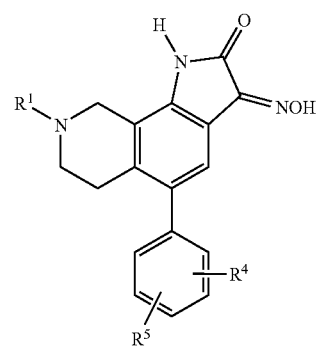

(3)

and pharmaceutically acceptable salts, enantiomers, stereoisomers, rotamers, tautomers, diastereomers, or racemates thereof;

wherein $R^1$ is selected from the group consisting of hydrogen, alkyl, alkoxy-alkyl, alkoxy-carbonyl-alkyl, alkyl-carbonyl-oxy-alkyl, cycloalkyl, cycloalkyl-alkyl, alkenyl, alkynyl, alkoxy, sulfonamide, amino, sulfonyl, sulfonic acid, urea phenyl or benzyl, in which the phenyl or benzyl group is optionally substituted with halogen, $CF_3$, nitro, amino, cyano, hydroxy-alkyl, alkoxy, sulfonamide, alkenyl, alkynyl, amino, sulfonyl, sulfonic acid and urea; and $R^4$ and $R^5$ are each, independently, selected from the group consisting of halogen, phenoxy, $CF_3$, nitro, amino, cyano, hydroxyl, alkyl, alkoxy and phenyl, or a group of the formula —$SO_2NR'R''$, wherein R' and R'' independently of each another represents hydrogen or alkyl.

In a preferred embodiment of Formula 3, $R^5$ is in the 2 position of the aryl ring and $R^4$ is in the 5 position of the aryl ring, or $R^4$ is in the 3 position of the aryl ring and $R^5$ is in the 5 position of the aryl ring.

In one embodiment of Formula 3, $R^1$ is selected from the group consisting of hydrogen, alkyl, alkenyl, and alkynyl; and $R^4$ and $R^5$ are each, independently, selected from the group consisting of halogen, $CF_3$, nitro, amino, cyano, hydroxyl, alkyl, alkoxy, phenoxy and phenyl.

In another embodiment of Formula 3, $R^1$ is selected from the group consisting of hydrogen and alkyl; and $R^4$ and $R^5$ are each, independently, selected from the group consisting of halogen, $CF_3$, alkyl, phenoxy and alkoxy.

In yet another embodiment of Formula 3, $R^1$ is selected from the group consisting of alkyl; and $R^4$ and $R^5$ are each, independently, selected from the group consisting of halogen, $CF_3$, alkyl, phenoxy and alkoxy.

In still another embodiment of Formula 3, $R^1$ is selected from the group consisting of —$CH_3$ and —$CH_2CH_3$; and $R^4$ and $R^5$ are each, independently, selected from the group consisting of halogen, phenoxy and alkoxy.

In one embodiment of Formula 3, $R^1$ is selected from the group consisting of hydrogen, $C_{1-4}$-alkyl, $C_{1-4}$-alkenyl, and $C_{1-4}$-alkynyl; and $R^4$ and $R^5$ are each, independently, selected from the group consisting of halogen, $CF_3$, nitro, amino, cyano, hydroxyl, $C_{1-4}$-alkyl, $C_{1-4}$-alkoxy, phenoxy and phenyl.

In another embodiment of Formula 3, $R^1$ is selected from the group consisting of hydrogen and $C_{1-4}$-alkyl; and $R^4$ and $R^5$ are each, independently, selected from the group consisting of halogen, $CF_3$, $C_{1-4}$-alkyl, phenoxy and $C_{1-4}$-alkoxy.

In yet another embodiment of Formula 3, $R^1$ is selected from the group consisting of $C_{1-4}$-alkyl; and $R^4$ and $R^5$ are each, independently, selected from the group consisting of halogen, $CF_3$, $C_{1-4}$-alkyl, phenoxy and $C_{1-4}$-alkoxy.

In still another embodiment of Formula 3, $R^1$ is selected from the group consisting of —$CH_3$ and —$CH_2CH_3$; and $R^4$ and $R^5$ are each, independently, selected from the group consisting of halogen, phenoxy and $C_{1-4}$-alkoxy.

In another embodiment of Formula 3, $R^1$ is $CH_3$ or $CH_2CH_3$.

In still another embodiment of Formula 3, $R^4$ is halogen.

In yet another embodiment of Formula 3, $R^5$ is alkoxy.

In another embodiment of Formula 3, $R^4$ is fluoro or chloro.

In another embodiment of Formula 3, $R^5$ is —$OCH_3$.

In still another embodiment of Formula 3, $R^4$ and $R^5$ are both alkyl.

In another embodiment of Formula 4, $R^4$ and $R^5$ are both $CH_3$.

Another preferred embodiment of Formula 1 is represented as Formula 4,

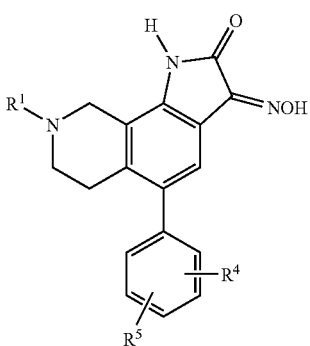

(4)

and pharmaceutically acceptable salts, enantiomers, stereoisomers, rotamers, tautomers, diastereomers, or racemates thereof;

wherein $R^1$ is selected from the group consisting of —$CH_3$ and —$CH_2CH_3$; and $R^4$ and $R^5$ are each, independently, selected from the group consisting of halogen, $CF_3$, alkyl, and alkoxy.

In a preferred embodiment of Formula 4, $R^5$ is in the 2 position of the aryl ring and $R^4$ is in the 5 position of the aryl ring, or $R^4$ is in the 3 position of the aryl ring and $R^5$ is in the 5 position of the aryl ring.

In another preferred embodiment of Formula 4, $R^1$ is selected from the group consisting of —$CH_3$ and —$CH_2CH_3$; and $R^4$ and $R^5$ are each, independently, selected from the group consisting of halogen, $CF_3$, $C_{1-4}$-alkyl, and $C_{1-4}$-alkoxy.

In one embodiment of Formula 4, $R^4$ and $R^5$ are each, independently, selected from the group consisting of halogen, alkyl and alkoxy. In another embodiment of Formula 4, $R^4$ and $R^5$ are each, independently, selected from the group consisting of halogen, $C_{1-4}$-alkyl and $C_{1-4}$-alkoxy.

In another embodiment of Formula 4, $R^4$ is fluoro, and $R^5$ is —$OCH_3$, $R^4$ is chloro, and $R^5$ is —$OCH_3$, or $R^4$ and $R^5$ are both $CH_3$.

A preferred embodiment of Formula 4 is 5-(5-fluoro-2-methoxyphenyl)-6,7,8,9-tetrahydro-3-(hydroxyimino)-8-methyl-1H-pyrrolo[3,2-h]isoquinoline-2(3H)-one (Compound A):

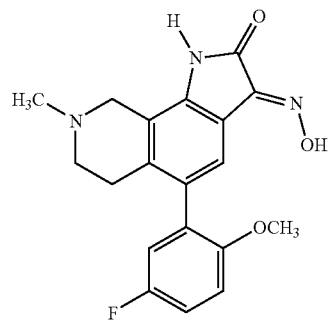

and pharmaceutically acceptable salts thereof.

Another preferred embodiment of Formula 4 is 5-(5-fluoro-2-methoxyphenyl)-6,7,8,9-tetrahydro-3-(hydroxyimino)-8-ethyl-1H-pyrrolo[3,2-h]isoquinoline-2(3H)-one (Compound B):

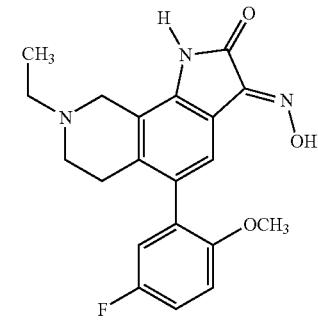

and pharmaceutically acceptable salts thereof.

Another preferred embodiment of Formula 4 is 5-(5-chloro-2-methoxyphenyl)-6,7,8,9-tetrahydro-3-(hydroxyimino)-8-methyl-1H-pyrrolo[3,2-h]isoquinoline-2(3H)-one (Compound C):

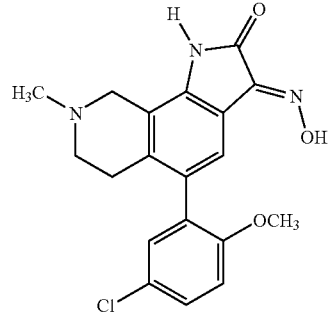

and pharmaceutically acceptable salts thereof.

Another preferred embodiment of Formula 4 is 5-(3,5-dimethylphenyl)-6,7,8,9-tetrahydro-3-(hydroxyimino)-8-methyl-1H-pyrrolo[3,2-h]isoquinoline-2(3H)-one (Compound D):

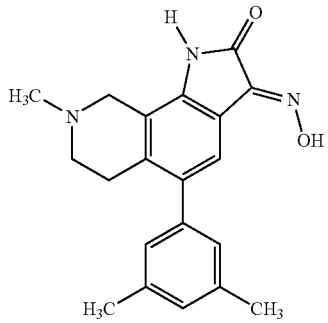

and pharmaceutically acceptable salts thereof.

Another preferred embodiment of Formula 4 is 5-(3,5-dimethylphenyl)-6,7,8,9-tetrahydro-3-(hydroxyimino)-8-ethyl-1H-pyrrolo[3,2-h]isoquinoline-2(3H)-one (Compound E):

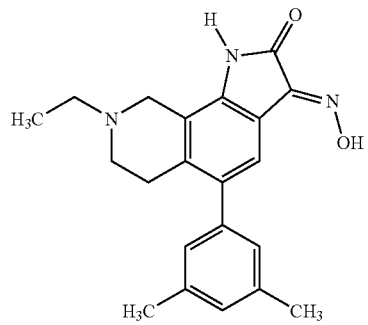

and pharmaceutically acceptable salts thereof.

Another preferred embodiment of Formula 4 is 5-(2,5-dimethylphenyl)-6,7,8,9-tetrahydro-3-(hydroxyimino)-8-ethyl-1H-pyrrolo[3,2-h]isoquinoline-2(3H)-one (Compound F):

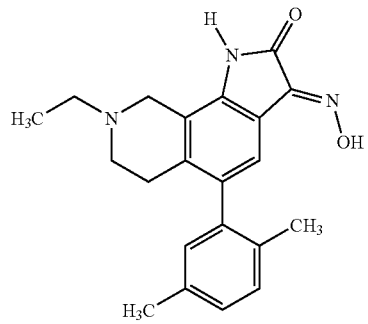

and pharmaceutically acceptable salts thereof.

Another preferred embodiment of Formula 4 is 5-(5-chloro-2-methoxyphenyl)-6,7,8,9-tetrahydro-3-(hydroxyimino)-8-ethyl-1H-pyrrolo[3,2-h]isoquinoline-2(3H)-one (Compound G):

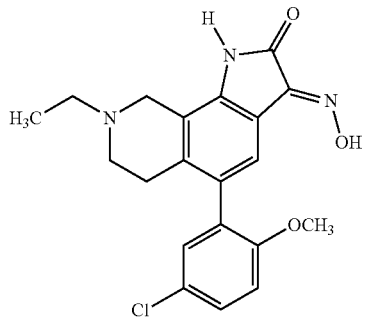

and pharmaceutically acceptable salts thereof.

Another preferred embodiment of Formula 4 is 5-(2,3-dimethyl-phenyl)-8-ethyl-6,7,8,9-tetrahydro-1H-pyrrolo[3,2-h]iso quinoline-2,3-dione 3-oxime (Compound I):

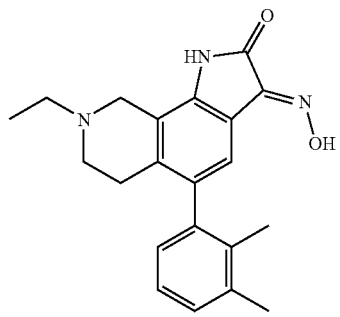

and pharmaceutically acceptable salts thereof.

In another aspect, the compound of the invention is of the Formula 5, (5)

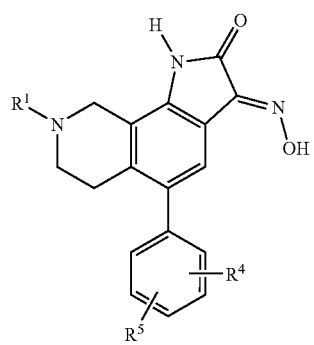

and pharmaceutically acceptable salts, enantiomers, stereoisomers, rotamers, tautomers, diastereomers, or racemates thereof;

wherein $R^1$ is selected from the group consisting of hydrogen, $C_{1-4}$-alkyl, $C_{1-4}$-alkoxy-$C_{1-4}$-alkyl, $C_{1-4}$-alkoxy-carbonyl-$C_{1-4}$-alkyl, $C_{1-4}$-alkyl-carbonyl-oxy-$C_{1-4}$-alkyl, $C_{3-6}$-cycloalkyl, $C_{3-6}$-cycloalkyl-$C_{1-4}$-alkyl, $C_{1-4}$-alkenyl, $C_{1-4}$-alkynyl, $C_{1-4}$-alkoxy, sulfonamide, amino, sulfonyl, sulfonic acid, urea, phenyl or benzyl, in which the phenyl or benzyl group is optionally substituted with halogen, $CF_3$, nitro, amino, cyano, hydroxy-$C_{1-4}$-alkyl, $C_{1-4}$-alkoxy, sulfonamide, $C_{1-4}$-alkenyl, $C_{1-4}$-alkynyl, amino, sulfonyl, sulfonic acid and urea; and $R^4$ and $R^5$ are each, independently, selected from the group consisting of hydrogen, halogen, phenoxy, $CF_3$, nitro, amino, cyano, hydroxyl, $C_{1-4}$-alkyl, $C_{1-4}$-alkoxy and phenyl, or a group of the formula —$SO_2NR'R''$, wherein R' and R'' independently of each another represents hydrogen or $C_{1-4}$-alkyl.

In a preferred embodiment of Formula 5, $R^5$ is in the 3 position of the aryl ring and $R^4$ is in the 2 position of the aryl ring, or $R^4$ is in the 2 position of the aryl ring and $R^5$ is hydrogen.

In one embodiment of Formula 5, $R^1$ is selected from the group consisting of hydrogen, $C_{1-4}$-alkyl, $C_{1-4}$-alkenyl, and $C_{1-4}$-alkynyl; and $R^4$ and $R^5$ are each, independently, selected from the group consisting of hydrogen, halogen, $CF_3$, nitro, amino, cyano, hydroxyl, $C_{1-4}$-alkyl, $C_{1-4}$-alkoxy, phenoxy and phenyl.

In another embodiment of Formula 5, $R^1$ is selected from the group consisting of hydrogen and $C_{1-4}$-alkyl; and $R^4$ and $R^5$ are each, independently, selected from the group consisting of hydrogen, halogen, $CF_3$, $C_{1-4}$-alkyl, phenoxy and $C_{1-4}$-alkoxy.

In another embodiment of Formula 5, $R^4$ is $C_{1-4}$-alkoxy and $R^5$ is hydrogen.

In still another embodiment of Formula 5, $R^1$ is selected from the group consisting of —$CH_3$ and —$CH_2CH_3$; and $R^4$ and $R^5$ are each, independently, selected from the group consisting of hydrogen, $CH_3$, $OCH_3$ and OEt.

A preferred embodiment of Formula 5 is 5-phenyl-6,7,8,9-tetrahydro-3-(hydroxyimino)-8-ethyl-1H-pyrrolo[3,2-h]isoquinoline-2(3H)-one (Compound H):

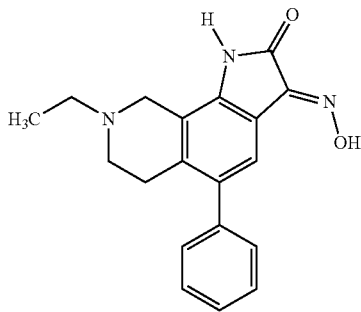

and pharmaceutically acceptable salts thereof.

Another preferred embodiment of Formula 5 is 8-ethyl-5-(2-methoxy-phenyl)-6,7,8,9-tetrahydro-1H-pyrrolo[3,2-h]isoquinoline-2,3-dione 3-oxime (Compound J):

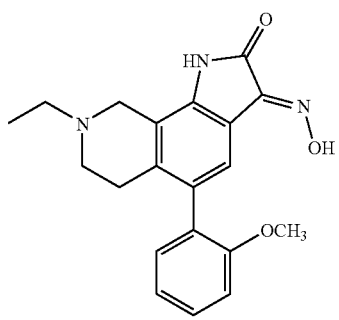

and pharmaceutically acceptable salts thereof.

Another preferred embodiment of Formula 5 is 5-(2-ethoxy-phenyl)-8-ethyl-6,7,8,9-tetrahydro-1H-pyrrolo[3,2-h]isoquinoline-2,3-dione 3-oxime (Compound K):

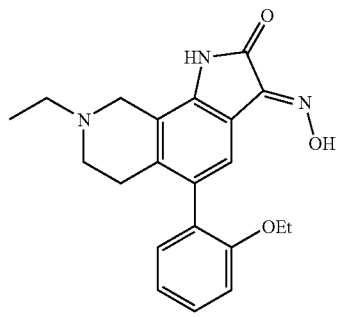

and pharmaceutically acceptable salts thereof.

It is to be understood that all of the compounds of Formulas 1, 2, 3, 4 and 5 described above will further include double bonds between adjacent atoms as required to satisfy the valence of each atom. That is, double bonds are added to provide the following number of total bonds to each of the following types of atoms: carbon: four bonds; nitrogen: three bonds; oxygen: two bonds; and sulfur: two or six bonds.

It will be noted that the structures of some of the compounds of this invention include asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof. Compounds described herein can be obtained though art recognized synthesis strategies.

In one embodiment of the invention, the compounds of the invention that modulate the activity of a gated ion channel are capable of chemically interacting with a gated ion channel, including αENaC, βENaC, γENaC, δENaC, ASIC1a, ASIC1b, ASIC2a, ASIC2b, ASIC3, ASIC4, BLINaC, hINaC, $P2X_1$, $P2X_2$, $P2X_3$, $P2X_4$, $P2X_5$, $P2X_6$, $P2X_7$, TRPV1, TRPV2, TRPV3, TRPV4, TRPV5, TRPV6. The language "chemical interaction" is intended to include, but is not limited to reversible interactions such as hydrophobic/hydrophilic, ionic (e.g., coulombic attraction/repulsion, ion-dipole, charge-transfer), covalent bonding, Van der Waals, and hydrogen bonding. In certain embodiments, the chemical interaction is a reversible Michael addition. In a specific embodiment, the Michael addition involves, at least in part, the formation of a covalent bond.

In particular embodiment, compound A can be used to treat pain in a subject in need thereof. In one embodiment, the subject is a human.

In another embodiment, compound A can be used to treat inflammation in a subject in need thereof. In one embodiment, the subject is a human.

In another embodiment, compound A is an AMPA antagonist.

Compounds of the inventions can be synthesized according to standard organic synthesis procedures that are known in the art. Representative synthesis procedures for compounds similar to the compounds of the invention can be found in U.S. Pat. No. 5,780,493, U.S. Pat. No. 5,843,945, U.S. Pat. No. 6,727, 260 and U.S. patent application Ser. Nos. 10/737,747 and 11/241,805, each of which are incorporated herein by reference.

Below is a scheme for a specific embodiment of the invention using organic starting materials and synthesis procedures well-known in organic chemistry synthesis:

in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

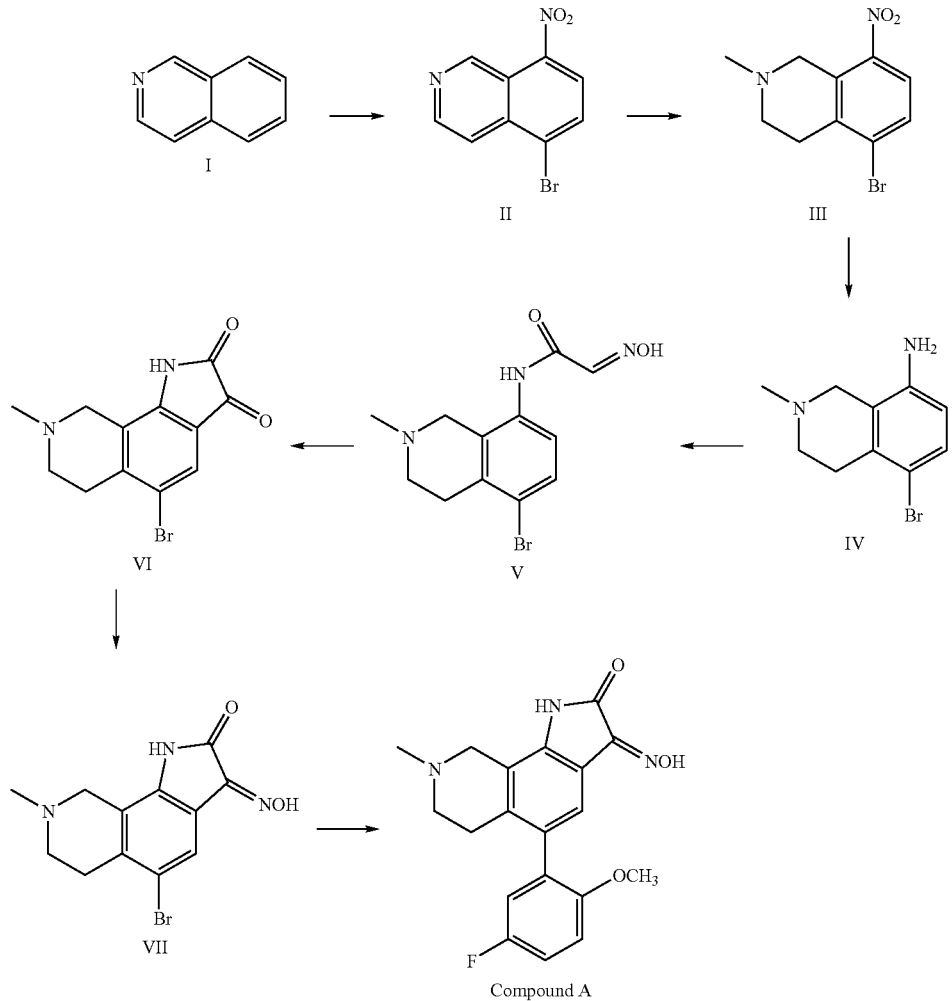

The synthetic details for the synthesis of Compound A can be found in Example 8.

The end products of the reactions described herein can be isolated by conventional techniques, e.g. by extraction, crystallization, distillation, chromatography, etc.

Acid addition salts of the compounds of the invention are most suitably formed from pharmaceutically acceptable acids, and include for example those formed with inorganic acids e.g. hydrochloric, hydrobromic, sulphuric or phosphoric acids and organic acids e.g. succinic, malaeic, acetic or fumaric acid. Other non-pharmaceutically acceptable salts e.g. oxalates can be used for example in the isolation of the compounds of the invention, for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, In vivo hydrolyzable esters or amides of certain compounds of the invention can be formed by treating those compounds having a free hydroxy or amino functionality with the acid chloride of the desired ester in the presence of a base in an inert solvent such as methylene chloride or chloroform. Suitable bases include triethylamine or pyridine. Conversely, compounds of the invention having a free carboxy group can be esterified using standard conditions which can include activation followed by treatment with the desired alcohol in the presence of a suitable base.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Particularly preferred salts are sodium, lysine and arginine salts of the compounds of the invention. Such salts can be formed by procedures well known and described in the art.

Other acids such as oxalic acid, which can not be considered pharmaceutically acceptable, can be useful in the preparation of salts useful as intermediates in obtaining a chemical compound of the invention and its pharmaceutically acceptable acid addition salt.

Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkyl-onium salts.

The chemical compound of the invention can be provided in dissoluble or indissoluble forms together with a pharmaceutically acceptable solvents such as water, ethanol, and the like. Dissoluble forms can also include hydrated forms such as the monohydrate, the dihydrate, the hemihydrate, the trihydrate, the tetrahydrate, and the like. In general, the dissoluble forms are considered equivalent to indissoluble forms for the purposes of this invention.

A. Stereoisomers

The chemical compounds of the present invention can exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallization of d- or l-(tartrates, mandelates, or camphorsulphonate) salts for example.

The chemical compounds of the present invention can also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, and Wilen S in "*Enantiomers, Racemates, and Resolutions*", John Wiley and Sons, New York (1981).

Optical active compounds can also be prepared from optical active starting materials.

Moreover, some of the chemical compounds of the invention being oximes, can thus exist in two forms, syn- and anti-form (Z- and E-form), depending on the arrangement of the substitutents around the —C=N— double bond. A chemical compound of the present invention can thus be the syn- or the anti-form (Z- and E-form), or it can be a mixture hereof. It is to be understood that both the syn- and anti-form (Z- and E-form) of a particular compound is within the scope of the present invention, even when the compound is represented herein (i.e., through nomenclature or the actual drawing of the molecule) in one form or the other.

In yet another embodiment, the invention pertains to pharmaceutical compositions comprising gated ion channel modulating compounds described herein and a pharmaceutical acceptable carrier.

In another embodiment, the invention includes any novel compound or pharmaceutical compositions containing compounds of the invention described herein. For example, compounds and pharmaceutical compositions containing compounds set forth herein (e.g., compounds of the invention) are part of this invention, including salts thereof, e.g., pharmaceutically acceptable salts.

Assays

The present invention relates to a method of modulating gated ion channel activity. As used herein, the various forms of the term "modulate" include stimulation (e.g., increasing or upregulating a particular response or activity) and inhibition (e.g., decreasing or downregulating a particular response or activity). In one aspect, the methods of the present invention comprise contacting a cell with an effective amount of a gated ion channel modulator compound, e.g. a compound of the invention, thereby modulating the activity of a gated ion channel. In certain embodiments, the effective amount of the compound of the invention inhibits the activity of the gated ion channel The gated ion channels of the present invention are comprised of at least one subunit belonging to the DEG/ENaC, TRPV (also referred to as vanilloid) and/or P2X gene superfamilies. In one aspect the gated ion channel is comprised of at least one subunit selected from the group consisting of αENaC, βENaC, γENaC, δENaC, ASIC1a, ASIC1b, ASIC2a, ASIC2b, ASIC3, ASIC4, BLINaC, hINaC, P2X$_1$, P2X$_2$, P2X$_3$, P2X$_4$, P2X$_5$, P2X$_6$, P2X$_7$, TRPV1, TRPV2, TRPV3, TRPV4, TRPV5, and TRPV6. In one aspect, the DEG/ENaC gated ion channel is comprised of at least one subunit selected from the group consisting of αENaC, βENaC, γENaC, δENaC, BLINaC, hINaC, ASIC1a, ASIC1b, ASIC2a, ASIC2b, ASIC3, and ASIC4. In certain embodiments, the DEG/ENaC gated ion channel is comprised of at least one subunit selected from the group consisting of ASIC1a, ASIC1b, ASIC2a, ASIC2b, ASIC3, and ASIC4. In certain embodiments, the gated ion channel is comprised of ASIC1a, ASIC1b, or ASIC3. In another aspect of the invention, P2X gated ion channel is comprised of at least one subunit selected from the group consisting of P2X$_1$, P2X$_2$, P2X$_3$, P2X$_4$, P2X$_5$, P2X$_6$, and P2X$_7$. In yet another aspect of the invention, the TRPV gated ion channel is comprised of at least one subunit selected from the group TRPV1, TRPV2, TRPV3, TRPV4, TRPV5, and TRPV6. In another aspect, the gated ion channel is a heteromultimeric gated ion channel, including, but not limited to, αENaC, βENaC and γENaC; αENaC, βENaC and δENaC; ASIC1a and ASIC2a; ASIC1a and ASIC2b; ASIC1a and ASIC3; ASIC1b and ASIC3; ASIC2a and ASIC2b; ASIC2a and ASIC3; ASIC2b and ASIC3; ASIC1a, ASIC2a and ASIC3; ASIC3 and P2X, e.g. $P2X_1$, $P2X_2$, $P2X_3$, $P2X_4$, $P2X_5$, $P2X_6$ and $P2X_7$, preferably ASIC3 and $P2X_2$; ASIC3 and $P2X_3$; and ASIC3, $P2X_2$ and $P2X_3$; ASIC4 and at least one of ASIC1a, ASIC1b, ASIC2a, ASIC2b, and ASIC3; BLINaC (or hINaC) and at least one of ASIC1a, ASIC1b, ASIC2a, ASIC2b, ASIC3, and ASIC4; δENaC and ASIC, e.g. ASIC1a, ASIC1b, ASIC2a, ASIC2b, ASIC3 and ASIC4; $P2X_1$, and $P2X_2$, $P2X_1$, and $P2X_5$, $P2X_2$ and $P2X_3$, $P2X_2$ and P2×6, $P2X_4$ and P2×6, TRPV1 and TRPV2, TRPV5 and TRPV6, TRPV1 and TRPV4.

Assays for determining the ability of a compound within the scope of the invention to modulate the activity of gated ion channels are well known in the art and described herein in the Examples section. Other assays for determining the ability of a compound to modulate the activity of a gated ion channel are also readily available to the skilled artisan.

The gated ion channel modulating compounds of the invention can be identified using the following screening method, which method comprises the subsequent steps of (i) subjecting a gated ion channel containing cell to the action of a selective activator, e.g., protons by adjustment of the pH to an acidic level, ATP by diluting sufficient amounts of ATP in the perfusion buffer or temperature by heating the perfusion buffer to temperatures above 37° C.;

(ii) subjecting a gated ion channel containing cell to the action of the chemical compound (the compound can be co-applied, pre-applied or post-applied); and (iii) monitoring the change in membrane potential or ionic current induced by the activator, e.g., protons, on the gated ion channel containing cell. Alternatively, fluorescent imaging can be utilized to monitor the effect induced by the activator, e.g., protons, on the gated ion channel containing cell.

The gated ion channel containing cells can be subjected to the action of protons by adjustment of the pH to an acidic level using any convenient acid or buffer, including organic acids such as formic acid, acetic acid, citric acid, ascorbic acid, 2-morpholinoethanesulfonic acid (MES) and lactic acid, and inorganic acids such as hydrochloric acid, hydrobromic acid and nitric acid, perchloric acid and phosphoric acid.

In the methods of the invention, the current flux induced by the activator, e.g., protons, across the membrane of the gated ion channel containing cell can be monitored by electrophysiological methods, for example patch clamp or two-electrode voltage clamp techniques.

Alternatively, the change in membrane potential induced by gated ion channel activators, e.g., protons of the gated ion channel containing cells can be monitored using fluorescence methods. When using fluorescence methods, the gated ion channel containing cells are incubated with a membrane potential indicating agent that allows for a determination of changes in the membrane potential of the cells, caused by the added activators, e.g., protons. Such membrane potential indicating agents include fluorescent indicators, preferably $DiBAC_4(3)$, DiOC5(3), DiOC2(3), DiSBAC2(3) and the FMP (FLIPR membrane potential) dyes (Molecular Devices).

In another alternative embodiment, the change in gated ion channel activity induced by activators, e.g., protons, on the gated ion channel can be measured by assessing changes in the intracellular concentration of certain ions, e.g., calcium, sodium, potassium, magnesium, protons, and chloride in cells by fluorescence. Fluorescence assays can be performed in multi-well plates using plate readers, e.g., FLIPR assay (Fluorescence Image Plate Reader; available from Molecular Devices), e.g. using fluorescent calcium indicators, e.g. as described in, for example, Sullivan E., et al. (1999) *Methods Mol. Biol.* 114:125-33, Jerman, J. C., et al. (2000) *Br J Pharmacol* 130(4):916-22, and U.S. Pat. No. 6,608,671, the contents of each of which are incorporated herein by reference. When using such fluorescence methods, the gated ion channel containing cells are incubated with a selective ion indicating agent that allows for a determination of changes in the intracellular concentration of the ion, caused by the added activators, e.g., protons. Such ion indicating agents include fluorescent calcium indicators, preferably Fura-2, Fluo-3, Fluo-4, Fluo-4FF, Fluo-5F, Fluo-5N, Calcium Green, Fura-Red, Indo-1, Indo-5F, and rhod-2, fluorescent sodium indicators, preferably SBFI, Sodium Green, CoroNa Green, fluorescent potassium indicators, preferably PBFI, CD222, fluorescent magnesium indicators, preferably Mag-Fluo-4, Mag-Fura-2, Mag-Fura-5, Mag-Fura-Red, Mag-indo-1, Mag-rho-2, Magnesium Green, fluorescent chloride indicators, preferably SPQ, Bis-DMXPQ, LZQ, MEQ, and MQAE, fluorescent pH indicators, preferably BCECF and BCPCF.

The gated ion channel antagonizing compounds of the invention show activity in concentrations below 2M, 1.5M, 1M, 500 mM, 250 mM, 100 mM, 750 μM, 500 μM, 250 μM, 100 μM, 75 μM, 50 μM, 25 μM, 10 μM, 5 μM, 2.5 μM, or below 1 μM. In its most preferred embodiment the ASIC antagonizing compounds show activity in low micromolar and the nanomolar range.

As used herein, the term "contacting" (i.e., contacting a cell e.g. a neuronal cell, with a compound) is intended to include incubating the compound and the cell together in vitro (e.g., adding the compound to cells in culture) or administering the compound to a subject such that the compound and cells of the subject are contacted in vivo. The term "contacting" is not intended to include exposure of cells to a modulator or compound that can occur naturally in a subject (i.e., exposure that can occur as a result of a natural physiological process).

A. In Vitro Assays

Gated ion channel polypeptides for use in the assays described herein can be readily produced by standard biological techniques or by chemical synthesis. For example, a host cell transfected with an expression vector containing a nucleotide sequence encoding the desired gated ion channel can be cultured under appropriate conditions to allow expression of the peptide to occur. Alternatively, the gated ion channel can be obtained by culturing a primary cell line or an established cell line that can produce the gated ion channel.

The methods of the invention can be practiced in vitro, for example, in a cell-based culture screening assay to screen compounds which potentially bind, activate or modulate gated ion channel function. In such a method, the modulating compound can function by interacting with and eliminating any specific function of gated ion channel in the sample or culture. The modulating compounds can also be used to control gated ion channel activity in neuronal cell culture.

Cells for use in in vitro assays, in which gated ion channels are naturally present, include various cells, such as cortical neuronal cells, in particular mouse or rat cortical neuronal cells, and human embryonic kidney (HEK) cells, in particular the HEK293 cell line. For example, cells can be cultured from embryonic human cells, neonatal human cells, and adult human cells. Primary cell cultures can also be used in the methods of the invention. For example, sensory neuronal cells can also be isolated and cultured in vitro from different animal species. The most widely used protocols use sensory neurons isolated from neonatal (Eckert, et al. (1997) *J Neu-* rosci Methods 77:183-190) and embryonic (Vasko, et al. (1994) *J Neurosci* 14:4987-4997) rat. Trigeminal and dorsal root ganglion sensory neurons in culture exhibit certain characteristics of sensory neurons in vivo.

Alternatively, the gated ion channel, e.g., a gated channel, e.g., a proton gated ion channel, can be exogenous to the cell in question, and can in particular be introduced by recombinant DNA technology, such as transfection, microinjection or infection. Such cells include Chinese hamster ovary (CHO) cells, HEK cells, African green monkey kidney cell line (CV-1 or CV-1-derived COS cells, e.g. COS-1 and COS-7) *Xenopus laevis* oocytes, or any other cell lines capable of expressing gated ion channels.

The nucleotide and amino acid sequences of the gated ion channels of the invention are known in the art. For example, the sequences of the human gated channels can be found in Genbank GI Accession Nos: GI:40556387 (ENaCalpha *Homo sapiens*); GI:4506815 (ENaCalpha *Homo sapiens*); GI:4506816 (ENaCbeta *Homo sapiens*); GI:4506817 (ENaCbeta *Homo sapiens*); GI:34101281 (ENaCdelta *Homo sapiens*); GI:34101282 (ENaCdelta *Homo sapiens*); GI:42476332 (ENaCgamma *Homo sapiens*); GI:42476333 (ENaCgamma *Homo sapiens*); GI:31442760 (HINAC *Homo sapiens*); GI:31442761 (HINAC *Homo sapiens*); GI: 21536350 (ASIC1a *Homo sapiens*); GI:21536351 (ASIC1a *Homo sapiens*); GI:21536348(ASIC1b *Homo sapiens*); GI:21536349 (ASIC1b *Homo sapiens*); GI:34452694 (ASIC2; transcript variant 1 *Homo sapiens*); GI:34452695 (ASIC2; isoform 1 *Homo sapiens*); GI:34452696(ASIC2; transcript variant 2 *Homo sapiens*); GI:9998944 (ASIC2; isoform 2 *Homo sapiens*); GI:4757709 (ASIC3; transcript variant 1 *Homo sapiens*); GI:4757710(ASIC3; isoform 1 *Homo sapiens*); GI:9998945(ASIC3; transcript variant 2 *Homo sapiens*); GI:9998946 (ASIC3; isoform 2 *Homo sapiens*); GI:9998947 (ASIC3; transcript variant 3 *Homo sapiens*); GI: 9998948 (ASIC3; isoform 3 *Homo sapiens*); GI:33519441 (ASIC4; transcript variant 1 *Homo sapiens*); GI:33519442 (ASIC4; isoform 1 *Homo sapiens*); GI:33519443 (ASIC4; transcript variant 2 *Homo sapiens*); GI:33519444 (ASIC4; isoform 2 *Homo sapiens*); GI:27894283 (P2X$_1$ *Homo sapiens*); GI:4505545 (P2X$_1$ *Homo sapiens*); GI:28416917 (P2X$_2$; transcript variant 1 *Homo sapiens*); GI:25092719 (P2X$_2$; isoform A *Homo sapiens*); GI:28416922 (P2X$_2$; transcript variant 2 *Homo sapiens*); GI:28416923 (P2X$_2$; isoform B *Homo sapiens*); GI:28416916(P2X$_2$; transcript variant 3 *Homo sapiens*); GI:7706629 (P2X$_2$; isoform C *Homo sapiens*); GI:28416918(P2X$_2$; transcript variant 4 *Homo sapiens*); GI:25092733 (P2X$_2$; isoform D *Homo sapiens*); GI:28416920 (P2X$_2$; transcript variant 5 *Homo sapiens*); GI:28416921 (P2X$_2$; isoform H *Homo sapiens*); GI:28416919 (P2X$_2$; transcript variant 6 *Homo sapiens*); GI:27881423 (P2X$_2$; isoform I *Homo sapiens*); GI:28416924 (P2X$_3$ *Homo sapiens*); GI:28416925 (P2X$_3$ *Homo sapiens*); GI:28416926 (P2X$_4$; transcript variant 1 *Homo sapiens*); GI:28416927 (P2X$_4$; isoform A *Homo sapiens*); GI: 28416928 (P2X$_4$; transcript variant 2 *Homo sapiens*); GI:28416929 (P2X$_4$; isoform B *Homo sapiens*); GI:28416930 (P2X$_4$; transcript variant 3 *Homo sapiens*); GI:28416931 (P2X$_4$; isoform C *Homo sapiens*); GI:28416932 (P2X$_5$; transcript variant I *Homo sapiens*); GI:28416933 (P2X$_5$; isoform A *Homo sapiens*); GI:28416934 (P2X$_5$; transcript variant 2 *Homo sapiens*); GI:28416935 (P2X$_5$; isoform B *Homo sapiens*); GI:28416936 (P2X$_5$; transcript variant 3 *Homo sapiens*); GI:28416937 (P2X$_5$; isoform C *Homo sapiens*); GI:38327545 (P2X$_6$ *Homo sapiens*); GI:4885535 (P2X$_6$ *Homo sapiens*); GI:34335273 (P2X$_7$; transcript variant 1 *Homo sapiens*); GI:29294631 (P2X$_7$; isoform A *Homo sapiens*); GI:34335274 (P2X$_7$; transcript variant 2 *Homo sapiens*); GI:29294633 (P2X$_7$; isoform B *Homo sapiens*); GI:18375666 (TRPV1; transcript variant 1 *Homo sapiens*); GI:18375667(TRPV1; vanilloid receptor subtype 1 *Homo sapiens*); GI:18375664 (TRPV1; transcript variant 2 *Homo sapiens*); GI:18375665 (TRPV1; vanilloid receptor subtype 1 *Homo sapiens*); GI: 18375670 (TRPV1; transcript variant 3 *Homo sapiens*); GI:18375671(TRPV1; vanilloid receptor subtype 1 *Homo sapiens*); GI:18375668 (TRPV1; transcript variant 4 *Homo sapiens*); GI:18375669 (TRPV1; vanilloid receptor subtype 1 *Homo sapiens*); GI:7706764 (VRL-1; transcript variant 1 *Homo sapiens*); GI:7706765 (VRL-1; vanilloid receptor-like protein 1 *Homo sapiens*); GI:22547178 (TRPV2; transcript variant 2 *Homo sapiens*); GI:20127551 (TRPV2; vanilloid receptor-like protein 1 *Homo sapiens*); GI:22547183 (TRPV4; transcript variant 1 *Homo sapiens*); GI:22547184 (TRPV4; isoform A *Homo sapiens*); GI:22547179 (TRPV4; transcript variant 2 *Homo sapiens*); GI:22547180 (TRPV4; isoform B *Homo sapiens*); GI:21361832 (TRPV5 *Homo sapiens*); GI:17505200 (TRPV5 *Homo sapiens*); GI:21314681 (TRPV6 *Homo sapiens*); GI:21314682 (TRPV6 *Homo sapiens*); GI: 34452696 (ACCN1; transcript variant 2; *Homo sapiens*). The contents of each of these records are incorporated herein by reference. Additionally, sequences for channels of other species are readily available and obtainable by those skilled in the art.

A nucleic acid molecule encoding a gated ion channel for use in the methods of the present invention can be amplified using cDNA, mRNA, or genomic DNA as a template and appropriate oligonucleotide primers according to standard PCR amplification techniques. The nucleic acid so amplified can be cloned into an appropriate vector and characterized by DNA sequence analysis. Using all or a portion of such nucleic acid sequences, nucleic acid molecules of the invention can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

Expression vectors, containing a nucleic acid encoding a gated ion channel, e.g., a gated ion channel subunit protein, e.g., αENaC, βENaC, γENaC, δENaC, ASIC1a, ASIC1b, ASIC2a, ASIC2b, ASIC3, ASIC4, BLINaC, hINaC, P2X$_1$, P2X$_2$, P2X$_3$, P2X$_4$, P2X$_5$, P2X$_6$, P2X$_7$, TRPV1, TRPV2, TRPV3, TRPV4, TRPV5, and TRPV6 protein (or a portion thereof) are introduced into cells using standard techniques and operably linked to regulatory sequence. Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein.

Examples of vectors for expression in yeast *S. cerevisiae* include pYepSec1 (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Baculovirus vectors available for expression of proteins in cultured insect cells (e.g., Sf 9 cells) include the pAc series (Smith et al., 1983, *Mol. Cell. Biol.* 3:2156-2165) and the pVL series (Lucklow and Summers, 1989, *Virology* 170:31-39).

Examples of mammalian expression vectors include pCDM8 (Seed, 1987, *Nature* 329:840), pMT2PC (Kaufman et al., 1987, *EMBO J.* 6:187-195), pcDNA3. When used in mammalian cells, the expression vector's control functions are often provided by viral regulatory elements. For example, commonly used promoters are derived from polyoma, Adenovirus 2, cytomegalovirus and Simian Virus 40. For other suitable expression systems for eukaryotic cells see chapters 16 and 17 of Sambrook et al.

B. In Vivo Assays

The activity of the compounds of the invention as described herein to modulate one or more gated ion channel activities (e.g., a gated ion channel modulator, e.g., a compound of the invention) can be assayed in an animal model to determine the efficacy, toxicity, or side effects of treatment with such an agent. Alternatively, an agent identified as described herein can be used in an animal model to determine the mechanism of action of such an agent.

Animal models for determining the ability of a compound of the invention to modulate a gated ion channel biological activity are well known and readily available to the skilled artisan. Examples of animal models for pain and inflammation include, but are not limited to the models listed in Table 1. Animal models for investigating neurological disorders include, but are not limited to, those described in Morris et al., (Learn. Motiv. 1981; 12: 239-60) and Abeliovitch et al., Cell 1993; 75: 1263-71). An example of an animal model for investigating mental and behavioral disorders is the Geller-Seifter paradigm, as described in Psychopharmacology (Berl). 1979 April 11; 62(2):117-21.

Genitourinary models include methods for reducing the bladder capacity of test animals by infusing either protamine sulfate and potassium chloride (See, Chuang, Y. C. et al., Urology 61(3): 664-670 (2003)) or dilute acetic acid (See, Sasaki, K. et al., J. Urol. 168(3): 1259-1264 (2002)) into the bladder. For urinary tract disorders involving the bladder using intravesically administered protamine sulfate as described in Chuang et al. (2003) Urology 61: 664-70. These methods also include the use of a well accepted model of for urinary tract disorders involving the bladder using intravesically administered acetic acid as described in Sasaki et al. (2002) J. Urol. 168: 1259-64. Efficacy for treating spinal cord injured patients can be tested using methods as described in Yoshiyama et al. (1999) Urology 54: 929-33.

Animal models of neuropathic pain based on injury inflicted to a nerve (mostly the sciatic nerve) are described in Bennett et al., 1988, Pain 33:87-107; Seltzer et al., 1990, Pain 43:205-218; Kim et al., 1992, Pain 50:355-363; Decosterd et al., 2000, Pain 87:149-158 and DeLeo et al., 1994, Pain 56:9-16. There are also models of diabetic neuropathy (STZ induced diabetic neuropathy—Courteix et al., 1994, Pain 57:153-160) and drug induced neuropathies (vincristine induced neuropathy—Aley et al., 1996, Neuroscience 73: 259-265; oncology-related immunotherapy, anti-GD2 antibodies—Slart et al., 1997, Pain 60:119-125). Acute pain in humans can be reproduced using in murine animals chemical stimulation: Martinez et al., Pain 81: 179-186; 1999 (the writhing test—intraperitoneal acetic acid in mice), Dubuisson et al. Pain 1977; 4: 161-74 (intraplantar injection of formalin). Other types of acute pain models are described in Whiteside et al., 2004, Br J Pharmacol 141:85-91 (the incisional model, a post-surgery model of pain) and Johanek and Simone, 2004, Pain 109:432-442 (a heat injury model). An animal model of inflammatory pain using complete Freund's adjuvant (intraplantar injection) is described in Jasmin et al., 1998, Pain 75: 367-382. Intracapsular injection of irritant agents (complete Freund's adjuvant, iodoacetate, capsaicine, urate crystals, etc.) is used to develop arthritis models in animals (Fernihough et al., 2004, Pain 112:83-93; Coderre and Wall, 1987, Pain 28:379-393; Otsuki et al., 1986, Brain Res. 365:235-240). A stress-induced hyperalgesia model is described in Quintero et al., 2000, Pharmacology, Biochemistry and Behavior 67:449-458. Further animal models for pain are considered in an article of Walker et al. 1999 Molecular Medicine Today 5:319-321, comparing models for different types of pain, which are acute pain, chronic/inflammatory pain and chronic/neuropathic pain, on the basis of behavioral signs. Animal models for depression are described by E. Tatarczynska et al., Br. J. Pharmacol. 132(7): 1423-1430 (2001) and P. J. M. Will et al., Trends in Pharmacological Sciences 22(7):331-37(2001)); models for anxiety are described by D. Treit, "Animal Models for the Study of Antianxiety Agents: A Review," Neuroscience & Biobehavioral Reviews 9(2):203-222 (1985). Additional animal models for pain are also described herein in the Exemplification section.

Gastrointestinal models can be found in: Gawad, K. A., et al., Ambulatory long-term pH monitoring in pigs, Surg Endosc, (2003); Johnson, S. E. et al., Esophageal Acid Clearance Test in Healthy Dogs, Can. J. Vet. Res. 53(2): 244-7 (1989); and Cicente, Y. et al., Esophageal Acid Clearance: More Volume-dependent Than Motility Dependent in Healthy Piglets, J. Pediatr. Gastroenterol. Nutr. 35(2): 173-9 (2002). Models for a variety of assays can be used to assess visceromotor and pain responses to rectal distension. See, for example, Gunter et al., Physiol. Behav., 69(3): 379-82 (2000), Depoortere et al., J. Pharmacol. and Exp. Ther., 294(3): 983-990(2000), Morteau et al., Fund. Clin. Pharmacol., 8(6): 553-62 (1994), Gibson et al., Gastroenterology (Suppl. 1), 120(5): A19-A20 (2001) and Gschossmann et al., Eur. J. Gastro. Hepat., 14(10): 1067-72 (2002) the entire contents of which are each incorporated herein by reference.

Gastrointestinal motility can be assessed based on either the in vivo recording of mechanical or electrical events associated intestinal muscle contractions in whole animals or the activity of isolated gastrointestinal intestinal muscle preparations recorded in vitro in organ baths (see, for example, Yaun et al., Br. J. Pharmacol., 112(4):1095-1100 (1994), Jin et al., J. Pharm. Exp. Ther., 288(1): 93-97 (1999) and Venkova et al., J. Pharm. Exp. Ther., 300(3): 1046-1052 (2002)). Tatersall et al. and Bountra et al., European Journal of Pharmacology, 250: (1993) R5 and 249:(1993) R3-R4 and Milano et al., J. Pharmacol. Exp. Ther., 274(2): 951-961 (1995).

TABLE 1

| Model Name | Modality tested | Brief Description | Non-limiting examples of potential clinical indications (Reference) |
|---|---|---|---|
| | | ACUTE PHASIC PAIN | |
| Tail-flick | Thermal | Tip of tail of rats is immersed if hot water and time to withdrawal from water is measured. Alternatively, a radiant heat source is applied to the tail and time to withdrawal is determined. Analgesic effect is evidenced by a prolongation of the latency period | Acute nociceptive pain (Hardy et al. Am J Physiol 1957; 189: 1-5.; Ben-Bassat et al. Arch Intern Pharmacodyn Ther 1959; 122: 434-47.) |
| hot-plate | Thermal | Rats walk over a heated surface with increasing temperature and observed for specific nociceptive behavior such paw licking, jumping. Time to appearance of such behavior is measured. Analgesic effects are evidenced by a prolonged latency. | Acute nociceptive pain (Woolfe et al. J Pharmacol Exp Ther 1944; 80: 300-7.) |
| Hargreaves Test | Thermal | A focused beam of light is projected onto a small surface of the hind leg of a rat with increasing temperature. Time to withdrawal is measured. Analgesic effect translates into a prolonged latency. | Acute nociceptive pain (Yeomans et al. Pain 1994; 59: 85-94.) |
| Pin Test or Randall Selitto | Mechanical | An increasing calibrated pressure is applied to the paw of rats with a blunt pin. Pressure intensity is measured. Alternatively increased pressure is applied to the paw using a caliper until pain threshold is reached and animals withdraw the paw. | Acute nociceptive pain (Green et al. Br J Pharmacol 1951; 6: 572-85.; Randall et al. Arch Int Pharmacodyn Ther 1957; 111: 409-19) |
| | | HYPERALGESIA MODELS/CHRONIC INFLAMMATORY PAIN MODELS | |
| Hargreaves or Randal & Selitto | Thermal and/or mechanical | A sensitizing agent (e.g, complete Freund's adjuvant (CFA), carrageenin, turpentine etc.) is injected into the paw of rats creating a local inflammation and sensitivities to mechanical (Randall & Selitto) and/or therma (Hargreaves)I stimulation are measured with comparison to the contralateral non-sensitized paw | Chronic pain associated with tissue inflammation, e.g. post-surgical pain, (Hargreaves et al. Pain 1988; 32: 77-88.) Randall LO, Selitto JJ. Arch Int Pharmacodyn 1957; 3: 409-19. |
| Yeomans model | Thermal | Rat hind paw in injected with capsaicin, a sensitizing agent for small C-fibers or DMSO, a sensitizing agent for A-delta fibers. A radiant heat is applied with different gradient to differentially stimulate C-fibers or A-delta fibers and discriminate between the effects mediated by both pathways | Chronic pain associated with tissue inflammation, e.g. post-surgical pain (Yeomans et al. Pain 1994; 59: 85-94.; Otsuki et al. Brain Res 1986; 365: 235-240.) |
| | | CHRONIC MALIGNANT PAIN (CANCER PAIN) | |
| Bone Cancer Model | Thermal and/or mechanical | In this model, osteolytic mouse sarcoma NCTC2472 cells are used to induce bone cancer by injecting tumor cells into the marrow space of the femur bone and sealing the injection site | Bone cancer pain (Schwei et al., J. Neurosci. 1999; 19: 10886-10897.) |
| Cancer invasion pain model (CIP) | Thermal and/or mechanical | Meth A sarcoma cells are implanted around the sciatic nerve in BALB/c mice and these animals develop signs of allodynia and thermal hyperalgesia as the tumor grows, compressing the nerve. Spontaneous pain (paw lifting) is also visible. | Malignant neuropathic pain (Shimoyama et al., Pain 2002; 99: 167-174.) |
| | | CHRONIC NON-MALIGNANT PAIN | |
| Muscle Pain | Thermal and/or mechanical | Repeated injections of acidic saline into one gastrocnemius muscle produces bilateral, long-lasting mechanical hypersensitivity of the paw (i.e. hyperalgesia) without associated tissue damage | Fibromyalgia (Sluka et al. Pain 2003; 106: 229-239.) |
| UV-irradiation | Thermal and/or mechanical | Exposure of the rat hind paw to UV irradiation produces highly reliable and persistent allodynia. Various irradiation periods with UV-B produce skin inflammation with different time courses | Inflammatory pain associated with first and second-degree burns. (Perkins et al. Pain 1993; 53: 191-197.) |
| | | CHRONIC NEUROPATHIC PAIN | |
| Chronic Constriction Injury (CCI) or Bennett and Xie model | Mostly mechanical but aso thermal | Loose chronic ligature of the sciatic nerve. Thermal or mechanical sensitivities are tested using Von Frey hairs or the paw withdrawal test (Hargreaves) | Clinical Neuropathic pain: nerve compression and direct mechanical neuronal damage might be relevant clinical comparisons (Bennett & Xie, Neuropharmacology 1984; 23: 1415-1418.) |
| Chung's model or Spinal Nerve Ligation model (SNL) | Mostly mechanical but aso thermal | Tight ligation of one of the two spinal nerves of the sciatic nerve. Thermal or mechanical sensitivities are tested using Von Frey hairs or the paw withdrawal test (Hargreaves) | Same as above: root compression might be a relevant clinical comparison (Kim and Chung, Pain 1990; 41: 235-251.) |

Alternatively, the compounds can also be assayed in non-human transgenic animals containing exogenous sequences encoding one or more gated ion channels. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. Methods for generating transgenic animals via embryo manipulation and microinjection, particularly animals such as mice, have become conventional in the art and are described, for example, in U.S. Pat. Nos. 4,736,866 and 4,870,009, U.S. Pat. No. 4,873,191 and in Hogan, *Manipulating the Mouse Embryo*, Cold Spring Harbor Laboratory Press, Cold Spring Harbor, N.Y., 1986. Similar methods are used for production of other transgenic animals.

A homologous recombinant animal can also be used to assay the compounds of the invention. Such animals can be generated according to well known techniques (see, e.g., Thomas and Capecchi, 1987, *Cell* 51:503; Li et al., 1992, *Cell* 69:915; Bradley, *Teratocarcinomas and Embryonic Stem Cells: A Practical Approach*, Robertson, Ed., IRL, Oxford, 1987, pp. 113-152; Bradley (1991) *Current Opinion in Bio/Technology* 2:823-829 and in PCT Publication NOS. WO 90/11354, WO 91/01140, WO 92/0968, and WO 93/04169).

Other useful transgenic non-human animals can be produced which contain selected systems which allow for regulated expression of the transgene (see, e.g., Lakso et al. (1992) *Proc. Natl. Acad. Sci. USA* 89:6232-6236). Another example of a recombinase system is the FLP recombinase system of *Saccharomyces cerevisiae* (O'Gorman et al., 1991, Science 251:1351-1355).

Pharmaceutical Compositions

The present invention also provides pharmaceutical compositions. Such compositions comprise a therapeutically (or prophylactically) effective amount of a gated ion channel modulator, and preferably one or more compounds of the invention described above, and a pharmaceutically acceptable carrier or excipient. Suitable pharmaceutically acceptable carriers include, but are not limited to, saline, buffered saline, dextrose, water, glycerol, ethanol, and combinations thereof. The carrier and composition can be sterile. The formulation should suit the mode of administration.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the subject. Some examples of materials which can serve as pharmaceutically acceptable carriers include: sugars, such as lactose, glucose, dextrose and sucrose; starches, such as corn starch and potato starch; cellulose, and its derivatives, such as sodium carboxymethyl cellulose, ethyl cellulose, methylcellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, castor oil, tetraglycol, and soybean oil; glycols, such as propylene glycol; polyols, such as glycerin, sorbitol, mannitol and polyethylene glycol; esters, such as ethyl oleate, esters of polyethylene glycol and ethyl laurate; agar; buffering agents, such as magnesium hydroxide, sodium hydroxide, potassium hydroxide, carbonates, triethylanolamine, acetates, lactates, potassium citrate and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol and derivatives such as vitamin E tocopherol, and the like; and metal chelating agents, such as citric acid, ethylenediamine tetraacetic acid (EDTA), sorbitol, tartaric acid, phosphoric acid, sodium citrate and the like.

Suitable pharmaceutically acceptable carriers include but are not limited to water, salt solutions (e.g., NaCl), alcohols, gum arabic, vegetable oils, benzyl alcohols, polyethylene glycols, gelatin, carbohydrates such as lactose, amylose or starch, cyclodextrin, magnesium stearate, talc, silicic acid, viscous paraffin, perfume oil, fatty acid esters, hydroxymethylcellulose, polyvinyl pyrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. The pharmaceutically acceptable carriers can also include a tonicity-adjusting agent such as dextrose, glycerine, mannitol and sodium chloride.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose, magnesium carbonate, etc.

The composition can be formulated in accordance with the routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients can be mixed prior to administration.

The pharmaceutical compositions of the invention can also include an agent which controls release of the gated ion channel modulator compound, thereby providing a timed or sustained release composition.

The present invention also relates to prodrugs of the gated ion channel modulators disclosed herein, as well as pharmaceutical compositions comprising such prodrugs. For example, compounds of the invention which include acid functional groups or hydroxyl groups can also be prepared and administered as a corresponding ester with a suitable alcohol or acid. The ester can then be cleaved by endogenous enzymes within the subject to produce the active agent.

Formulations of the present invention include those suitable for oral, nasal, topical, mucous membrane, transdermal, buccal, sublingual, rectal, vaginal and/or parenteral administration. The formulations can conveniently be presented in unit dosage form and can be prepared by any methods well known in the art of pharmacy. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration can be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention can also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions can also comprise buffering agents. Solid compositions of a similar type can also be employed as fillers in soft and hard-filled gelatin capsules using such excipients as lactose or milk sugars, as well as high molecular weight polyethylene glycols and the like.

A tablet can be made by compression or molding, optionally with one or more accessory ingredients. Compressed tablets can be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets can be made by molding in a suitable machine a mixture of the powdered compound moistened with an inert liquid diluent.

The tablets, and other solid dosage forms of the pharmaceutical compositions of the present invention, such as dragees, capsules, pills and granules, can optionally be scored or prepared with coatings and shells, such as enteric coatings and other coatings well known in the pharmaceutical-formulating art. They can also be formulated so as to provide slow or controlled release of the active ingredient therein using, for example, hydroxypropylmethyl cellulose in varying proportions to provide the desired release profile, other polymer matrices, liposomes and/or microspheres. They can be sterilized by, for example, filtration through a bacteria-retaining filter, or by incorporating sterilizing agents in the form of sterile solid compositions that can be dissolved in sterile water, or some other sterile injectable medium immediately before use. These compositions can also optionally contain opacifying agents and can be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms can contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration can be presented as a suppository, which can be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound can be mixed under sterile conditions with a pharmaceutically acceptable carrier, and with any preservatives, buffers, or propellants that can be required.

The ointments, pastes, creams and gels can contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which can be reconstituted into sterile injectable solutions or dispersions just prior to use, which can contain antioxidants, buffers, bacteriostats, solutes which render the formulation isotonic with the blood of the intended recipient or suspending or thickening agents.

Examples of suitable aqueous and nonaqueous carriers that can be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents that delay absorption such as aluminum monostearate and gelatin.

In some cases, in order to prolong the effect of a drug, it is desirable to slow the absorption of the drug from subcutaneous or intramuscular injection. This can be accomplished by the use of a liquid suspension of crystalline or amorphous material having poor water solubility. The rate of absorption of the drug then depends upon its rate of dissolution which, in turn, can depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

Methods of Administration

The invention provides a method of treating a condition mediated by gated ion channel activity in a subject, including, but not limited to, pain, inflammatory disorders, neurological disorders, gastrointestinal disorders and genitourinary disorders. The method comprises the step of administering to the subject a therapeutically effective amount of a gated ion channel modulator. The condition to be treated can be any condition which is mediated, at least in part, by the activity of a gated ion channel (e.g., ASIC1a and/or ASIC3).

The quantity of a given compound to be administered will be determined on an individual basis and will be determined, at least in part, by consideration of the individual's size, the severity of symptoms to be treated and the result sought. The gated ion channel activity modulators described herein can be administered alone or in a pharmaceutical composition comprising the modulator, an acceptable carrier or diluent and, optionally, one or more additional drugs.

These compounds can be administered to humans and other animals for therapy by any suitable route of administration. The gated ion channel modulator can be administered subcutaneously, intravenously, parenterally, intraperitoneally, intradermally, intramuscularly, topically, enterally (e.g., orally), rectally, nasally, buccally, sublingually, systemically, vaginally, by inhalation spray, by drug pump or via an implanted reservoir in dosage formulations containing conventional non-toxic, physiologically acceptable carriers or vehicles. The preferred method of administration is by oral delivery. The form in which it is administered (e.g., syrup, elixir, capsule, tablet, solution, foams, emulsion, gel, sol) will depend in part on the route by which it is administered. For example, for mucosal (e.g., oral mucosa, rectal mucosa, intestinal mucosa, bronchial mucosa) administration, nose drops, aerosols, inhalants, nebulizers, eye drops or suppositories can be used. The compounds and agents of this invention can be administered together with other biologically active agents, such as analgesics, e.g., opiates, anti-inflammatory agents, e.g., NSAIDs, anesthetics and other agents which can control one or more symptoms or causes of a gated ion channel mediated condition.

In a specific embodiment, it can be desirable to administer the agents of the invention locally to a localized area in need of treatment; this can be achieved by, for example, and not by way of limitation, local infusion during surgery, topical application, transdermal patches, by injection, by means of a catheter, by means of a suppository, or by means of an implant, said implant being of a porous, non-porous, or gelatinous material, including membranes, such as sialastic membranes or fibers. For example, the agent can be injected into the joints or the urinary bladder.

The compounds of the invention can, optionally, be administered in combination with one or more additional drugs which, for example, are known for treating and/or alleviating symptoms of the condition mediated by a gated ion channel (e.g., ASIC1a and/or ASIC3). The additional drug can be administered simultaneously with the compound of the invention, or sequentially. For example, the compounds of the invention can be administered in combination with at least one of an analgesic, an anti-inflammatory agent, an anesthetic, a corticosteroid (e.g., dexamethasone, beclomethasone diproprionate (BDP) treatment), an anti-convulsant, an antidepressant, an anti-nausea agent, an anti-psychotic agent, a cardiovascular agent (e.g., a beta-blocker) or a cancer therapeutic. In certain embodiments, the compounds of the invention are administered in combination with a pain drug. As used herein the phrase, "pain drugs" is intended to refer to analgesics, anti-inflammatory agents, anesthetics, corticosteroids, antiepileptics, barbiturates, antidepressants, and marijuana.

The combination treatments mentioned above can be started prior to, concurrent with, or after the administration of the compositions of the present invention. Accordingly, the methods of the invention can further include the step of administering a second treatment, such as a second treatment for the disease or disorder or to ameliorate side effects of other treatments. Such second treatment can include, e.g., anti-inflammatory medication and any treatment directed toward treating pain. Additionally or alternatively, further treatment can include administration of drugs to further treat the disease or to treat a side effect of the disease or other treatments (e.g., anti-nausea drugs, anti-inflammatory drugs, anti-depressants, anti-psychiatric drugs, anti-convulsants, steroids, cardiovascular drugs, and cancer chemotherapeutics).

As used herein, an "analgesic" is an agent that relieves or reduces pain or any signs or symptoms thereof (e.g., hyperalgesia, allodynia, dysesthesia, hyperesthesia, hyperpathia, paresthesia) and can also result in the reduction of inflammation, e.g., an anti-inflammatory agent. Analgesics can be subdivided into NSAIDs (non-steroidal-anti-inflammatory drugs), narcotic analgesics, including opioid analgesics, and non-narcotic analgesics. NSAIDs can be further subdivided into non-selective COX (cyclooxygenase) inhibitors, and selective COX2 inhibitors. Opioid analgesics can be natural, synthetic or semi-synthetic opioid analgesics, and include for example, morphine, codeine, meperidine, propxyphen, oxycodone, hydromorphone, heroine, tramadol, and fentanyl. Non-narcotic analgesics (also called non-opioid) analgesics include, for example, acetaminophen, clonidine, NMDA antagonists, vanilloid receptor antagonists (e.g., TRPV1 antagonists), pregabalin, endocannabinoids and cannabinoids. Non-selective COX inhibitors include, but are not limited to acetylsalicylic acid (ASA), ibuprofen, naproxen, ketoprofen, piroxicam, etodolac, and bromfenac. Selective COX2 inhibitors include, but are not limited to celecoxib, valdecoxib, parecoxib, and etoricoxib.

As used herein an "anesthetic" is an agent that interferes with sense perception near the site of administration, a local anesthetic, or result in alteration or loss of consciousness, e.g., systemic anesthetic agents. Local anesthetics include but are not limited to lidocaine and buvicaine.

Non-limiting examples of antiepileptic agents are carbamazepine, phenyloin and gabapentin. Non-limiting examples of antidepressants are amitriptyline and desmethylimiprimine.

Non-limiting examples of anti-inflammatory drugs include corticosteroids (e.g., hydrocortisone, cortisone, prednisone, prednisolone, methyl prednisone, triamcinolone, flupredinisolone, betamethasone and dexamethasone), salicylates, NSAIDs, antihistamines and $H_2$ receptor antagonists.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the subject's system and, thus, is subject to metabolism and other like processes, for example, subcutaneous administration.

Regardless of the route of administration selected, the compounds of the present invention, which can be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention can be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the subject being treated, and like factors well known in the medical arts.

A physician or veterinarian having ordinary skill in the art can readily determine and prescribe the effective amount of the pharmaceutical composition required. For example, dosages of a compound of the invention can be determined by deriving dose-response curves using an animal model for the condition to be treated. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous and subcutaneous doses of the compounds of this invention for a subject, when used for the indicated analgesic effects, will range from about 0.0001 to about 100 mg per kilogram of body weight per day, more preferably from about 0.01 to about 100 mg per kg per day, and still more preferably from about 1.0 to about 50 mg per kg per day. An effective amount is that amount treats a gated ion channel-associated state or gated ion channel disorder.

If desired, the effective daily dose of the active compound can be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical composition.

Methods of Treatment

The above compounds can be used for administration to a subject for the modulation of a gated ion channel-mediated activity, involved in, but not limited to, pain, inflammatory disorders, neurological disorders, and any abnormal function of cells, organs, or physiological systems that are modulated, at least in part, by a gated ion channel-mediated activity. Additionally, it is understood that the compounds can also alleviate or treat one or more additional symptoms of a disease or disorder discussed herein.

Accordingly, in one aspect, the compounds of the invention can be used to treat pain, including acute, chronic, malignant and non-malignant somatic pain (including cutaneous pain and deep somatic pain), visceral pain, and neuropathic pain. It is further understood that the compounds can also alleviate or treat one or more additional signs or symptoms of pain and sensory deficits (e.g., hyperalgesia, allodynia, dysesthesia, hyperesthesia, hyperpathia, paresthesia).

In some embodiments of this aspect of the invention, the compounds of the invention can be used to treat somatic or cutaneous pain associated with injuries, inflammation, diseases and disorders of the skin and related organs including, but not limited to, cuts, burns, lacerations, punctures, incisions, surgical pain, post-operative pain, orodental surgery, psoriasis, eczema, dermatitis, and allergies. The compounds of the invention can also be used to treat somatic pain associated with malignant and non-malignant neoplasm of the skin and related organs (e.g., melanoma, basal cell carcinoma).

In other embodiments of this aspect of the invention, the compounds of the invention can be used to treat deep somatic pain associated with injuries, inflammation, diseases and disorders of the musculoskeletal and connective tissues including, but not limited to, arthralgias, myalgias, fibromyalgias, myofascial pain syndrome, dental pain, lower back pain, pain during labor and delivery, surgical pain, post-operative pain, headaches, migraines, idiopathic pain disorder, sprains, bone fractures, bone injury, osteoporosis, severe burns, gout, arthiritis, osteoarthithis, myositis, and dorsopathies (e.g., spondylolysis, subluxation, sciatica, and torticollis). The compounds of the invention can also be used to treat deep somatic pain associated with malignant and non-malignant neoplasm of the musculoskeletal and connective tissues (e.g., sarcomas, rhabdomyosarcomas, and bone cancer).

In other embodiments of this aspect of the invention, compounds of the invention can be used to treat visceral pain associated with injuries, inflammation, diseases or disorders of the circulatory system, the respiratory system, the genitourinary system, the gastrointestinal system and the eye, ear, nose and throat.

For example, the compounds of the invention can be used to treat visceral pain associated with injuries, inflammation and disorders of the circulatory system associated including, but are not limited to, ischaemic diseases, ischaemic heart diseases (e.g., angina pectoris, acute myocardial infarction, coronary thrombosis, coronary insufficiency), diseases of the blood and lymphatic vessels (e.g., peripheral vascular disease, intermittent claudication, varicose veins, haemorrhoids, embolism or thrombosis of the veins, phlebitis, thrombophlebitis lymphadenitis, lymphangitis), and visceral pain associated with malignant and non-malignant neoplasm of the circulatory system (e.g., lymphomas, myelomas, Hodgkin's disease).

In another example, the compounds of the invention can be used to treat visceral pain associated with injuries, inflammation, diseases and disorders of the respiratory system including, but are not limited to, upper respiratory infections (e.g., nasopharyngitis, sinusitis, and rhinitis), influenza, pneumoniae (e.g., bacterial, viral, parasitic and fungal), lower respiratory infections (e.g., bronchitis, bronchiolitis, tracheobronchitis), interstitial lung disease, emphysema, bronchiectasis, status asthmaticus, asthma, pulmonary fibrosis, chronic obstructive pulmonary diseases (COPD), diseases of the pleura, and visceral pain associated with malignant and non-malignant neoplasm of the respiratory system (e.g., small cell carcinoma, lung cancer, neoplasm of the trachea, of the larynx).

In another example, the compounds of the invention can be used to treat visceral pain associated with injuries, inflammation and disorders of the gastrointestinal system including, but are not limited to, injuries, inflammation and disorders of the tooth and oral mucosa (e.g., impacted teeth, dental caries, periodontal disease, oral aphthae, pulpitis, gingivitis, periodontitis, and stomatitis), of the oesophagus, stomach and duodenum (e.g., ulcers, dyspepsia, oesophagitis, gastritis, duodenitis, diverticulitis and appendicitis), of the intestines (e.g., Crohn's disease, paralytic ileus, intestinal obstruction, irritable bowel syndrome, neurogenic bowel, megacolon, inflammatory bowel disease, ulcerative colitis, and gastroenteritis), of the peritoneum (e.g. peritonitis), of the liver (e.g., hepatitis, liver necrosis, infarction of liver, hepatic veno-occlusive diseases), of the gallbladder, biliary tract and pancreas (e.g., cholelithiasis, cholecystolithiasis, choledocholithiasis, cholecystitis, and pancreatitis), functional abdominal pain syndrome (FAPS), gastrointestinal motility disorders, as well as visceral pain associated with malignant and non-malignant neoplasm of the gastrointestinal system (e.g., neoplasm of the oesophagus, stomach, small intestine, colon, liver and pancreas).

In another example, the compounds of the invention can be used to treat visceral pain associated with injuries, inflammation, diseases, and disorders of the genitourinary system including, but are not limited to, injuries, inflammation and disorders of the kidneys (e.g., nephrolithiasis, glomerulonephritis, nephritis, interstitial nephritis, pyelitis, pyelonephritis), of the urinay tract (e.g. include urolithiasis, urethritis, urinary tract infections), of the bladder (e.g. cystitis, neuropathic bladder, neurogenic bladder dysfunction, overactive bladder, bladder-neck obstruction), of the male genital organs (e.g., prostatitis, orchitis and epididymitis), of the female genital organs (e.g., inflammatory pelvic disease, endometriosis, dysmenorrhea, ovarian cysts), as well as pain associated with malignant and non-malignant neoplasm of the genitourinary system (e.g., neoplasm of the bladder, the prostate, the breast, the ovaries).

In further embodiments of this aspect of the invention, compounds of the invention can be used to treat neuropathic pain associated with injuries, inflammation, diseases and disorders of the nervous system, including the central nervous system and the peripheral nervous systems. Examples of such injuries, inflammation, diseases or disorders associated with neuropathic pain include, but are not limited to, neuropathy (e.g., diabetic neuropathy, drug-induced neuropathy, radiotherapy-induced neuropathy), neuritis, radiculopathy, radiculitis, neurodegenerative diseases (e.g., muscular dystrophy), spinal cord injury, peripheral nerve injury, nerve injury associated with cancer, Morton's neuroma, headache (e.g., non-organic chronic headache, tension-type headache, cluster headache and migraine), migraine, multiple somatization syndrome, postherpetic neuralgia (shingles), trigeminal neuralgia complex regional pain syndrome (also known as causalgia or Reflex Sympathetic Dystrophy), radiculalgia, phantom limb pain, chronic cephalic pain, nerve trunk pain, somatoform pain disorder, central pain, non-cardiac chest pain, central post-stroke pain.

In another aspect, the compounds of the invention can be used to treat inflammation associated with injuries, diseases or disorders of the skin and related organs, the musculoskeletal and connective tissue system, the respiratory system, the circulatory system, the genitourinary system and the gastrointestinal system.

In some embodiments of this aspect of the invention, examples of inflammatory conditions, diseases or disorders of the skin and related organs that can be treated with the compounds of the invention include, but are not limited to allergies, atopic dermatitis, psoriasis and dermatitis.

In other embodiments of this aspect of the invention, inflammatory conditions, diseases or disorders of the musculoskeletal and connective tissue system that can be treated with the compounds of the invention include, but are not limited to arthritis, osteoarthritis, and myositis.

In other embodiments of this aspect of the invention, inflammatory conditions, diseases or disorders of the respiratory system that can be treated with the compounds of the invention include, but are not limited to allergies, asthma, rhinitis, neurogenic inflammation, pulmonary fibrosis, chronic obstructive pulmonary disease (COPD), adult respiratory distress syndrome, nasopharyngitis, sinusitis, and bronchitis.

In still other embodiments of this aspect of the invention, inflammatory conditions, disease or disorders of the circulatory system that can be treated with the compounds of the invention include, but are not limited to, endocarditis, pericarditis, myocarditis, phlebitis, lymphadenitis and artherosclerosis.

In further embodiments of this aspect of the invention, inflammatory conditions, diseases or disorders of the genitourinary system that can be treated with the compounds of the invention include, but are not limited to, inflammation of the kidney (e.g., nephritis, interstitial nephritis), of the bladder (e.g., cystitis), of the urethra (e.g., urethritis), of the male genital organs (e.g., prostatitis), and of the female genital organs (e.g., inflammatory pelvic disease).

In further embodiments of this aspect of the invention, inflammatory conditions, diseases or disorders of the gastrointestinal system that can be treated with the compounds of the invention include, but are not limited to, gastritis, gastroenteritis, colitis (e.g., ulcerative colitis), inflammatory bowel syndrome, Crohn's disease, cholecystitis, pancreatitis and appendicitis.

In still further embodiments of this aspect of the invention, inflammatory conditions, diseases or disorders that can be treated with the compounds of the invention, but are not limited to inflammation associated with microbial infections (e.g., bacterial, viral and fungal infections), physical agents (e.g., burns, radiation, and trauma), chemical agents (e.g., toxins and caustic substances), tissue necrosis and various types of immunologic reactions and autoimmune diseases (e.g., lupus erythematosus).

In another aspect, the compounds of the invention can be used to treat injuries, diseases or disorders of the nervous system including, but not limited to neurodegenerative diseases (e.g., Alzheimer's disease, Duchenne's disease), epilepsy, multiple sclerosis, amyotrophic lateral sclerosis, stroke, cerebral ischemia, neuropathies (e.g., chemotherapy-induced neuropathy, diabetic neuropathy), retinal pigment degeneration, trauma of the central nervous system (e.g., spinal cord injury), and cancer of the nervous system (e.g., neuroblastoma, retinoblastoma, brain cancer, and glioma), and other certain cancers (e.g., melanoma, pancreatic cancer).

In further aspects of the invention, the compounds of the invention can also be used to treat other disorders of the skin and related organs (e.g., hair loss), of the circulatory system, (e.g., cardiac arrhythmias and fibrillation and sympathetic hyper-innervation), and of the genitourinary system (e.g., neurogenic bladder dysfunction and overactive bladder).

The present invention provides a method for treating a subject that would benefit from administration of a composition of the present invention. Any therapeutic indication that would benefit from a gated ion channel modulator can be treated by the methods of the invention. The method includes the step of administering to the subject a composition of the invention, such that the disease or disorder is treated.

The invention further provides a method for preventing in a subject, a disease or disorder which can be treated with administration of the compositions of the invention. Subjects "at risk" may or may not have detectable disease, and may or may not have displayed detectable disease prior to the treatment methods described herein. "At risk" denotes that an individual who is determined to be more likely to develop a symptom based on conventional risk assessment methods or has one or more risk factors that correlate with development of a disease or disorder that can be treated according the methods of the invention. For example, risk factors include family history, medication history, and history of exposure to an environmental substance which is known or suspected to increase the risk of disease. Subjects at risk for a disease or condition which can be treated with the agents mentioned herein can also be identified by, for example, any or a combination of diagnostic or prognostic assays known to those skilled in the art. Administration of a prophylactic agent can occur prior to the manifestation of symptoms characteristic of the disease or disorder, such that the disease or disorder is prevented or, alternatively, delayed in its progression.

EXEMPLIFICATION OF THE INVENTION

The invention is further illustrated by the following examples, which could be used to examine the gated ion channel modulating activity of the compounds of the invention. The example should not be construed as further limiting. The animal models used throughout the Examples are accepted animal models and the demonstration of efficacy in these animal models is predictive of efficacy in humans.

Example 1

Identification of ASIC Antagonists using Calcium-Imaging

Cell Culture

ASIC1a expressing HEK293 cells are grown in culture medium (DMEM with 10% FBS), in polystyrene culture flasks (175 mm$^2$) at 37° C. in a humidified atmosphere of 5% $CO_2$. Confluency of cells should be 80-90% on day of plating. Cells are rinsed with 10 ml of PBS and re-suspended by addition of culture medium and trituration with a 25 ml pipette.

The cells are seeded at a density of approximately 1×10$^6$ cells/ml (100 µl/well) in black-walled, clear bottom, 96-well plates pre-treated with 10 mg/l poly-D-lysin (75 µl/well for ≧30 min). Plated cells were allowed to proliferate for 24 h before loading with dye.

Loading with Fluorescent Calcium Dye Fluo-4/AM

Fluo-4/AM (1 mg, Molecular Probes) is dissolved in 912 μl DMSO. The Fluo-4/AM stock solution (1 mM) is diluted with culture medium to a final concentration of 2 μM (loading solution).

The culture medium is aspirated from the wells, and 50 μl of the Fluo-4/AM loading solution is added to each well. The cells are incubated at 37° C. for 30 min.

Calcium Measurements

After the loading period, the loading solution is aspirated and the cells are washed twice with 100 μl modified Assay Buffer (145 mM NaCl, 5 mM KCl, 5 mM $CaCl_2$, 1 mM $MgCl_2$, 10 mM HEPES, pH 7.4) to remove extracellular dye. Following the second wash, 100 μl modified Assay Buffer is added to each well and the fluorescence is measured in FLIPR™ or FlexStation™ (Molecular Devices, USA), or any other suitable equipment known to the skilled in the art.

FLIPR Settings (ASIC1a)

Temperature: Room temperature (20-22° C.)

First addition: 50 μl test solution at a rate of 30 μl/sec and a starting height of 100 μl.

Second addition: 50 μl MES solution (20 mM, 5 mM final concentration) at a rate of 35 μl/sec and a starting height of 150 μl.

Reading intervals: pre-incubation—10 sec×7 and 3 sec×3 antagonist phase—3 sec×17 and 10 sec×12

Addition plates (compound test plate and MES plate) are placed on the right and left positions in the FLIPR tray, respectively. Cell plates are placed in the middle position and the ASIC1a program is effectuated. FLIPR will then take the appropriate measurements in accordance with the interval settings above. Fluorescence obtained after stimulation is corrected for the mean basal fluorescence (in modified Assay Buffer).

Hit Confirmation and Characterization of Active Substances

The MES-induced peak calcium response, in the presence of test substance, is expressed relatively to the MES response alone. Test substances that block the MES-induced calcium response are re-tested in triplicates. Confirmed hits are picked for further characterization by performing full dose-response curves to determine potency of each hit compound as represented by the $IC_{50}$ values (i.e., the concentration of the test substance which inhibits 50% of the MES-induced calcium response; see, for example, FIGS. 1A, 1B and 1C, and FIGS. 13A and 13B).

A summary of $IC_{50}$ values of compounds of the invention as acquired in the calcium mobilization assay are shown below. n=3-7

| Compound | $IC_{50}$ (μM) |
| --- | --- |
| Compound A | 0.10-0.20 |
| Compound B | 0.020-0.030 |
| Compound C | 0.20-0.30 |
| Compound D | 0.250-0.350 |
| Compound H | 0.015-0.25 |
| Compound J | 0.1-0.7 |
| Compound K | 0.3-1.7 |

Example 2

Screening and Bioanalysis of ASIC Antagonists in Heterologous Expression Systems This example describes another in vitro assessment of the activity of the compounds of the present invention.

Another example of an in vitro assessment method consists of using mammalian heterologous expression systems, which are known to the skilled in the art, and include a variety of mammalian cell lines such as COS, HEK, e.g., HEK293 and/or CHO, cells. Cell lines are transfected with gated ion channel(s) and used to perform electrophysiology as follows:

All experiments are performed at room temperature (20-25° C.) in voltage clamp using conventional whole cell patch clamp methods (Neher, E., et al. (1978) *Pfluegers Arch* 375: 219-228).

The amplifier used is the EPC-9 (HEKA-electronics, Lambrect, Germany) run by a Macintosh G3 computer via an ITC-16 interface. Experimental conditions are set with the Pulse-software accompanying the amplifier. Data is low pass filtered and sampled directly to hard-disk at a rate of 3 times the cut-off frequency.

Pipettes are pulled from borosilicate glass using a horizontal electrode puller (Zeitz-Instrumente, Augsburg, Germany). The pipette resistances are 2-3 MOhms in the salt solutions used in these experiments. The pipette electrode is a chloridized silver wire, and the reference is a silver chloride pellet electrode (In Vivo Metric, Healdsburg, USA) fixed to the experimental chamber. The electrodes are zeroed with the open pipette in the bath just prior to sealing.

Coverslips with the cells are transferred to a 15 μl experimental chamber mounted on the stage of an inverted microscope (IMT-2, Olympus) supplied with Nomarski optics. Cells are continuously superfused with extracellular saline at a rate of 2.5 ml/min. After giga-seal formation, the whole cell configuration is attained by suction. The cells are held at a holding voltage of −60 mV and at the start of each experiment the current is continuously measured for 45 s to ensure a stable baseline. Solutions of low pH (<7) are delivered to the chamber through a custom-made gravity-driven flowpipe, the tip of which is placed approximately 50 μm from the cell. Application is triggered when the tubing connected to the flowpipe is compressed by a valve controlled by the Pulse-software. Initially, low pH (in general, pH 6.5) is applied for 5 s every 60 s. The sample interval during application is 5501s. After stable responses are obtained, the extracellular saline as well as the low-pH solution are switched to solutions containing the compound to be tested. The compound is present until responses of a repeatable amplitude are achieved. Current amplitudes are measured at the peak of the responses, and effect of the compounds is calculated as the amplitude at compound equilibrium divided by the amplitude of the current evoked by the pulse just before the compound was included.

The following salt solutions are used: extracellular solution (mM): NaCl (140), KCl (4), $CaCl_2$ (2), $MgCl_2$ (4), HEPES (10, pH 7.4); intracellular solution (mM): KCl (120), KOH (31), $MgCl_2$ (1.785), EGTA (10), HEPES (10, pH 7.2). In general, compounds for testing are dissolved in 50% DMSO at 500 fold the highest concentration used.

Figure 2A:
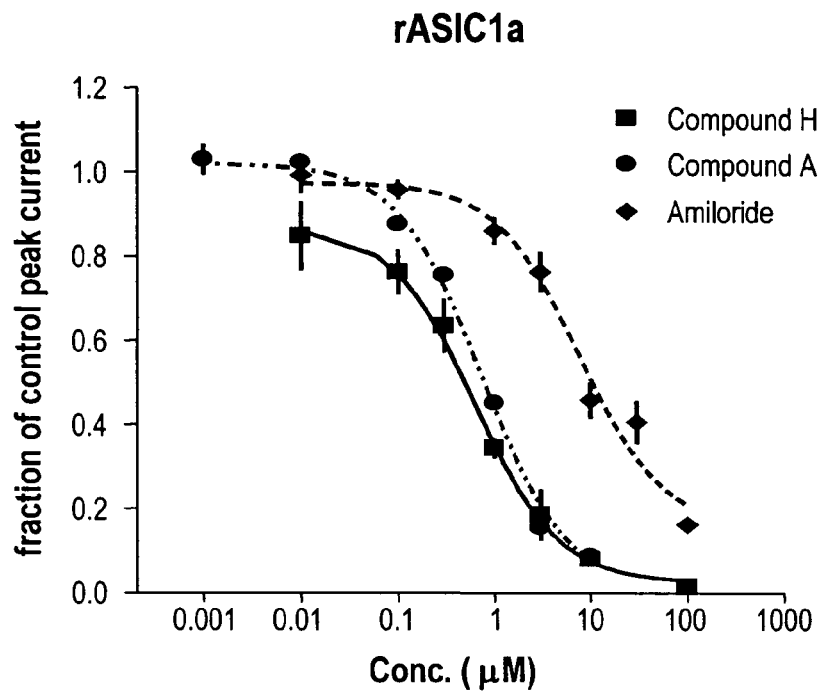
FIGS. 2A and 2B illustrate dose-response curves of the inhibitory effect of Compounds A and H on acid-induced peak inward currents elicited in HEK293 transfected with rat ASIC1a or rat ASIC3, as described in Example 2. Acid-induced inward currents were recorded in the presence and absence of increasing concentrations of Compound A or Compound H using the whole-cell configuration of the patch-clamp method (voltage clamp mode). Compounds A and H dose-dependently inhibit acid-induced rASIC1a and rASIC3 activity.
Figure 2B:
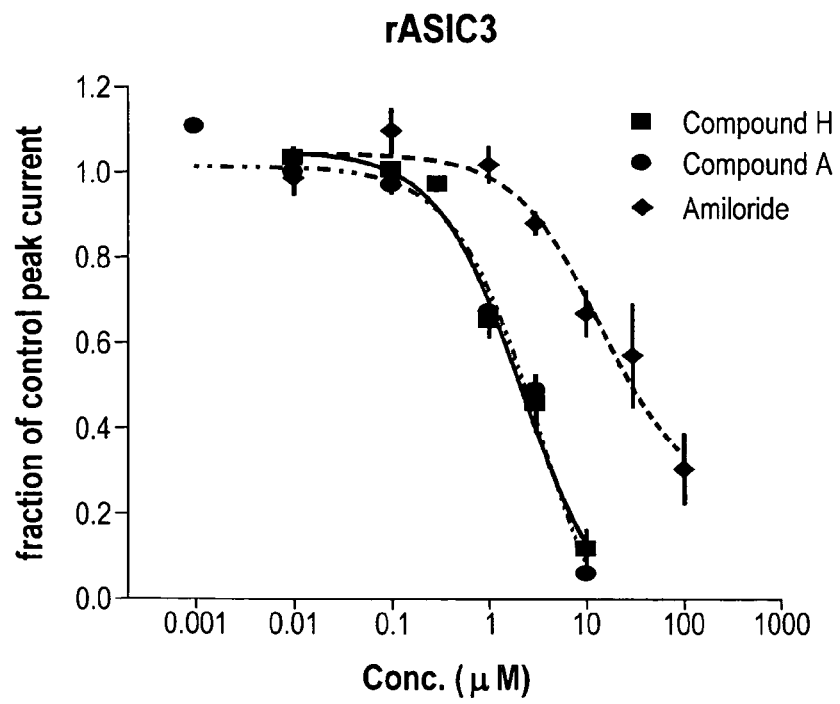

Patch Clamp experiments with Compound A and Compound H demonstrated the efficacy to inhibit recombinant rat ASIC gated channels as illustrated in FIGS. 2A and 2B. HEK293 cells were transfected with rASIC1a or rASIC3 and were used to perform full dose-inhibition curves with Compound A, Compound H and amiloride. Results are expressed as a fraction of the control peak current obtained in the absence of the test substance. These data indicate that both Compounds A and H are more potent antagonists as compared to amiloride.

Figure 3A:
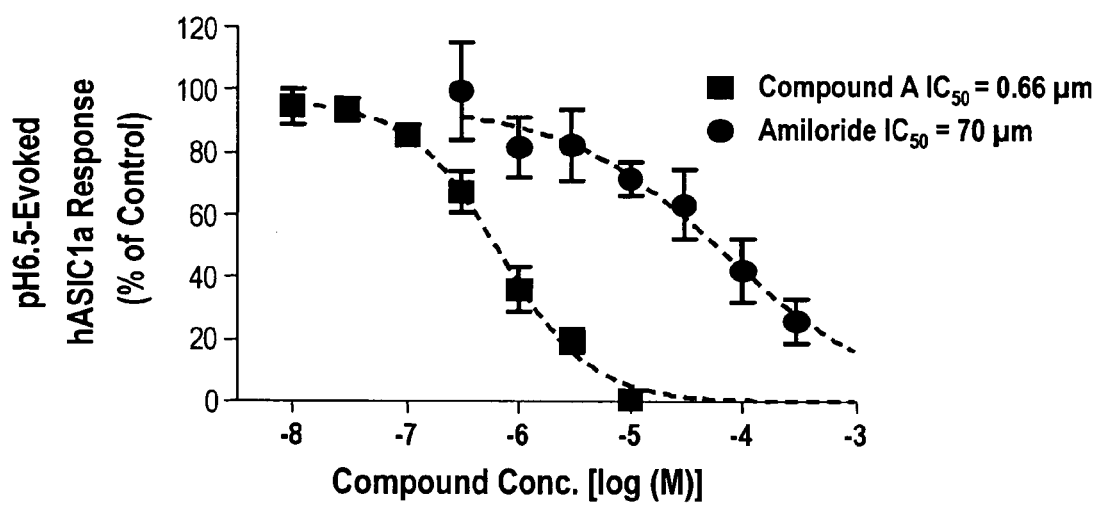
FIG. 3A displays the dose-dependent effect of Compound A and the benchmark compound amiloride on the size of the pH-evoked response. In this example, the size of the pH-evoked response was determined by measuring the area under the curve of the response (total charge transfer) and normalized to the control response.
Figure 3B:
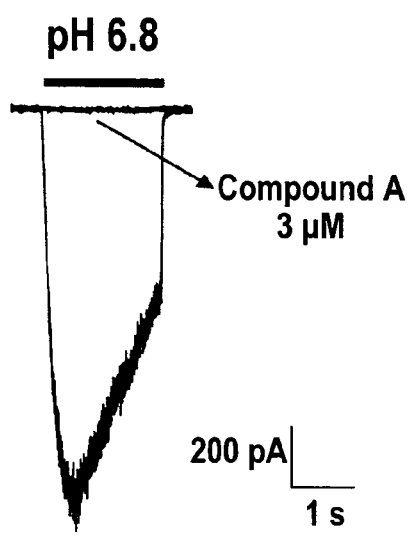
FIG. 3B depicts an example of an hASIC1a current (whole cell voltage clamp, −60 mV) evoked by a pH 6.8-buffered solution (from pH 7.4) in the presence or absence of Compound A (3 μM).
Figure 14A:
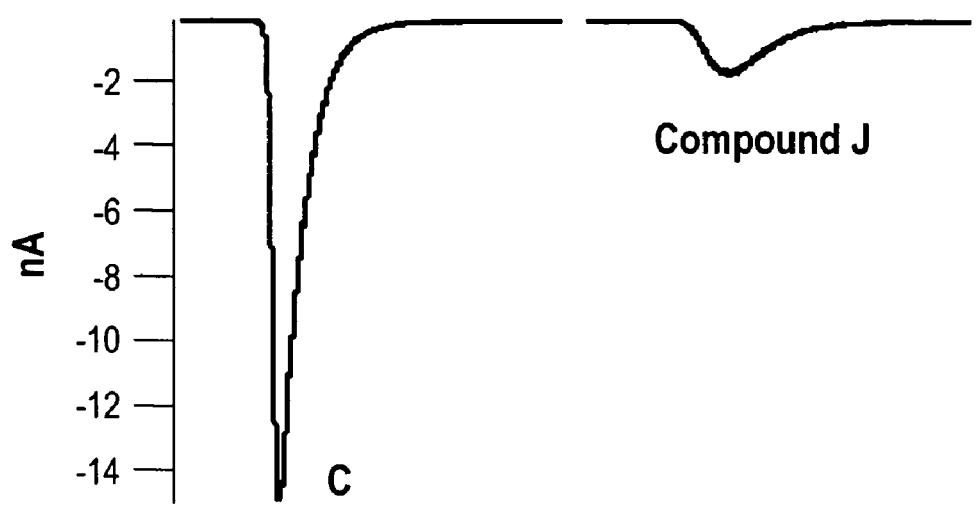
FIGS. 14A and 14B illustrate the inhibitory effects of Compounds J (FIG. 14A) and K (FIG. 14B) on proton-gated currents recorded from CHO cells expressing hASIC1a in Example 2. These endogenous proton-activated inward currents were recorded in the presence and absence of Compound J (1 μM) or Compound K (1 μM) using the whole cell configuration of the patch clamp method (voltage clamp mode).
Figure 14B:
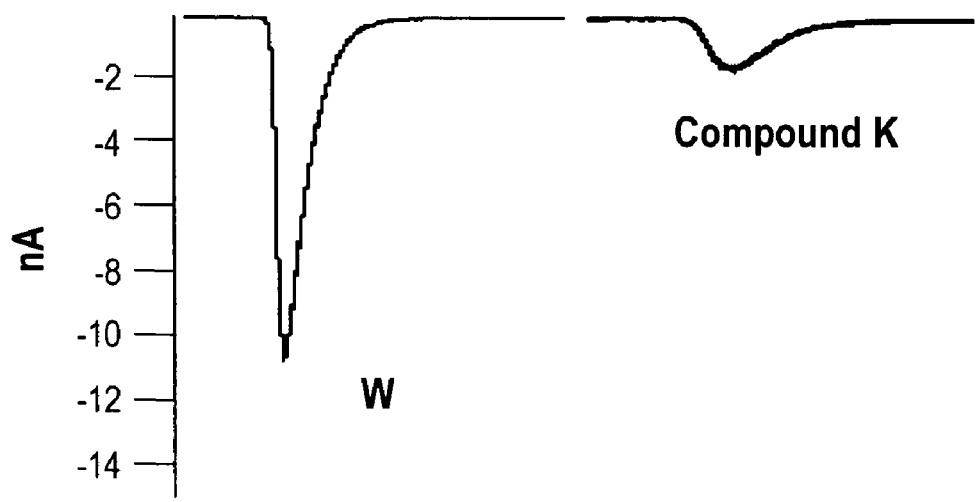

Similar findings are shown in FIG. 3 with the human ASIC1a stably transfected in CHO cells. FIG. 3A compares the dose-response relationship between Compound A and amiloride [determined by measuring the area under the curve of the response (total charge transfer) and normalized to the control response]. Both Compound A (FIG. 3B) and amiloride were able to reduce the human ASIC1a pH-evoked response in a dose-dependent manner. However, Compound A was about 100 fold more potent. FIGS. 14A and 14B show similar results for Compounds J and K.

Figure 4A:
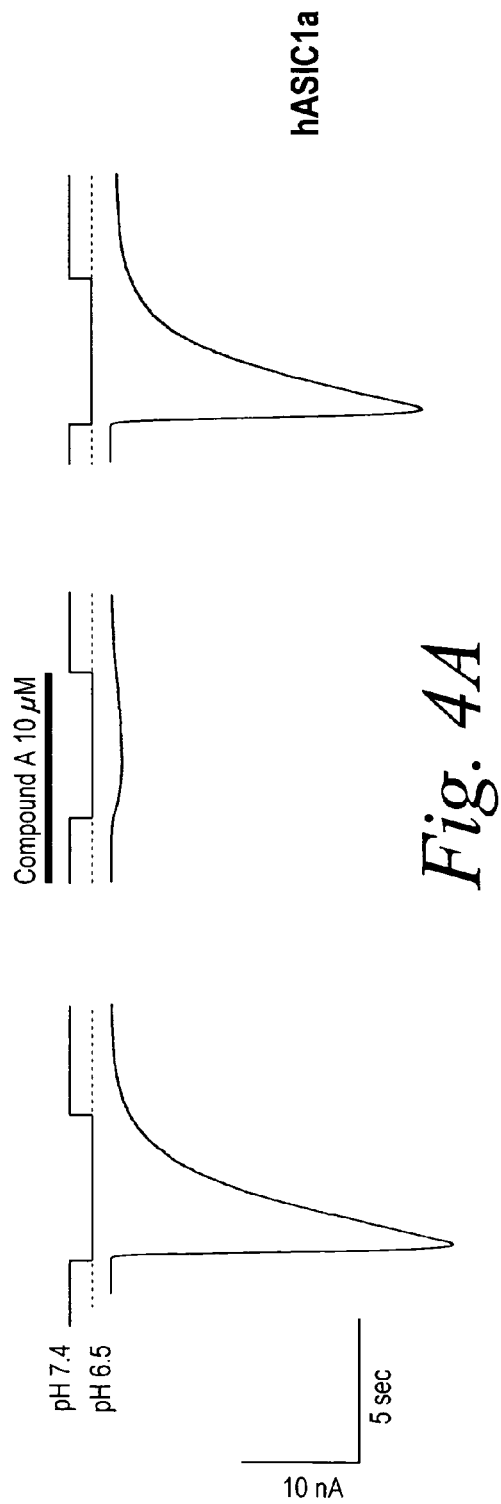
FIGS. 4A and 4B illustrate the inhibitory effects of Compound A on acid-induced activation of recombinant homomeric hASIC1a (FIG. 4A) and heteromeric hASIC1a+3 (FIG. 4B) channels, as described in Example 2. HEK293 cells were transfected either with hASIC1a alone or co-transfected with hASIC1a and hASIC3. Acid-induced inward currents were recorded in the presence and absence of compound A (10 μM) using the whole-cell configuration of the patch-clamp method (voltage clamp mode).
Figure 4B:
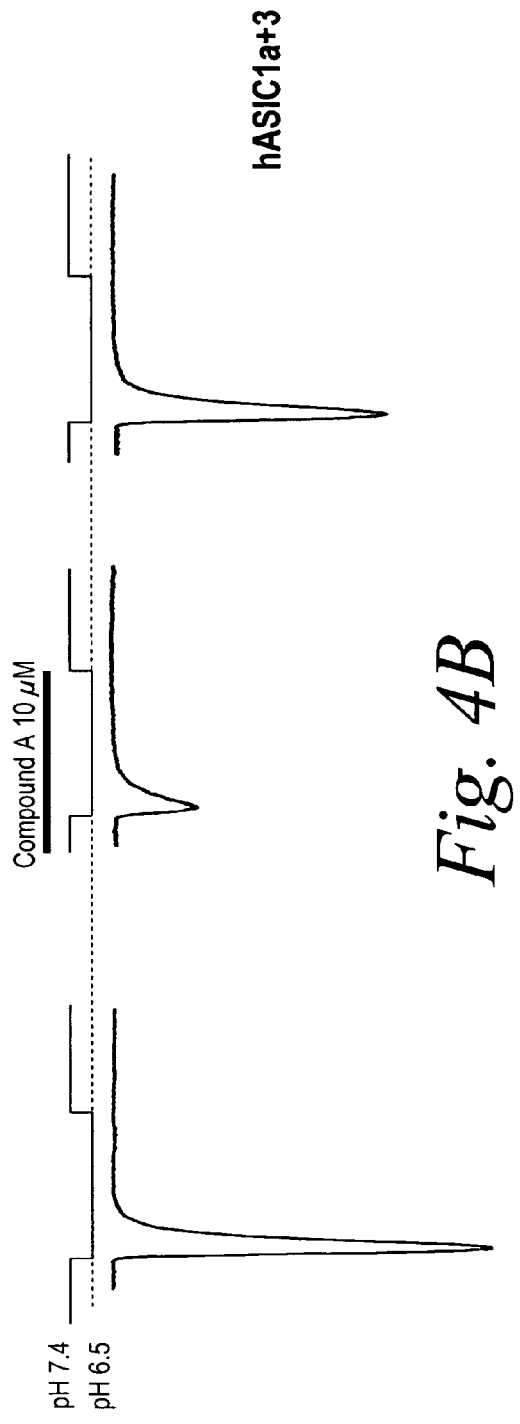

FIGS. 4A and 4B show response to acidic saline in the absence or presence of 10 μM of Compound A recorded from HEK293 cells expressing either hASIC1a alone or HEK293 cells co-expressing hASIC1a and hASIC3 [voltage clamped at −60 mV, extracellular solution surrounding cells was changed rapidly from pH 7.4 to pH 6.5 for 5 sec] (n=3). The data shown in these figures demonstrate that Compound A effectively modulates the activity of these gated ion channels.

Example 3

Screening and Bioanalysis of ASIC Antagonists in *Xenopus laevis* Oocytes

This example describes the in vitro assessment of the activity of the compounds of the present invention.

Two-electrode voltage clamp electrophysiological assays in *Xenopus laevis* oocytes expressing gated ion channels are performed as follows:

Oocytes are surgically removed from adult *Xenopus laevis* and treated for 2 h at room temperature with 1 mg/ml type I collagenase (Sigma) in Barth's solution under mild agitation. Selected oocytes at stage IV-V are defolliculated manually before nuclear microinjection of 2.5-5 ng of a suitable expression vector, such as pcDNA3, comprising the nucleotide sequence encoding a gated ion channel subunit protein. In such an experiment, the oocytes express homomultimeric proton-gated ion channels on their surface. In an alternate experiment, one, two, three or more vectors comprising the coding sequences for distinct gated ion channel subunits are co-injected in the oocyte nuclei. In the latter case, oocytes express heteromultimeric proton-gated ion channels. For example, ASIC2a and/or ASIC3 subunits in pcDNA3 vector are co-injected at a 1:1 cDNA ratio. After 2-4 days of expression at 19° C. in Barth's solution containing 50 mg/ml gentamicin and 1.8 mM $CaCl_2$, gated ion channels are activated by applying an acidic solution (pH <7) and currents are recorded in a two electrode voltage-clamp configuration, using an OC-725B amplifier (Warner Instruments). Currents are acquired and digitized at 500 Hz on an Apple Imac G3 computer with an A/D NB-MIO-16XL interface (National Instruments) and recorded traces are post-filtered at 100 Hz in Axograph (Axon Instruments) (Neher, E. and Sakmann, B. (1976) Nature 260:799-802). Once impaled with the microelectrodes, oocytes are continuously superfused at 10-12 ml/min with a modified Ringer's solution containing 97 mM NaCl, 2 mM KCl, 1.8 mM $CaCl_2$, and 10 mM HEPES brought to pH 7.4 with NaOH (Control Ringer). Test Ringer solution is prepared by replacing HEPES with MES and adjusting the pH to the desired acidic value. Compounds of the present invention are prepared in both the Control and Test Ringer solutions and applied to oocytes at room temperature through a computer-controlled switching valve system. Osmolarity of all solutions is adjusted to 235 mOsm with choline chloride. Similarly, recordings can also be acquired in an automated multichannel oocytes system as the OpusExpress™ (Molecular Devices, Sunnyvale, USA).

Figure 5A:
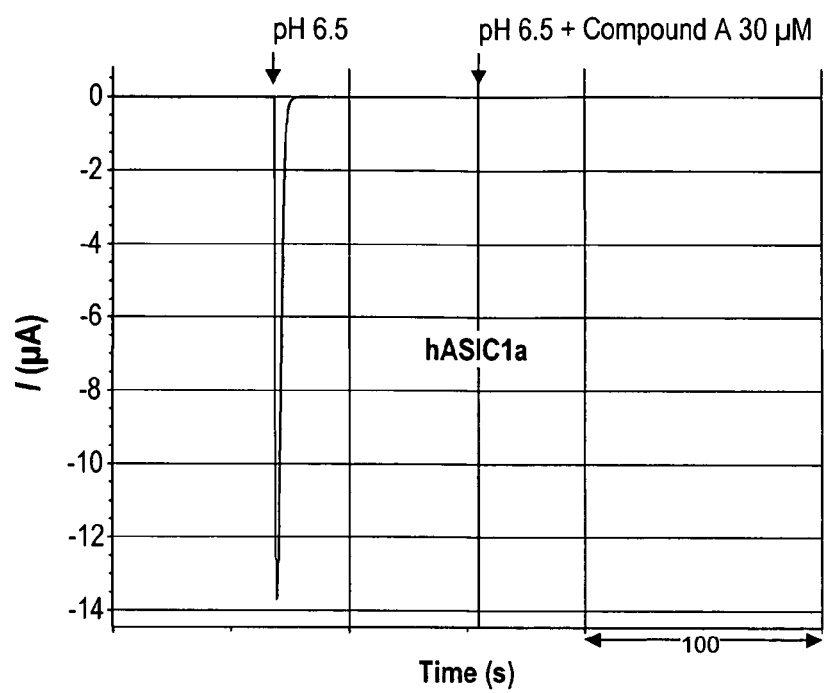
FIGS. 5A and 5B illustrate inhibitory effects of Compound A on acid-induced activation of recombinant homomeric hASIC1a (FIG. 5A) and heteromeric hASIC1a+3 (FIG. 5B) channels, as described in Example 3. Acid-induced currents were recorded from *Xenopus laevis* oocytes using the two-electrode voltage clamp method in the presence and absence of Compound A (30 μM). Oocytes were microinjected with an hASIC1a encoding cDNA alone, or co-injected with hASIC1a and hASIC3 encoding cDNA. These data show that Compound A effectively modulates the activity of these gated ion channels.
Figure 5B:
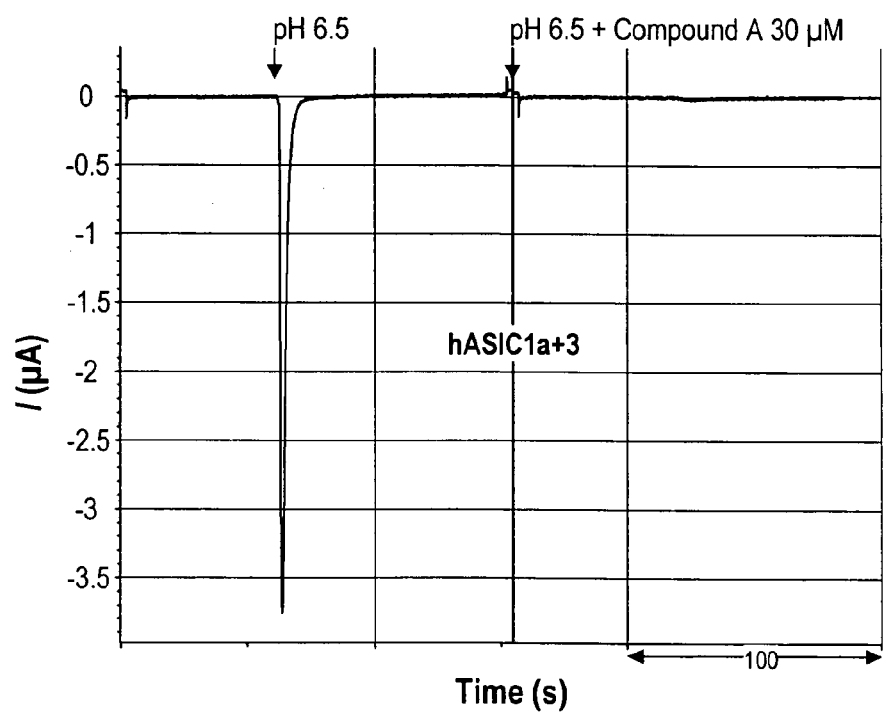

FIGS. 5A and 5B show the inward currents elicited by the application of a pH 6.5 test ringer solution in the presence and absence of Compound A at 30 μM in an OpusExpress™ system. Recordings were acquired from oocytes expressing homomeric hASIC1a (FIG. 5A) or heteromeric hASIC1a+3 (FIG. 5B) using a two electrode voltage-clamp configuration procedure as described herein. Data shown in these figures demonstrate that Compound A effectively modulates the activity of these gated ion channels.

Example 4

Screening and Bioanalysis of ASIC Antagonists in Primary Cell Systems

This example describes another in vitro assessment of the inhibitory activity of the compounds of the present invention utilizing patch-clamp electrophysiology of sensory neurons in primary culture.

Figure 6A:
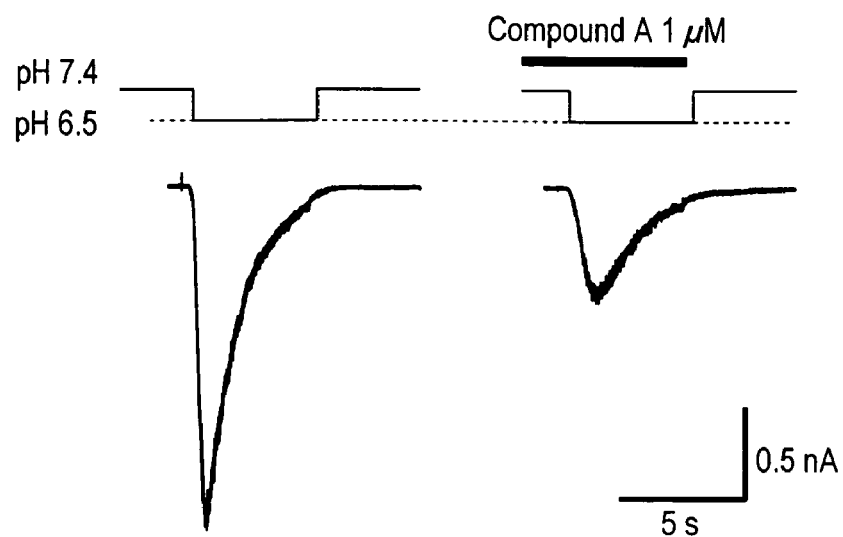
FIGS. 6A and 6B illustrate the inhibitory effects of Compounds A (FIG. 6A) and H (FIG. 6B) on native proton-gated currents recorded from rat dorsal root ganglion nuerons in primary culture, as described in Example 4. These endogenous proton-activated inward currents were recorded in the presence and absence of Compound A (1 μM) or Compound H (1 μM) using the whole cell configuration of the patch clamp method (voltage clamp mode). These data show that Compounds A and H can block native ASIC responses.
Figure 6B:
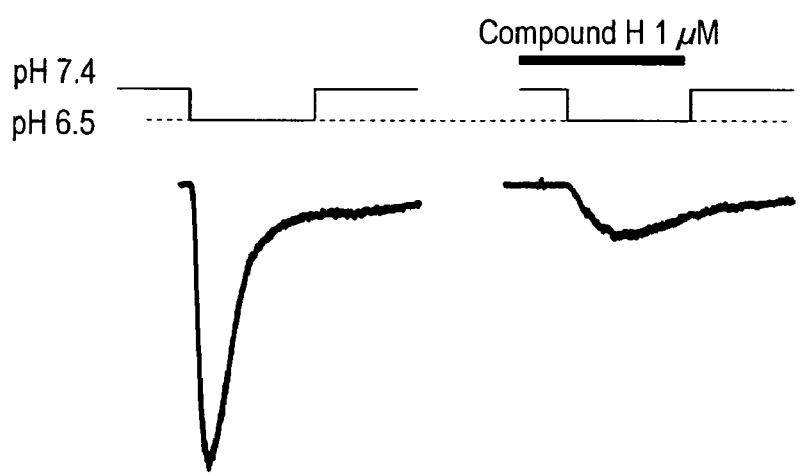
Figure 7A:
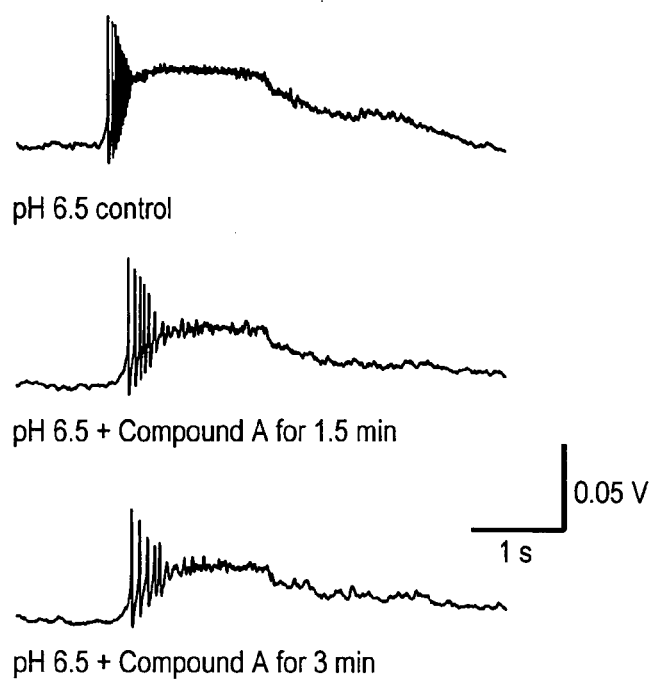
FIGS. 7A and 7B illustrate the inhibitory effects of Compounds A (FIG. 7A) and H (FIG. 7B) on acid-induced action potential generation recorded from rat dorsal root ganglion neurons in primary culture, as described in Example 4. The acid-evoked action potentials were recorded in the presence and absence of Compound A (1 μM) or Compound H (1 μM) using the whole cell configuration of the patch clamp method (current clamp mode).
Figure 7B:
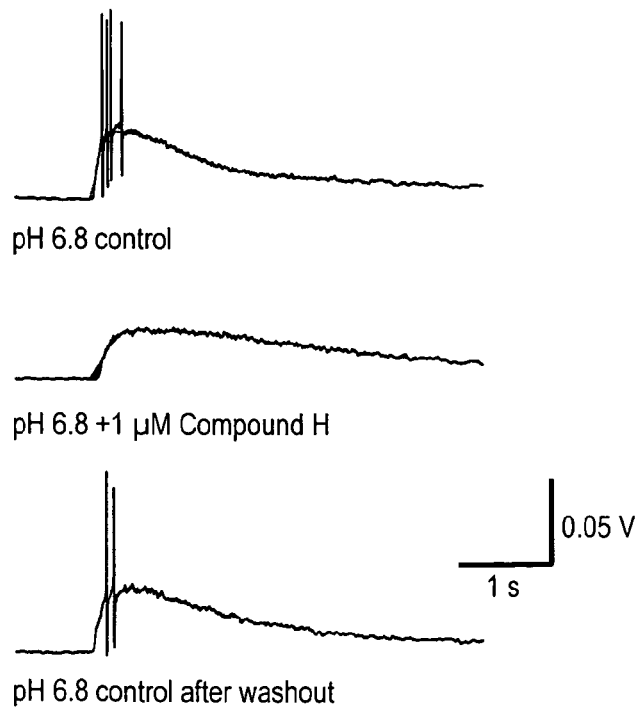

Sensory neurons can be isolated and cultured in vitro from different animal species. The most widely used protocols use sensory neurons isolated from neonatal (Eckert, et al. (1997) *J Neurosci Methods* 77:183-190) and embryonic (Vasko, et al. (1994) *J Neurosci* 14:4987-4997) rat. Trigeminal and dorsal root ganglion sensory neurons in culture exhibit certain characteristics of sensory neurons in vivo. Electrophysiology is performed similarly as described above in Example 2. In the voltage-clamp mode, trans-membrane currents are recorded, as shown in FIGS. 6A and 6B where Compounds A and H at 1 μM inhibit the pH 6.5-induced inward current. In the current-clamp mode, change in the trans-membrane potential are recorded. Under acidic conditions (e.g., pH 6.5) the membrane depolarizes, leading to the firing of action potentials, as shown in FIGS. 7A and 7B. Compounds A and H at 1 μM inhibit the acid-induced membrane depolarization and reduces the ensuing rate of action potential firing. Data shown in these figures demonstrate that Compounds A and H effectively modulate the activity of these native sensory-neuron gated ion channels (n=3).

Example 5

Formalin Model—Model of Acute Tonic Pain

This example describes the in vivo assessment of the inhibitory activity of the compounds of the present invention.

A number of well-established models of pain are described in the literature and are known to the skilled in the art (see, for example, Table 1). This example describes the use of the Formalin test.

Male Sprague-Dawley rats are housed together in groups of three animals under standard conditions with unrestricted access to food and water. All experiments are conducted according to the ethical guidelines for investigations of experimental pain in conscious animals (Zimmerman, 1983)

Assessment of formalin-induced flinching behavior in normal, uninjured rats (body weight 150-180 g) was made with the use of an Automated Nociception Analyser (University of California, San Diego, USA). Briefly, this involved placing a small C-shaped metal band (10 mm wide×27 mm long) on the hindpaw of the rat to be tested. The rats (four rats were included in each testing session) were then placed in a cylindrical plexiglass observation chamber (diameter 30.5 cm and height 15 cm) for 20 min for adaptation purposes prior to being administered drug or vehicle according to the experimental paradigm being followed. After adaptation, individual rats were then gently restrained and formalin (5% in saline, 50 μl, s.c.) was injected into the plantar surface of the hindpaw using a 27G needle. Rats were then returned to their separate observation chambers, each of which were in turn situated upon an enclosed detection device consisting of two electromagnetic coils designed to produce an electromagnetic field in which movement of the metal band could be detected. The analogue signal was then digitised and a software algorithm (LabView) applied to enable discrimination of flinching behaviour from other paw movements. A sampling interval of 1 min was used and on the basis of the resulting response patterns 5 phases of nociceptive behaviour were identified and scored: first phase (P1; 0-5 min), interphase (Int; 6-15 min), second phase (P2; 60 min), phase 2A (P2A; 16-40 min) and phase 2B (P2B; 41-60 min).

Nociceptive behavior was also determined manually every 5 min by measuring the amount of time spent in each of four behavioral categories: 0, treatment of the injected hindpaw is indistinguishable from that of the contralateral paw; 1, the injected paw has little or no weight placed on it; 2, the injected paw is elevated and is not in contact with any surface; 3, the injected paw is licked, bitten, or shaken. A weighted nociceptive score, ranging from 0 to 3 was calculated by multiplying the time spent in each category by the category weight, summing these products, and dividing by the total time for each 5 min block of time. (Coderre et al., Pain 1993; 54: 43). On the basis of the resulting response patterns, 2 phases of nociceptive behavior were identified and scored: first phase (P1; 0-5 min), interphase (Int; 6-15 min), second phase (P2; 60 min), phase 2A (P2A; 16-40 min) and phase 2B (P2B; 41-60 min).

Figure 8A:
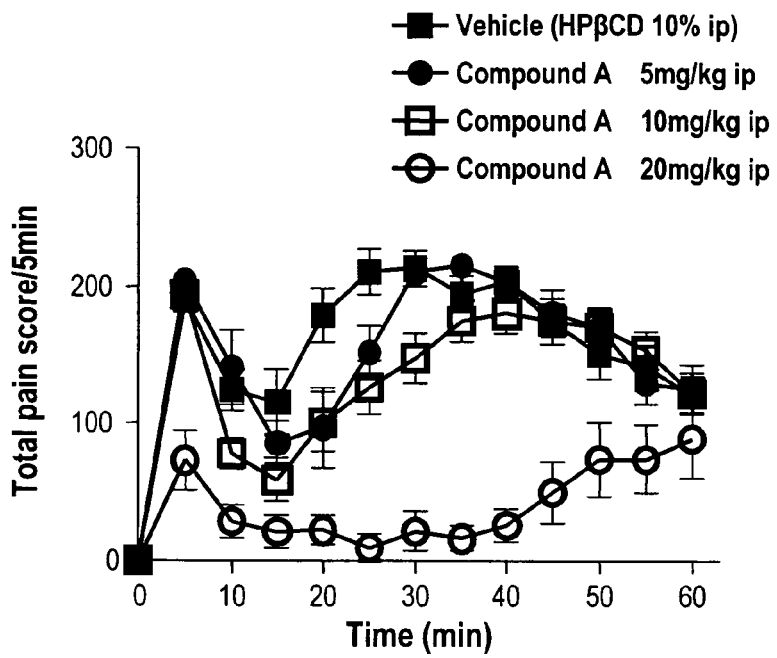
FIG. 8A depicts the total pain behavior (e.g., flinching, licking, biting) over time following intraplantar injection of formalin and FIG. 8B displays the number of licking and biting episodes. These results indicate that Compound A causes a dose-dependent reduction of the pain behavior in the rat.
Figure 8B:
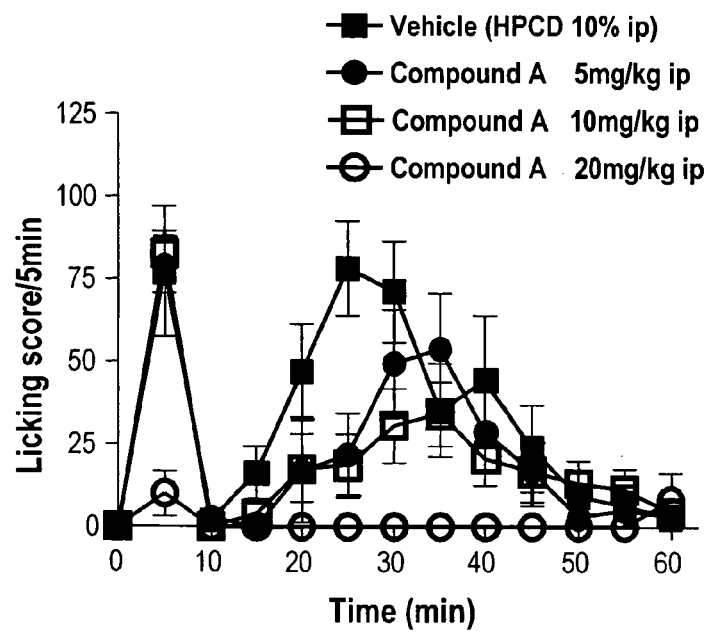
FIG. 8 illustrates the effect of different concentrations of Compound A on formalin-induced pain in rats.
Figure 9A:
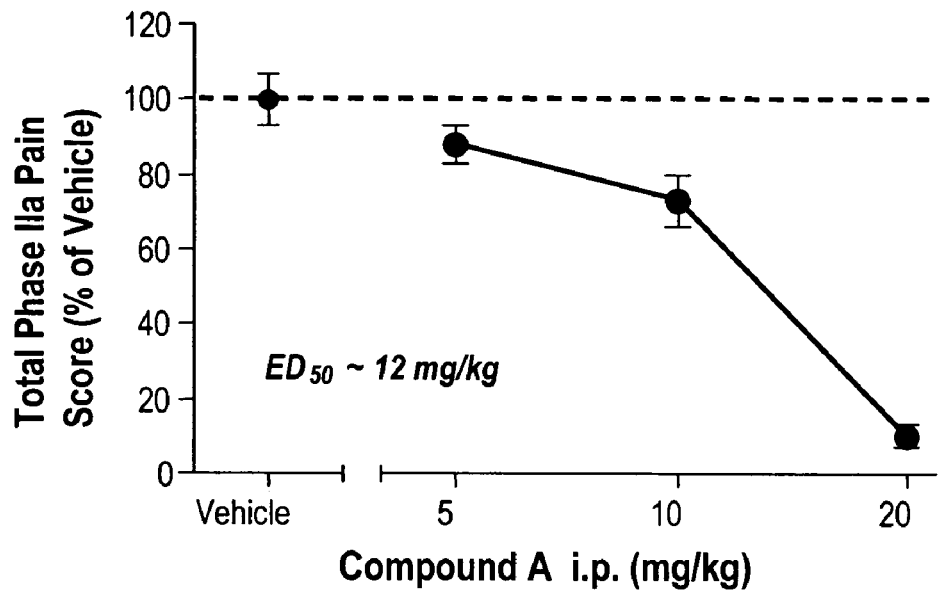
FIG. 9A is the dose-response relationship of Compound A on the total pain score (FIG. 8A) in phase IIa of the formalin test. The effective dose where the pain score is reduced by half ($ED_{50}$) is 12 mg/kg.
Figure 9B:
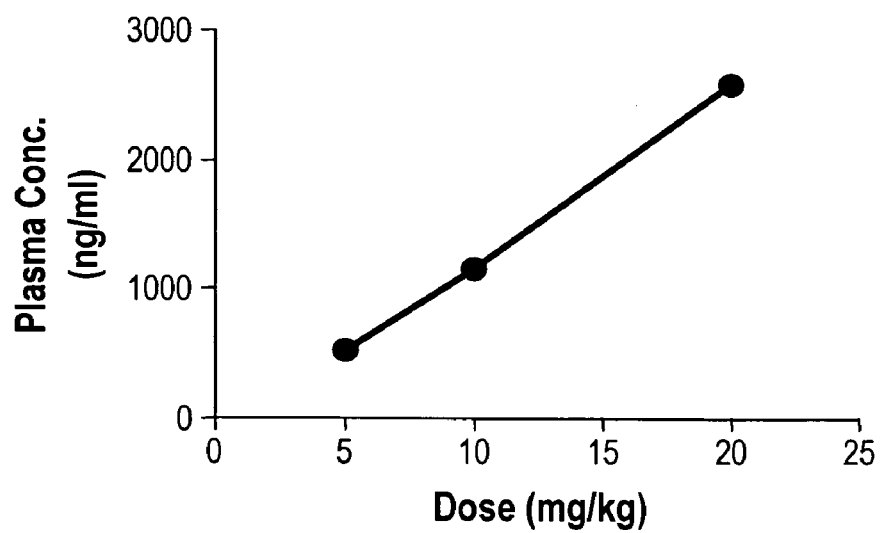
FIG. 9B shows a linear relationship between the dose of Compound A and the plasma level 1.5 h after compound administration.
Figure 10B:
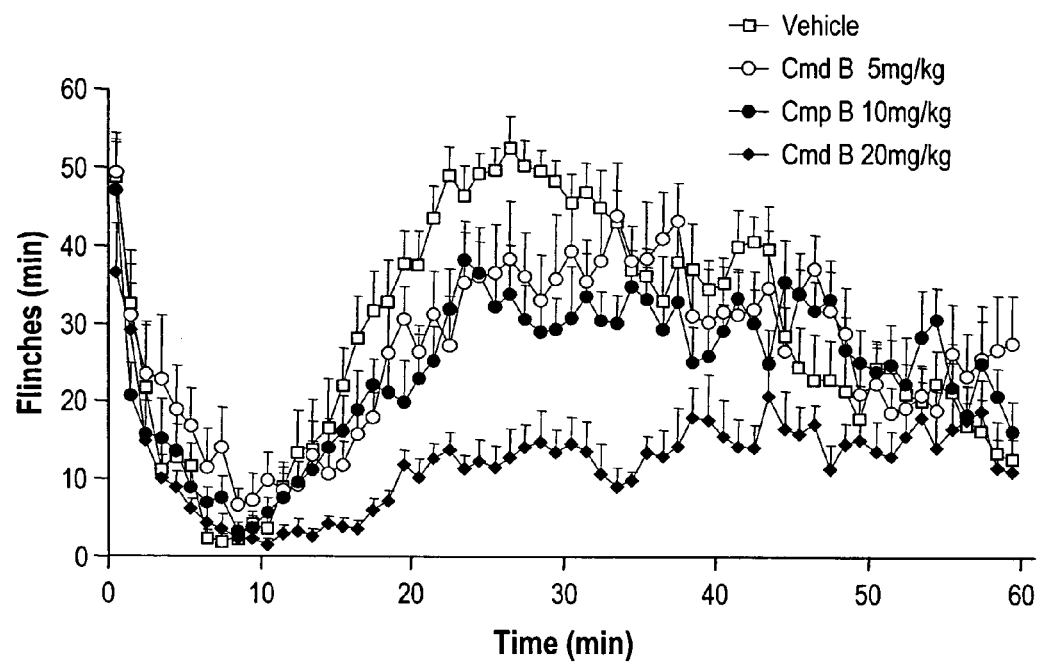
Figure 10B:
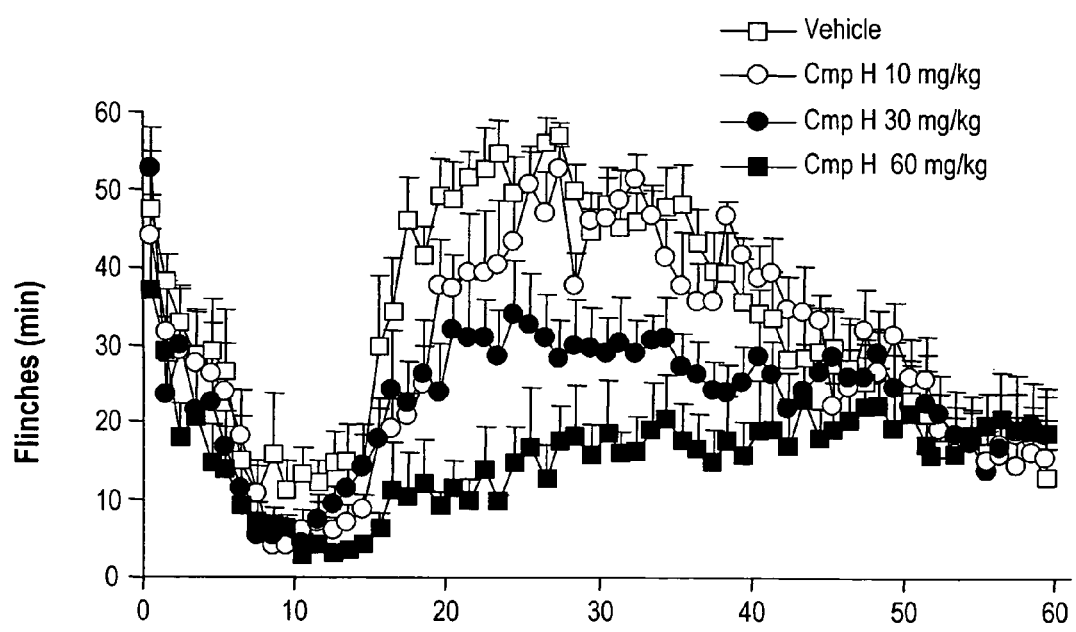

Statistical analysis was performed using Prism™ 4.01 software package (GraphPad, San Diego, Calif., USA). The difference in response levels between treatment groups and control vehicle group was analyzed using an ANOVA followed by Bonferroni's method for post-hoc pair-wise comparisons. A p value <0.05 was considered to be significant FIGS. 8 and 9 are representative examples of the effect of Compound A on pain induced by intraplantar formalin injection. Compound A was administered i.p. 30 min. before the formalin. Compound A was able to reduce the total pain score behavior (flinching, licking, biting) (FIG. 8A) in phase 1 and 2 of the formalin test. These effects on both phases 1 and 2 were quite pronounced when only specific pain behaviors such as liking and biting were observed (FIG. 8B) (n=6-8). The results form these experiments are summarized in FIG. 9, where a clear dose-response relationship for the Phase 2 of the total pain score can be seen (FIG. 9A) with an $ED_{50}$ of about 12 mg/kg. In these experiments, a linear relationship between dose and plasma exposure was observed (FIG. 9B). Similar results are shown for compound B and H (FIGS. 10A, and B) using the Automate Nociceptive Analyzer described above (n=6-8). These results indicate that Compounds A, B and H can block acute tonic pain induced by formalin injection in the paw.

Example 6

CFA Model—Model of Chronic Inflammatory Pain

Injection of complete Freunds adjuvant (CFA) in the hindpaw of the rat has been shown to produce a long-lasting inflammatory condition, which is associated with behavioural hyperalgesia and allodynia at the injection site (Hylden et al., Pain 37: 229-243, 1989) (Blackburn-Munro et al., 2002). Rats (body weight 260-300 g) were given a s.c. injection of CFA (50% in saline, 100 µl, Sigma) into the plantar surface of the hindpaw under brief halothane anaesthesia. After 24 h, they were then tested for hindpaw weight bearing responses, as assessed using an Incapacitance Tester (Linton Instrumentation, UK), (Zhu et al., 2005). The instrument incorporates a dual channel scale that separately measures the weight of the animal distributed to each hindpaw. While normal rats distribute their body weight equally between the two hindpaws (50-50), the discrepancy of weight distribution between an injured and non-injured paw is a natural reflection of the discomfort level in the injured paw (nocifensive behavior). The rats were placed in the plastic chamber designed so that each hindpaw rested on a separate transducer pad. The averager was set to record the load on the transducer over 5 s time period and two numbers displayed represented the distribution of the rat's body weight on each paw in grams (g). For each rat, three readings from each paw were taken and then averaged. Side-to-side weight bearing difference was calculated as the average of the absolute value of the difference between two hindpaws from three trials (right paw reading-left paw reading).

Assessment of thermal hyperalgesia: Baseline and post-treatment withdrawal latencies to a noxious thermal stimulus were measured according to Hargreaves (Hargreaves et al., 1988) using a plantar test analgesia meter (IITC, Woodland Hills, Calif., model # 336). The stimulus intensity was set at 30% of maximum output and the cut-off time was set at 30 seconds. Rats were placed on a glass plate warmed to 28° C. and allowed to habituate to the testing chambers for a minimum of 15 minutes prior to each testing session. The thermal stimulus was applied to the plantar surface of the paw, and the mean latency of three readings on each paw was used as the latency value for each time point. Thermal thresholds were defined as the latency in seconds to the first pain behavior, which includes nocifensive paw withdrawal, flinching, biting and/or licking of the stimulated paw. The mean and standard error of the mean (SEM) were determined for the injured and normal paws for each treatment group.

Figure 11A:
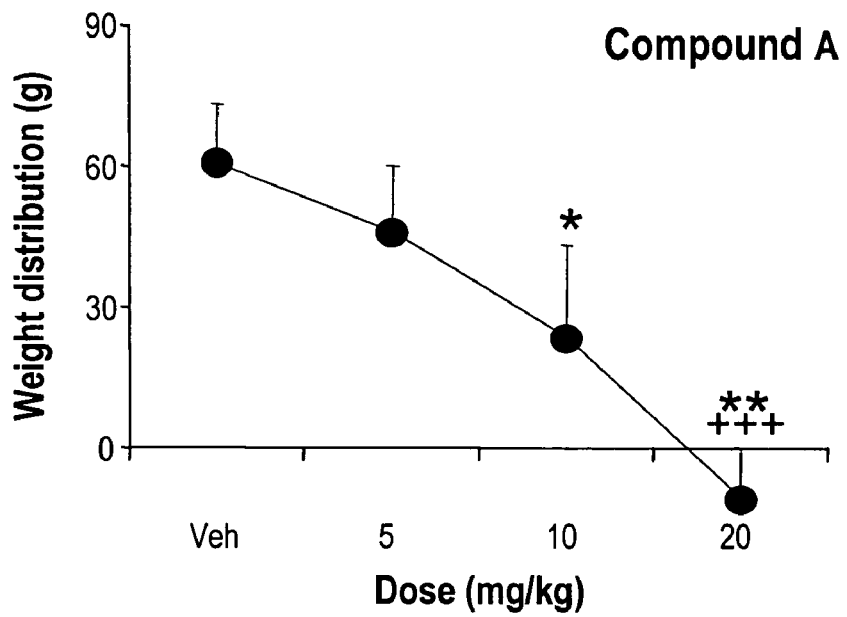
FIGS. 11A, 11B and 11C illustrate the effects of Compounds A, Compound H and morphine, respectively, on inflammatory pain in rats, as described in Example 6. Inflammation was induced by injecting complete Freund's adjuvant (CFA) in the hind paw. These results indicate that Compound A and H cause a dose-dependent reduction of the pain intensity and nocifensive behavior as measured by the incapacitance meter (hindpaw weight bearing difference).
Figure 11B:
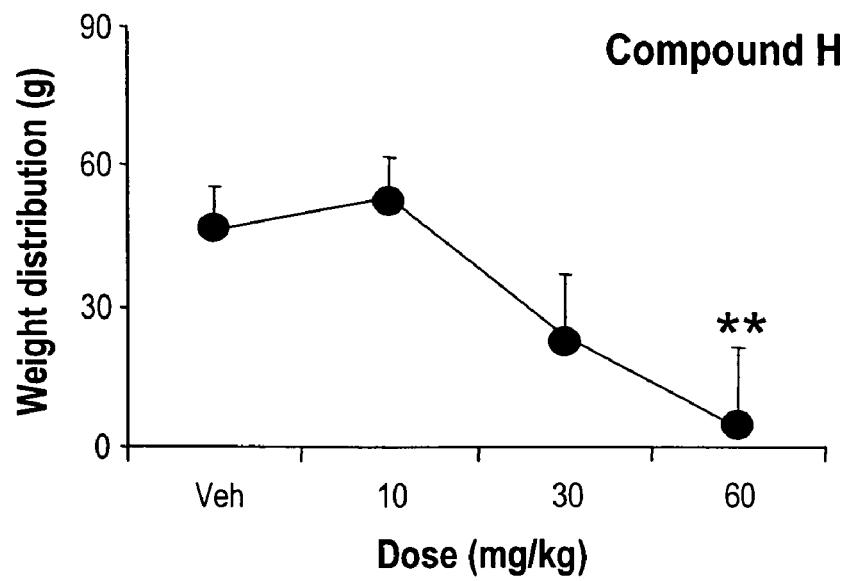
Figure 11C:
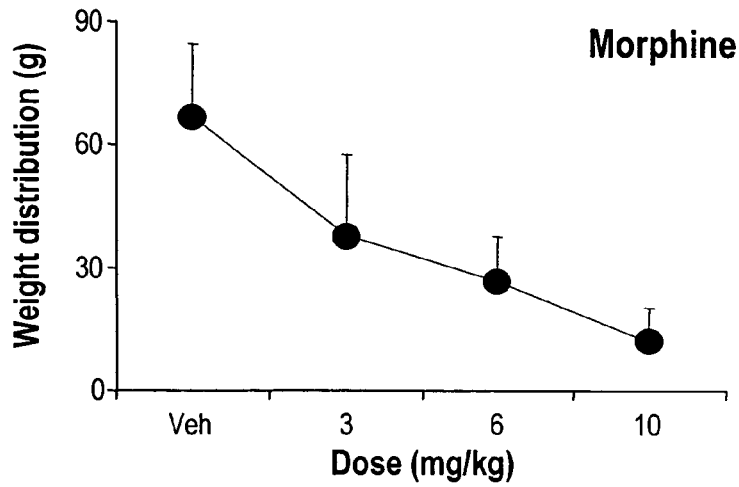

FIGS. 11A, 11B and 11C demonstrate the effect of Compound A, Compound H and morphine on spontaneous pain behaviours in CFA-treated rats. Hindpaw weight bearing responses were measured in male Sprague-Dawley rats for 2-3 days prior to being given a hindpaw injection of CFA. Twenty-four hours later baseline responses were measured and rats were then administered Compound A (5, 10 and 20 mg/kg, i.p.), Compound H (10, 30 and 60 mg/kg) and morphine (3, 6 and 10 mg/kg). Weight bearing responses were then measured at 30, 60 and 120 min after drug or vehicle injection (data shown at 60 min.). Compounds A and H as well as morphine produced a marked dose-dependent attenuation in the CFA-induced change in weight bearing compared with vehicle. Data are expressed as mean +/−SEM. *$P<0.05$, $P<0.01$, * $P<0.001$ vs baseline; +++: $P<0.001$ vs vehicle. All groups n=7-8.

Figure 12:
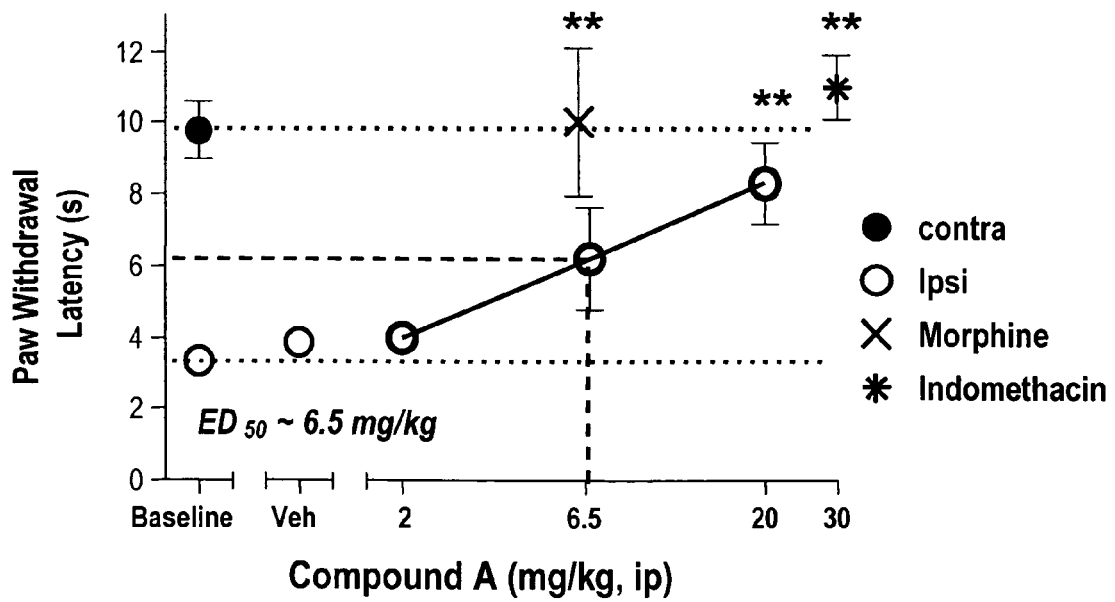
FIG. 12 illustrates dose-dependent analgesic effects of Compound A in the CFA model of chronic inflammatory pain: In vivo dose-dependent reduction of CFA-induced thermal hyperalgesia by Compound A compared to vehicle treated rats. In this model, relative high doses of the benchmark compounds morphine (6 mg/kg) and indomethacin (30 mg/kg) were fully efficacious.
Figure 13A:
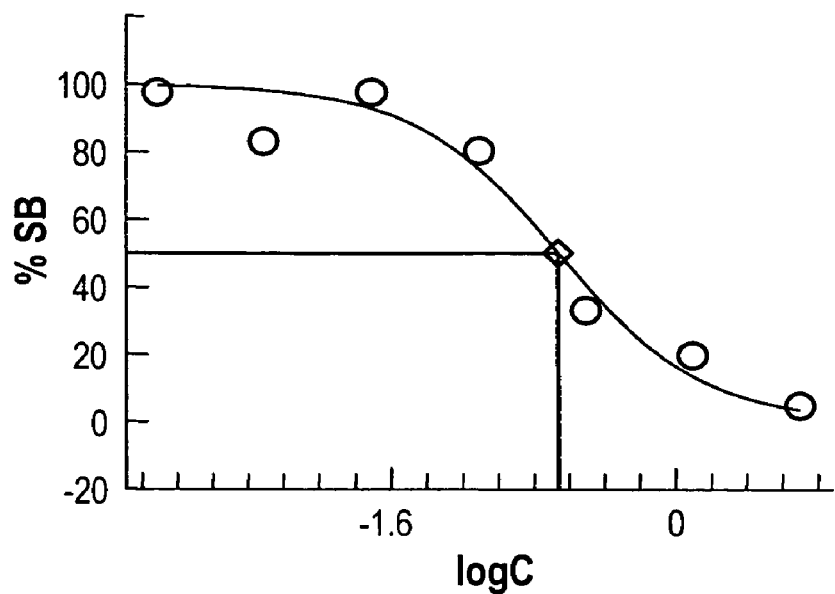
FIGS. 13A and 13B illustrate dose-response curves of the inhibitory effect of compounds J and K on hASIC1a activity as described in Example 1. HEK293 cells were transfected with hASIC1a and cells were exposed to acidic buffer in the absence and presence of increasing concentrations of Compounds J or K. Gated-channel activity was determined by measuring intracellular calcium variation using a calcium-selective fluorescent dye. Compounds E, F and G dose-dependently inhibit acid-induced hASIC1A activity.
Figure 13B:
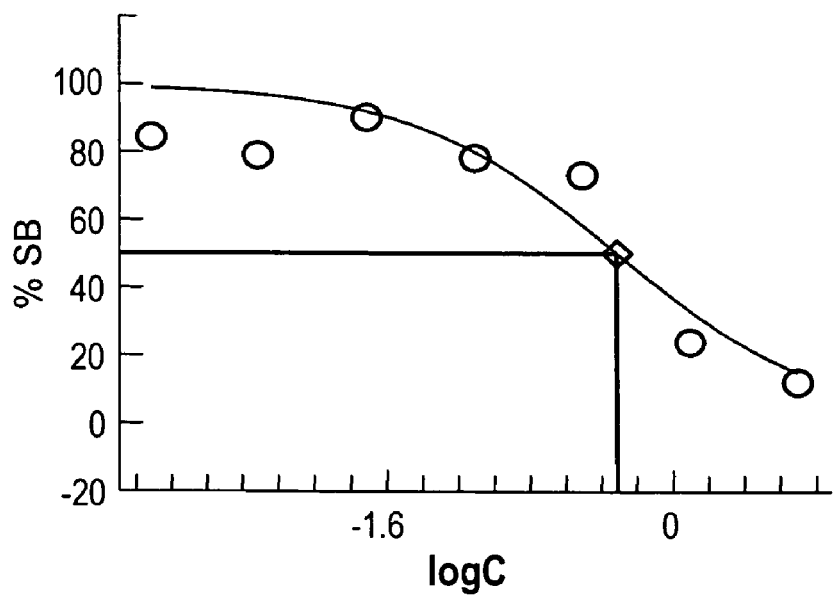

FIG. 12 depicts the dose-dependent reversal of the CFA-induced thermal hyperalgesia by Compound A. CFA was injected 48 h prior to testing of Compound A. Thermal hyperalgesia was measured 3h after i.p. administration of Compound A. Compound A was capable of fully reversing the thermal hyperalgesia with an $ED_{50}$ of 6.5 mg/kg. For comparison, results with morphine (6 mg/kg sc) and indomethacin (30 mg/kg po) are shown. These results demonstrate that Compounds A is efficacious in both mechanical and thermal modalities. Data are expressed as mean±SEM, (n=10). **$P<0.01$, vs. baseline.

Example 7

Cloning and Expression of ASICs

The cDNA for ASIC1a and ASIC3 can be cloned from rat poly(A)$^+$ mRNA and put into expression vectors according to Hesselager et al. (J Biol. Chem. 279(12):11006-15 2004). All constructs are expressed in CHO-K1 cells (ATCC no. CCL61) or HEK293 cells. CHO-K1 cells are cultured at 37° C. in a humidified atmosphere of 5% $CO_2$ and 95% air and passaged twice every week. The cells are maintained in DMEM (10 mM HEPES, 2 mM glutamax) supplemented with 10% fetal bovine serum and 2 mM L-proline (Life Technologies). CHO-K1 cells are co-transfected with plasmids containing ASICs and a plasmid encoding enhanced green fluorescent protein (EGFP) using the lipofectamine PLUS transfection kit (Life Technologies) or Lipofectamine 2000 (Invitrogen) according to the manufacturer's protocol. For each transfection it is attempted to use an amount of DNA that yield whole-cell currents within a reasonable range (0.5 nA-10 nA), in order to avoid saturation of the patch-clamp amplifier (approximately 50 ng for ASIC1a and ASIC3). Electrophysiological measurements are performed 16-48 hours after transfection. The cells are trypsinized and seeded on glass coverslips precoated with poly-D-lysine, on the day the electrophysiological recordings were performed.

Example 8

Synthetic Procedure for Compound A

5-Bromo-8-nitroisoquinoline (II)

5-Bromo-8-nitroisoquinoline was prepared from the corresponding isoquinoline (I) according to the procedure found in William Dalby Brown and Alex Haahr Gouliaev, Organic Syntheses Vol. 81, p 98.

5-Bromo-1,2,3,4-tetrahydro-2-methyl-8-nitroisoquinoline (III)

5-Bromo-8-nitroisoquinoline (II, 5 g, 19.7 mmol) was suspended in anhydrous DMF (20 mL) under nitrogen atmosphere and the mixture was heated until the isoquinoline was dissolved completely. Methyl-p-toluenesulphonate (4 g, 21.5 mmol) was added dropwise, whereafter heated at 85° C. for 24 hours. After cooling in an ice bath, the solid was collected by filtration and washed with ether and acetone to give the isoquinolinium salt (used without further purification).

The isoquinolinium salt was dissolved in acetic acid (30 ml) and sodium borohydride (0.87 g) was added. The reaction mixture was stirred at room temperature overnight. The acetic acid was removed under vacuum and then diluted with water. The solution was basified with 10N NaOH (pH=8) and the precipitated product was collected by filtration, washed with water and dried under vacuum to give light sensitive 5-bromo-1,2,3,4-tetrahydro-2-methyl-8-nitroisoquinoline (4.7 g).

5-Bromo-1,2,3,4-tetrahydro-2-methylisoquinolin-8-amine (IV)

To a solution of N-methyl-5-bromo-8-nitro-1,2,3,4-tetrahydroisoquinoline (III, 4.7 gm, 17.3 mmol) in ethanol (50 ml), Raney Nickel (solution in water, 1.5 g) was added. The reaction mixture was stirred at room temperature overnight under $H_2$. The mixture was filtered through celite and solvent was removed under vacuum to give IV.

N-(5-Bromo-1,2,3,4-tetrahydro-2-methylisoquinolin-8-yl)-2-(hydroxyimino)acetamide (V)

A mixture of 5-bromo-1,2,3,4-tetrahydro-2-methylisoquinolin-8-amine (IV, 3.25 g, 13.5 mmol), chloral hydrate (2.3 g), hydroxylamine hydrochloride (2.9 g), 12 g $Na_2SO_4$ (12 g) in $H_2O$:EtOH (3:1, 50 mL) was refluxed for 1 hr whereafter it was cooled to 60° C. and carefully basified with 4N NaOH to pH=7 and allowed to cool. The solid was collected by filtration, washed with water and dried under vacuum to give V.

5-Bromo-6,7,8,9-tetrahydro-8-methyl-1H-pyrrolo[3,2,-h]lisoquinoline-2,3-dione (VI)

To preheated sulphuric acid (20 mL, 70° C.), N-(5-bromo-1,2,3,4-tetrahydro-2-methylisoquinolin-8-yl-2-(hydroxyimino)acetamide (V, 3.5 g) was added portion-wise over a period of 30 min. The heating was continued further for 1 hr. The reaction mixture was cooled to room temperature and quenched by pouring over ice cold water (100 mL) and then neutralized with aqueous 10N NaOH. The precipitated product was filtered, washed with water to give isatin VI.

5-Bromo-6,7,8,9-tetrahydro-3-(hydroxyimino)-8-methyl-1H-pyrrolo[3,2,-h]lisoquinoline-2(3H)-one (VII)

To the solution of isatin VI (3.5 g) in methanol (50 ml), hydroxylamine hydrochloride (2.0 g) was added and mixture was refluxed 1 hr. The reaction mixture was cooled to room temperature and solid was collected by filtration, washed with ethanol and ether and dried under vacuum.

Compound A

A mixture of 5-bromo-6,7,8,9-tetrahydro-3-(hydroxyimino)-8-methyl-1H-pyrrolo[3,2-h]isoquinolin-2(3H)-one (VII, 100 mg), 5-fluoro-2-methoxyphenylboronic acid (60 mg), potassium phosphate (72 mg), dichlorobis(triphenylphosphine)palladium(II) (11 mg), water (1.5 mL) and DMF (3 mL) was irradiated under Microwave (120° C., 10 min). The solvent was evaporated under vacuum and residue was chromatographed on silica gel to give 5-(5-fluoro-2-methoxyphenyl)-6,7,8,9-tetrahydro-3-(hydroxyimino)-8-methyl-1H-pyrrolo[3,2,-h]isoquinolin-2(3H)-one.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications and other references cited herein are hereby expressly incorporated herein in their entireties by reference.

We claim:

1. A compound 5-(5-fluoro-2-methoxyphenyl)-6,7,8,9-tetrahydro-3-(hydroxyimino)-8-methyl-1H-pyrrolo[3,2-h]isoquinoline-2(3H)-one.

2. A compound 5-(5-fluoro-2-methoxyphenyl)-6,7,8,9-tetrahydro-3-(hydroxyimino)-8-methyl-1H-pyrrolo[3,2-h]isoquinoline-2(3H)-one, or a pharmaceutically acceptable salt thereof.

* * * * *